US010287335B2

(12) United States Patent
Zur Hausen et al.

(10) Patent No.: US 10,287,335 B2
(45) Date of Patent: May 14, 2019

(54) HCBI SEQUENCES AS AN EARLY MARKER FOR THE FUTURE DEVELOPMENT OF CANCER AND DISEASES OF THE CNS AND AS A TARGET FOR CANCER TREATMENT AND PREVENTION

(71) Applicant: DEUTSCHES KREBSFORSCHUNGSZENTRUM, Heidelberg (DE)

(72) Inventors: Harald Zur Hausen, Wald-Michelbach (DE); Ethel-Michele De Villiers, Wald-Michelbach (DE); Karin Gunst, Hirschberg (DE); Mathis Funk, Illkirch (FR); Iranzu Lamberto Perez, Navarra (ES)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 0 days.

(21) Appl. No.: 15/134,436

(22) Filed: Apr. 21, 2016

(65) Prior Publication Data

US 2016/0244492 A1    Aug. 25, 2016

Related U.S. Application Data

(63) Continuation-in-part of application No. PCT/EP2014/002912, filed on Oct. 30, 2014.

(30) Foreign Application Priority Data

Oct. 30, 2013 (EP) ..................................... 13005138

(51) Int. Cl.
| | |
|---|---|
| C07K 14/47 | (2006.01) |
| C12Q 1/68 | (2018.01) |
| C12N 15/113 | (2010.01) |
| C07K 16/18 | (2006.01) |
| C12Q 1/6883 | (2018.01) |
| C12Q 1/70 | (2006.01) |

(52) U.S. Cl.
CPC .............. C07K 14/47 (2013.01); C07K 16/18 (2013.01); C12N 15/113 (2013.01); C12Q 1/6883 (2013.01); C12Q 1/701 (2013.01); C12N 2310/11 (2013.01); C12N 2310/14 (2013.01)

(58) Field of Classification Search
None
See application file for complete search history.

(56) References Cited

U.S. PATENT DOCUMENTS 6,498,242 B1 * 12/2002 Cheng .................... C12N 15/52
435/142
2016/0244492 A1 * 8/2016 Zur Hausen ......... C12Q 1/6883

OTHER PUBLICATIONS

Whitley et al. (Genome Announcements. Jul./Aug. 2014; 2 (4): e00849-14).*
Yeh et al. (PNAS. Jul. 2017; 114 (27): 7118-7123).*
Rohrmann et al. (Proceedings of the Nutrition Society. 2016; 75: 233-241).*
Eilebrecht et al. (Scientific Reports. Feb. 2018; 8 (1): 2851).*
Canadian Office Action dated Feb. 20, 2017 which issued during prosecution of Canadian Application No. 2,922,872.
Notification of Reasons for Refusal dated Feb. 20, 2017, which issued during prosecution of Japanese Application No. 2016-549626.
International Search Report dated May 4, 2015, which issued during prosecution of International Application No. PCT/EP2014/002912.
Brassard, et al. "Molecular detection of bovine and porcine Torque teno virus in plasma and feces" Veterinary Microbiology, Nov. 2007, 126(1-3):271-276.
Fuchs, et al. "Detection of bovine herpesvirus 1 in blood from naturally infected cattle by using a sensitive PCR that discriminates between wild-type virus and virus lacking glycoprotein E" Journal of Clinical Microbiology, Aug. 1999, 37(8):2498-2507.
Giovanna, et al. "Bovine leukemia virus gene segment detected in human breast tissue" Open Journal of Medical Microbiology, Mar. 2013, 3:84-90.
Leary, et al. "Improved detection systems for TT virus reveal high prevalence in humans, non-human primates and farm animals" Journal of General Virology, 1999, 80:2115-2120.
Schuurman, et al. "Bovine polyomavirus, a frequent contaminant of calf serum" Biologicals, 1991, 19:265-270.
Spradbrow, et al. "Skin cancer and papillomaviruses in cattle" Journal of Comparative Pathology, Jul. 1987, 97(4):469-479.
Zur Hausen, et al. "The search for infectious causes of human cancers: Where and why" Virology, Sep. 2009, 392(1):1-10.
Zur Hausen. "Red Meat consumption and cancer: reasons to suspect involvement of bovine infectious factors in colorectal cancer" International Journal of Cancer, 2012, 130:2475-2483.
"Viren in Rindfleisch konnen Darmkrebs verursachen (Viruses in beef may cause colon cancer)" Online Focus, Mar. 4, 2012.

* cited by examiner

*Primary Examiner* — Shanon A. Foley
(74) *Attorney, Agent, or Firm* — Duane Morris LLP; Thomas J. Kowalski; Deborah L. Lu

(57) ABSTRACT

The present invention relates to HCBI (Healthy Cattle Blood Isolate) nucleotide sequences as well as probes and primers comprising part of said nucleotide sequences and antibodies against polypeptides encoded by said nucleotide sequences. Said compounds are useful as early markers for the future development of cancer and diseases of the CNS.

8 Claims, 29 Drawing Sheets

Specification includes a Sequence Listing.

Figure 1A

HCBI1.225
*rmf.C2.F8E.4.3kr (2251)*

```
CCTTTTCCCT GATTACAAGC TCCCATCTGC TCCAGATCGG GAGCTTTTAG CCATCCCGAA TGGGTGGCGA CACAAATTAC
AGGCGAAAAA AAAGACCATA TTGGCCTTCG GTTTAGATTG GCTGCCGTAT CAGCCAATTT GATTGAGTGC CGCATCACTC
AATCTATCAA GTGCCGCATC ACCTGATTAC TCAAATCTAC ATGAAATTTT CTTTCTTGCA AACGGTTCAG AAAAGCATTA
TAAATATCCC ACCAATGAAT CATAAATGAA TCACTATAGA TCAGGAAACA ACTATGAAAC TCCATAATCC AAATCCAAAT
GAGCCTACTA ACCTACAAAT GCTTGTTGCA GAAGTTAAAA AATCCGCTTC AAGCTCTTAT CACGGTGGTT ATATTCAAGT
TCCTTTCCGT GTTGAGTTTG CATCATATAC ACGCCTTGAG GCACTTGTTA AACATACTGG CTCAAGTCGC AATAAGATCA
TGAATGATCT GTTAAGAATC GGTATTGAAA CTCTAGCTGC CTCTTTGGAT GATGAAACAA TTAAAACTCT TTTTGAAATT
GAAACCTCAA TCACTGCGGA TCTCTATGCT TCAGGAAAAA TTAAATCAGG GGATCAATCA GATGATTAAT TTACAAGGAA
CTCTAATTAA TGCTTTTCGT GTGGATGGTG GTAAAGGTAA AGACGGCAAA GAATATGAAG CGCGTGACAA GGTGCAAATT
CTTGGTTCGT TGGAGTTACC CAATGGGGAA ATTAAACACG AACTTGTTGA CCTAACAGTT GAGGATTCTC GACTTTTTGA
ACCATTCAAA AATCAGGTTA TTAGCATCTC ATGTGGTGCT ATGGCTGTCG GTCGTAATGT TATTTTTTAT GTTCGCAAAG
GCGCAAAACC AGTTTTAGCA GAACAAATGT GAAACCCGAA AAAAAAAACA GTGAGTTAGC GAAGCAACTC GATACTATTG
ATTAACTAGG GGACAAAAAT TGACTATAAA AGACAATAAA AAAGCCCATA ATTCGGATGC TTTGGCGGGC GATGAATTAC
AGGCTTTGCA ATCTGCTAAG GCAGATCAAC ACAGGGATAG AATAACACGT TTTGGAAATT TGAAACATAG AGCGAAGCTA
CAAGAACAAT ATTTGTGGAC GCAAGTTGAT TTTAAATCCG AAGGTGAAAA TGATCTATCT AATAAGGCTC TTAAGGCTGC
AACCAAACTC AAGGGATGCG GTCAATTTCT CTTATTCCAT AATTACTACA CAATAGACCA AGTTAAACTT GCTAAGGCCT
ATTACTGTTC TCAGCATTTG CTATGTCCTA TGTGTGCTGG TGTAAGGGCT GCTAAGTCAA TGAGTCGTTA TATTCAGCGT
ATTGAAGAAC TAATGCGCCA GAATCGCCAT TTAAAGCCCG TCCTGATCAC TTTGACGGTA AAGAATGGCC CTGACCTACA
AGAACGCTTC AAACACCTTA GAGCATCATT TAGAACGCTT TTAGATCGTT ATAACGATTA CAAGAAAAAA GGTCGTGGTT
TTAATCAGTT TTGTAAAATT GATGGTGCTT TTTATTCAAC TGAATATACA TACAATCCAA AAACTAAAGA ATGGCATCCG
CATATTCATA TTTTTGCCTT ACTCAATCAA TGGATAGACC AGGAAGAATT GTCCGAAACT TGGCACGATA TTACTCTGGA
TTCTTATATC GTCGATATTC GTAGAGTTAA AAAAACCAAA GAACACGGCT ATAGCAAAGC TGTTGCTGAG GTATGTAAAT
ACGCCCTTAA GTTAGTGAT CTCTCACTGG AGAACACTTG GGAGGCATAT CTTTCTTTGA AAGGTAACAG GCTTACTGGC
TGTTTTGGTT CTATGTATGG TGTCAAATTG CCTGAAAAAC TTACTGATGA TCTACCCCTT GATGATCTTC CATATTTGGA
GCTGTTATAC CGTTTTGTTT TTGGTAAAAA ATCTTATTAC AACCTAGAAA TAACAAAAGA CGTAAAGCCA CAAAACTAGG
ACTACAACGA TGAGGTGAGG GCGACGCGCG ACCGTGCGCG CTACTTCGTG CATGTACGCG CGCGCCTTTG CCTCTTTGTT
GCGAGGTGTG GACGAAAAAA GCAAGGATAC ATACAGACCC CTGCATGACC TTGTAAGGGG TTCGACCCCT TAGACCCCAA
AGGGCGCACT TATGCAAACT CTTCGAGTTC GCCAGTGCTC CCACCAGTAA CAGAGGGCGC GGAGTGCGCC CGAACTGACG
CTATAGAATT C
```

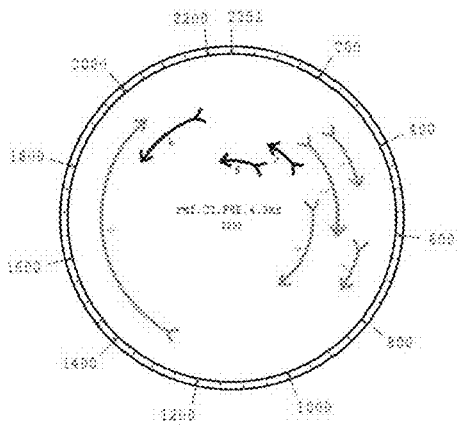

86% nucleotide similarity to Sphinx2.36 (2364 bp) in 845nt overlap

Putative ORFs:

| | | |
|---|---|---|
| 229 amino acids | 82% similarity to Sphinx2.36 (232 aa) | Replication protein |
| 96 amino acids | 91% similarity to Sphinx2.36 (96 aa) | Function unknown |
| 111 amino acids | 97% similarity to Sphinx2.36 (124 aa) | Function unknown |

FIGURE 1B 229 amino acids    82% similarity to Sphinx2.36 (232 aa)    Replication protein

```
                       1                                                     50
SPHINX2.36.232.PEP    MQEQYLWTQV DFKVGSETSI KALKAATKLK GCGQFLLFRN YYTIDQIKLE
HCBI1.225.229.pep    ~~~~~~~~~~ ~~~~~~~~~~ ~~~~~~~~~~ ~~~~~~~~~~ ~~~~~~~~~~
                       51                                                   100
SPHINX2.36.232.PEP    KFHVCGQHLL CPMCAGIRAA RSMNRYIQRI EEIMRQNRKL KPVLITLTVK
HCBI1.225.229.pep    ~~~~~~~~~~ ~~MCAGVRAA KSMSRYIQRI EELMRQNRHL KPVLITLTVK
                      101                                                   150
SPHINX2.36.232.PEP    NGEDLQERFE HLTGSFKTLL QRYRDFKKKG RGFNQFCKID GGFYTTEYTY
HCBI1.225.229.pep    NGPDLQERFK HLRASFRTLL DRYMDYKKKG RGFNQFCKID GAFYSTEYTY
                      151                                                   200
SPHINX2.36.232.PEP    NETTQQWHPH IHIFALVTDR IDQEELAETW HDITLDSYIV DIRRVKKTKE
HCBI1.225.229.pep    NPKTKEWHPH IHIFALLNQW IDQEELSETW HDITLDSYIV DIRRVKKTKE
                      201                                                   250
SPHINX2.36.232.PEP    HGYAKAVAEV CKYALKFSDL STEKTFQAFF DP~~~~~~~~ ~~~~~~~~~~
HCBI1.225.229.pep    HGYSKAVAEV CKYALKFSDL SLEMTWEAYL SLKGNRLTGC FGSMYGVKLP
                      251                                    291
SPHINX2.36.232.PEP    ~~~~~~~~~~ ~~~~~~~~~~ ~~~~~~~~~~ ~~~~~~~~~~ ~
HCBI1.225.229.pep    EKLTDDLPLD DLPYLELLYR FVFGKKSYYN LEITKDVKPQ N
```

96 amino acids    91% similarity to Sphinx2.36 (96 aa)    Function unknown

```
                       1                                                     50
SPHINX2.36.96.PEP    ~~~~~~~~~~ ~~~~~~~~~~ ~~~~~~~~~~ ~MINLQGTLI NAFRLDGGKG
HCBI1.225.127.pep    MMKQLKLFLK LKPQSLRISM LQEKLNQGIN QMINLQGTLI NAFRVDGGKG
                       51                                                   100
SPHINX2.36.96.PEP    KDGKEYEARD KVQILGSLEL PNGEIKHELV DLTVEDARIF EPFKHKVISI
HCBI1.225.127.pep    KDGKEYEARD KVQILGSLEL PNGEIKHELV DLTVEDSRLF EPFKNQVISI
                      101              127
SPHINX2.36.96.PEP    SCGAMAIGRN VVFYVRKGAK PVLADVM
HCBI1.225.127.pep    SCGAMAVGRN VIFYVRKGAK PVLAEQM
```

111 amino acids    97% similarity to Sphinx2.36 (124 aa)   Function unknown

```
                       1                                                     50
SPHINX2.36.124.PEP   MNHKLIAIDQ ELTMKLHNPN PNEPTNLQML VAEIKKSASS SYHGGYIQVP
HCBI1.225.111.pep    ~~~~~~~~~~ ~~~MKLHNPN PNEPTNLQML VAEVKKSASS SYHGGYIQVP
                       51                                                   100
SPHINX2.36.124.PEP   FRVECASYTR LEALVKHTGS SRNKIMNDLL RIGIETLAAS LDDETIKTLF
HCBI1.225.111.pep    FRVEFASYTR LEALVKHTGS SRNKIMNDLL RIGIETLAAS LDDETIKTLF
                      101                124
SPHINX2.36.124.PEP   EIETSITADL YASGKMKSGD QSDD
HCBI1.225.111.pep    EIETSITADL YASGKIKSGD QSDD
```

*FastA *Geall*

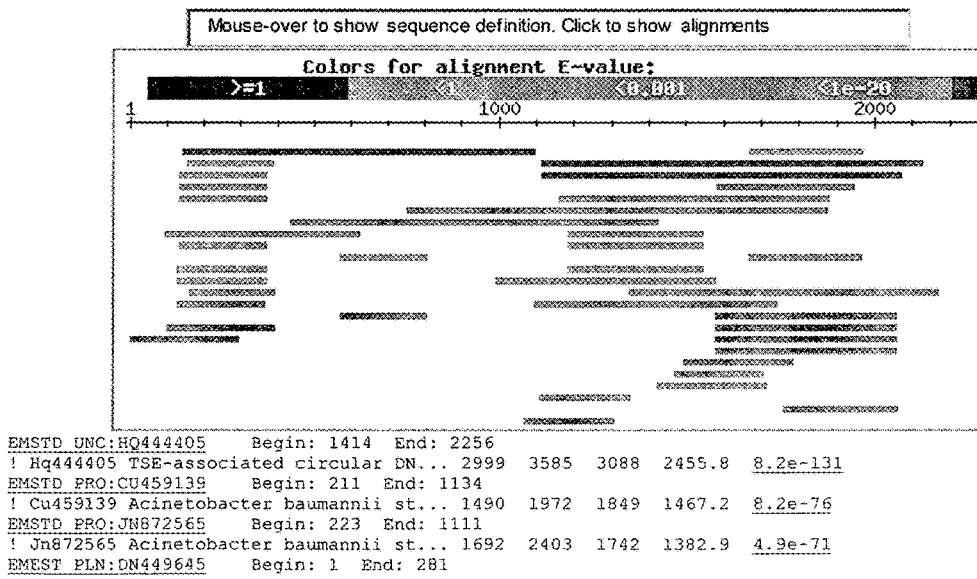

```
EMSTD_UNC:HQ444405    Begin: 1414  End: 2256
! Hq444405 TSE-associated circular DN...  2999  3585  3088  2455.8   8.2e-131
EMSTD_PRO:CU459139    Begin: 211   End: 1134
! Cu459139 Acinetobacter baumannii st...  1490  1972  1849  1467.2   8.2e-76
EMSTD_PRO:JN872565    Begin: 223   End: 1111
! Jn872565 Acinetobacter baumannii st...  1692  2403  1742  1382.9   4.9e-71
EMEST_PLN:DN449645    Begin: 1     End: 281
```

FIGURE 1C

```
! Dn449645 EST945444 Sequencing ESTs ...  665   665   712   572.5  5.3e-25

EMSTD_UNC:HQ444405
ID    HQ444405; SV 1; circular; genomic DNA; STD; UNC; 2364 BP.
AC    HQ444405;
DE    TSE-associated circular DNA isolate Sphinx 2.36, complete sequence.
SCORES    z-score: 2455.8 E(): 8.2e-131
>>EMSTD_UNC:HQ444405                                              (2364 nt)
  85.7% identity in 845 nt overlap
  (175-1011:1414-2256)
                 150       160       170       180       190       200
rmf.C2.F8E.4 GAGTGCCGCATCACTCAATCTATCAAGTGCCGCATCACCTGATTACTCA-AATCTACATG
                ||||   |  | ||||||  ||  ||| ||
HQ444405     ATAATTTGCGGTCACTGTGCCGAATCACTACGCAATATTTTATTACCCATAATTTAACCA
                1390      1400      1410      1420      1430      1440

210       220       230       240       250       260
rmf.C2.F8E.4 AAATTTTCTTTCTTGCAAACGGTTCAGAAAAGCATTATAAATATCCCACCAATGAATCAT
              |  ||  |||||||||||||||||||||| ||||||||||||||| |||||||||||||||
HQ444405     ATTCTTAATTTCTTGCAAACGGTTCAAAAAAGCATTATAAATATCTCACCAATGAATCAT
                1450      1460      1470      1480      1490      1500

270       280       290       300       310       320
rmf.C2.F8E.4 AAATGAATCACTATAGATCAGGAAACAACTATGAAACTCCATAATCCAAATCCAAATGAG
              |||   ||||  |||||||||||||  |||||||||||||||||||||||||||||||||||
HQ444405     AAACTAATCGCTATAGATCAGGAATTAACTATGAAACTCCATAATCCAAATCCAAATGAG
                1510      1520      1530      1540      1550      1560

330       340       350       360       370       380
rmf.C2.F8E.4 CCTACTAACCTACAAATGCTTGTTGCAGAAGTTAAAAAATCCGCTTCAAGCTCTTATCAC
              |||||||||||  |||||||||||||||||||  ||||||||||||||||||||||||||||||||
HQ444405     CCTACTAACCTGCAAATGCTTGTTGCAGAAATTAAAAAATCCGCTTCAAGCTCTTATCAC
                1570      1580      1590      1600      1610      1620

390       400       410       420       430       440
rmf.C2.F8E.4 GGTGGTTATATTCAAGTTCCTTTCCGTGTTGAGTTTGCATCATATACACGCCTTGAGGCA
              |||||  ||||||||||||||||||||||||||||| |||||||||||||||||||||||  |||
HQ444405     GGTGGCTATATTCAAGTTCCTTTCCGTGTTGAGTGTGCATCATATACACGCCTTGAAGCA
                1630      1640      1650      1660      1670      1680

450       460       470       480       490       500
rmf.C2.F8E.4 CTTGTTAAACATACTGGCTCAAGTCGCAATAAGATCATGAATGATCTGTTAAGAATCGGT
              ||||||||||||||||||||||||||||||||||||||||||||||||||||  ||||||||||||
HQ444405     CTTGTTAAACATACTGGCTCAAGTCGCAATAAGATCATGAATGATCTCTTAAGAATCGGT
                1690      1700      1710      1720      1730      1740

510       520       530       540       550       560
rmf.C2.F8E.4 ATTGAAACTCTAGCTGCCTCTTTGGATGATGAAACAATTAAAACTCTTTTTGAAATTGAA
              |||||||||||||||||||||||||||  ||  |||||||||||||||||||||||||||||
HQ444405     ATTGAAACTCTAGCTGCCTCTTTGGACGACGAAACAATTAAAACTCTTTTTGAAATTGAA
                1750      1760      1770      1780      1790      1800

570       580       590       600       610       620
rmf.C2.F8E.4 ACCTCAATCACTGCGGATCTCTATGCTTCAGGAAAAATTAAATCAGGGGATCAATCAGAT
              || |||||||||||||||||||||||||||||||||||  ||||||||| |||||  ||||||
HQ444405     ACTTCAATCACTGCGGATCTCTATGCTTCAGGAAAAATGAAATCAGGAGATCAGTCAGAT
                1810      1820      1830      1840      1850      1860

630       640       650       660       670       680
rmf.C2.F8E.4 GATTAATTTACAAGGAACTCTAATTAATGCTTTTCGTGTGGATGGTGGTAAAGGTAAAGA
              ||||||||||||||  ||  || ||  |||||||||||| |  ||||||||||||||||  ||||
HQ444405     GATTAATTTACAAGGGACACTTATAAATGCTTTTCGTCTTGATGGTGGTAAAGGGAAAGA
                1870      1880      1890      1900      1910      1920

690       700       710       720       730       740
rmf.C2.F8E.4 CGGCAAAGAATATGAAGCGCGTGACAAGGTGCAAATTCTTGGTTCGTTGGAGTTACCCAA
              ||||||||||||||||| ||||||||||||||||||||||||||||  |||||||  |||||
HQ444405     CGGCAAAGAATATGAAGCACGTGACAAGGTGCAAATTCTTGGTTCGCTGGAGTTGCCCAA
                1930      1940      1950      1960      1970      1980

750       760       770       780       790       800
rmf.C2.F8E.4 TGGGGAAATTAAACACGAACTTGTTGACCTAACAGTTGAGGATTCTCGACTTTTTGAACC
              || || ||  || | ||||  ||  ||||| |||| |||  |||  || |||||||||| ||
HQ444405     CGGTGAGATCAAACATGAGCTTGTTGACTTAACGGTTGAAGATGCTCGCATCTTTGAGCC
                1990      2000      2010      2020      2030      2040

810       820       830       840       850       860
rmf.C2.F8E.4 ATTCAAAAATCAGGTTATTAGCATCTCATGTGGTGCTATGGCTGTCGGTCGTAATGTTAT
              ||||||| |  |||| |||||||||| ||||| ||||||||||||| ||||||||||  |
```

FIGURE 1D

```
HQ444405    ATTCAAACACAAGGTAATTAGCATTTCATGCGGTGCTATGGCTATCGGTCGAAATGTTGT
                2050      2060      2070      2080      2090      2100

870       880       890       900       910       920
rmf.C2.F8E.4 TTTTTATGTTCGCAAAGGCGCAAAACCAGTTTTAGCAGAACAAATGTGAAACCCGAAAAA
             |||||||||||| ||||| ||||| || |||||||||||  |||||  || |   |||
HQ444405     TTTTTATGTTCGAAAAGGTGCAAAGCCTGTTTTAGCAGATGTAATGT--AATTCATGAAA
                2110      2120      2130      2140      2150      2160

930       940       950       960       970
rmf.C2.F8E.4 AAAAACAGTGAGTTA-GCGAAGCAACTCGATACTATTGATTAACTAGGGGACAA------
             ||||||||||||||| ||   ||||| | ||| ||   |      |   ||  |
HQ444405     AAAAACAGTGAGTTAGGCTTGCCGACTCGCTGTTTTTTCTTTTACTTGATACTATTAACT
                2170      2180      2190      2200      2210      2220

980       990      1000      1010      1020      1030
rmf.C2.F8E.4 AAATTGACTATAAAAGACAATAAAAAAGCCCATAATTCGGATGCTTTGGCGGGCGATGAA
             ||| ||   | ||||    |  ||||||||| || || ||||
HQ444405     AAAGTGGGGACAAAATTGACTAAAAAAGACAATAAAAAAGCCCATAATTCTGATGCTTTG
                2230      2240      2250      2260      2270      2280 rmf.C2.F8E.4.3kr.seq
EMSTD_PRO:CU459139
ID   CU459139; SV 1; circular; genomic DNA; STD; PRO; 2726 BP.
AC   CU459139;
DE   Acinetobacter baumannii str. AYE plasmid p4ABAYE, complete genome.   .   .   .
SCORES   z-score: 1467.2 E(): 8.2e-76
>>EMSTD_PRO:CU459139                                              (2726 nt)
 67.1% identity in 926 nt overlap
 (1143-2064:211-1134)
                1120      1130      1140      1150      1160      1170
rmf.C2.F8E.4 CGAAGCTACAAGAACAATATTTGTGGACGCAAGTTGATTTTAAATCCGAAGGTGAAAATG
                                        |||   ||| | |  ||||  |   |||| |
CU459139     AAAACTATTTATTTTCGTTAGCTAAGATTAAAGAAAATTATCATGCCGATGTAAAAAACG
                 190       200       210       220       230       240

1180      1190      1200      1210      1220      1230
rmf.C2.F8E.4 ATCTATCTAATAAGGCTCTTAAGGCTGCAACCAAACTCAAGGGATGCGGTCAATTTCTCT
             ||  ||||| |   || | || ||||       |||  | || || ||||||| |||||
CU459139     ATGAATCTATTCGCGCCATGAAAACTGCCCAAAAATTAAATGGGTGCGGTAATTTTCTTC
                 250       260       270       280       290       300

1240      1250      1260      1270      1280      1290
rmf.C2.F8E.4 TATTCCATAATTACTACACAATAGACCAAGTTAAACTTGCTAAGGCCTATTACTGTTCTC
             ||||| | ||||  ||||| ||  | |||  ||||||| ||  ||   |||   |||  |
CU459139     TATTCAAAAATTTTTACACCATTAATCAAATTAAACTCGCCAAGTTCCAAGCTTGTAGTG
                 310       320       330       340       350       360

1300      1310      1320      1330      1340      1350
rmf.C2.F8E.4 AGCATTTGCTATGTCCTATGTGTGCTGGTGTAAGGGCTGCTAAGTCAATGAGTCGTTATA
             |||||||  |||||| | ||||||||||| | |||| ||||||| ||||| ||    ||
CU459139     AGCATTTGTTATGTCCGTTTTGTGCTGGTATTAGAGCTTCTAAGGCAATTCAAAAATACT
                 370       380       390       400       410       420

1360      1370      1380      1390      1400      1410
rmf.C2.F8E.4 TTCAGCGTATTGAAGAACTAATGCGCCAGAATCGCCATTTAAAGCCCGTCCTGATCACTT
             | ||||| ||||  || |    |  |||| | |||||||||||||||||  ||||| | |
CU459139     CTGAGCGTGTTGATCAAGTCTTATCTGAAAATCCTCGTTTAAAGCCCGTTATGATCACGT
                 430       440       450       460       470       480

1420      1430      1440      1450      1460      1470
rmf.C2.F8E.4 TGACGGTAAAGAATGGCCCTGACCTACAAGAACGCTTCAAACACCTTAGAGCATCATTTA
             |  ||||| || |||||     |||||   ||||| |||| || ||| |  ||| ||||
CU459139     TTACGGTTAAAAATGGGGTAGACCTAGGGGAACGGTTCACCCATCTTATAAAATCGTTTA
                 490       500       510       520       530       540

1480      1490      1500      1510      1520      1530
rmf.C2.F8E.4 GAACGCTTTTAGATCGTTATAACGATTACAAGAAAAAAGGTCGTGGTTTTAATCAGTTTT
             ||||||| |||| || || || ||  | ||  |||||||||||||| ||||||| ||||
CU459139     GAACGCTTATAGAGCGTCGTAGGGACTATATTAAAAAAGGGCGTGGCTTTAATGAATTTT
                 550       560       570       580       590       600

1540      1550      1560      1570      1580      1590
rmf.C2.F8E.4 GTAAAATTGATGGTGCTTTTTATTCAACTGAATATACATACAATCCAAAAACTAAAGAAT
             | ||||||  |||||| ||| ||||| ||| | |||| | |||||||||||| |||||
CU459139     GCAAAATTAATGGTGCGATGTATTCATATGAGAATACTTACAATGAAAAAACTAATGAAT
                 610       620       630       640       650       660

```
rmf.C2.F8E.4 GGCATCCGCATATTCATATTTTTGCCTTACTCAATCAATGGATAGACCAGGAAGAATTGT
             ||||||| ||||||||||| |||||  |  |  ||  | ||||||||  |||||  |||||||
CU459139     GGCATCCTCATATTCATATGTTTGCACTTTTGGATGATTGGATAGATCAGGATGAATTGT
                 670       680       690       700       710       720

1660      1670      1680      1690      1700      1710
rmf.C2.F8E.4 CCGAAACTTGGCACGATATTACTCTGGATTCTTATATCGTCGATATTCGTAGAGTTAAAA
             |  ||  ||||||  ||||||  ||| |||   |||     ||||  ||||||||||||| ||||
CU459139     CTCAATATTGGCAATCCATTACTGGGGACTCTATGGTCGTTGATATTCGTAGAGCCAAAA
                 730       740       750       760       770       780

1720      1730      1740      1750      1760      1770
rmf.C2.F8E.4 AAACCAAAGAACACGGCTATAGCAAAGCTGTTGCTGAGGTATGTAAATACGCCCTTAAGT
             ||   |||||    ||||||       |||| ||||||  ||  ||||||||  ||  ||  |
CU459139     AACAAAAAGACTTAGGCTATTCAGGTGCTGCTGCTGAAGTCTGTAAATATGCTCTCAAAT
                 790       800       810       820       830       840

1780      1790      1800      1810      1820      1830
rmf.C2.F8E.4 TTAGTGATCTCTCACTGGAGAACACTTGGGAGGCATATCTTTCTTTGAAAGGTAACAGGC
             || |||||||| || | || ||||||||||| || |  ||||||||||||  |
CU459139     TTGGTGATCTTTCTGTAGAAAAGACTTGGGAAGCTTTCAAAGTTTTGAAAGGTAAGCGAT
                 850       860       870       880       890       900

1840      1850      1860      1870      1880      1890
rmf.C2.F8E.4 TTACTGGCTGTTTTGGTTCTATGTATGGTGTCAAATTGCCTGAAAAACTTACTGATGATC
             | | |||   ||||||| ||| |  || || ||| |  |||||||  |  |  |  ||||||
CU459139     TAAGTGGGGCTTTTGGATCTCTTTGGGCGTGAAAATTCCTGAATCATTGATAGATGATC
                 910       920       930       940       950       960

1900      1910      1920      1930      1940
rmf.C2.F8E.4 TACC---CCTTGATGATCTTCCATATTTGGAGCTGTTATACCGTTTTGTTTTGGTAAAA
             | ||    |  | ||||| | || |||||  ||  || || |  || |||  |||  ||| |
CU459139     TTCCAGACGATTCTGATTTACCTTATTTAGAAATGATTTATAAGTTCGTCTTTTCTAAGA
                 970       980       990       1000      1010      1020

1950      1960      1970      1980      1990      2000
rmf.C2.F8E.4 AATCTTATTACAACCTAGAAATAACAAAAGACGTAAAGCCACAAAACTAGGACTACAACG
             | |||||||||  ||  || || | ||      | || | ||    |  |||||  ||  ||
CU459139     AGTCTTATTACGATTTACAACTTACTCGTCATGTCGAACCTACAGGTAAGGACGACGCCG
                 1030      1040      1050      1060      1070      1080

2010      2020      2030      2040      2050      2060
rmf.C2.F8E.4 ATGAGGTGAG-GGCGACGCGCGACCGTGCGCGCTACTTCGTGCATGTACGCGCGCGCCTT
             | ||| |  | || || |   |||    |  | |  |  | |||||  |||  |||  |||
CU459139     ACGAGCTTCGAGGAGAAGAAGGACGCAACCTGTTGGT--GAGCATGGACGGGCGAGGAGC
                 1090      1100      1110      1120      1130 rmf.C2.F8E.4.3kr.seq
EMSTD_PRO:JN872565
ID   JN872565; SV 1; circular; genomic DNA; STD; PRO; 2252 BP.
AC   JN872565;
DE   Acinetobacter baumannii strain DS002 plasmid pTS236, complete sequence.
SCORES    z-score: 1382.9 E(): 4.9e-71
>>EMSTD_PRO:JN872565                                          (2252 nt)
  66.4% identity in 889 nt overlap
  (1143-2030:223-1111)
                 1120      1130      1140      1150      1160      1170
rmf.C2.F8E.4 CGAAGCTACAAGAACAATATTTGTGGACGCAAGTTGATTTTAAATCCGAAGGTGAAAATG
                                                |||   |  |  |  ||   |  |  ||||| |
JN872565     AAAATTATTTATTTACCCTGGCTAAGTTTAAAGAGAACTATGAAAAAGACGTTAAAAACG
                 200       210       220       230       240       250

1180      1190      1200      1210      1220      1230
rmf.C2.F8E.4 ATCTATCTAATAAGGCTCTTAAGGCTGCAACCAAACTCAAGGGATGCGGTCAATTTCTCT
             |   |||||  |||||||| ||  ||||      |||  |  || ||||||||  |  |||
JN872565     AAGAATCTATCAAGGCTCTAAAAATCTGCTCAGAAATTGAATGAATGCGGAAACTATCTGC
                 260       270       280       290       300       310

1240      1250      1260      1270      1280      1290
rmf.C2.F8E.4 TATTCCATAATTACTACACAATAGACCAAGTTAAACTTGCTAAGGCCTATTACTGTTCTC
             ||||  |  ||||  ||||||||||  |  ||||||||    |||      |||       |
JN872565     TATTCAAAAATTTTTACACAATAGGCGAAGTTAAACTCTCCAAGCTCCGCACCTGCGGAC
                 320       330       340       350       360       370

1300      1310      1320      1330      1340      1350
rmf.C2.F8E.4 AGCATTTGCTATGTCCTATGTGTGCTGGTGTAAGGGCTGCTAAGTCAATGAGTCGTTATA
             ||||||||||| ||| |||| |||||||   |    | ||| ||    | ||        ||
JN872565     AGCATTTGCTTTGCCCTTTCTGTGCTGCCATTCGTGCTTCTCGTGCTATCCAAAAATACG
                 380       390       400       410       420       430
```

FIGURE 1F

```
              1360       1370       1380       1390       1400       1410
rmf.C2.F8E.4  TTCAGCGTATTGAAGAACTAATGCGCCAGAATCGCCATTTAAAGCCCGTCCTGATCACTT
              || | ||||||||  || |  |||   | ||||||| |  | ||||||||| || |||||
JN872565      TTGAACGTATTGATCAAGTCCTGCAAGAAAATCGCAAGCTCAAGCCCGTTCTAATCACGC
               440        450        460        470        480        490

1420       1430       1440       1450       1460       1470
rmf.C2.F8E.4  TGACGGTAAAGAATGGCCCTGACCTACAAGAACGCTTCAAACACCTTAGAGCATCATTTA
              | || || || || || ||| |||||||||  ||||||||  | |||| ||||   ||||
JN872565      TCACCGTTAAAAACGGCTCTGACCTAGCAGAACGCTCCGAACATCTTATGAAGTCCTTTA
               500        510        520        530        540        550

1480       1490       1500       1510       1520       1530
rmf.C2.F8E.4  GAACGCTTTTAGATCGTTATAACGATTACAAGAAAAAAGGTCGTGGTTTTAATCAGTTTT
              |||||||  ||||  |||  |||  || ||  | || |||||||| |||||||| |||| |
JN872565      GAACGCTCCTAGAGCGTCGTAGGGACTATGAAAAGAAAGGTCGAGGTTTTAATGAGTTCT
               560        570        580        590        600        610

1540       1550       1560       1570       1580       1590
rmf.C2.F8E.4  GTAAAATTGATGGTGCTTTTTATTCAACTGAATATACATACAATCCAAAAACTAAAGAAT
              ||||  ||  |  ||  ||| |  ||   ||||  |||||  |||||  ||| ||||
JN872565      GTAAGGTTCAAGGGGCTATGTACTCCTATGAAAATACATTCAATGAAAAAACAGGCGAAT
               620        630        640        650        660        670

1600       1610       1620       1630       1640       1650
rmf.C2.F8E.4  GGCATCCGCATATTCATATTTTTGCCTTACTCAATCAATGGATAGACCAGGAAGAATTGT
              |||||||||||||||||||| || ||| || ||  | ||||||||| || ||| |||| || |
JN872565      GGCATCCGCATATTCATATGTTCGCTTTGGTTGATCAATGGATTGATCAGCAAGAGTTTT
               680        690        700        710        720        730

1660       1670       1680       1690       1700       1710
rmf.C2.F8E.4  CCGAAACTTGGCACGATATTACTCTGGATTCTTATATCGTCGATATTCGTAGAGTTAAAA
              | |||  ||||||   |||||| ||| ||   | |||||||||| || ||  | ||||
JN872565      CAGAATATTGGCATAGCCTTACTGGGGACTCGATGGTTGTCGATGTCCGCAGGGCAAGAA
               740        750        760        770        780        790

1720       1730       1740       1750       1760       1770
rmf.C2.F8E.4  AAACCAAAGAACACGGCTATAGCAAAGCTGTTGCTGAGGTATGTAAATACGCCCTTAAGT
              ||   ||||   |||| |||||||||||||| ||| || || |||||  || ||  | ||||
JN872565      AAGAAAAAGGTTACGGTTATAGCAAAGCGGCTGCCGAAGTCTGTAAGTATGCTTTGAAGT
               800        810        820        830        840        850

1780       1790       1800       1810       1820       1830
rmf.C2.F8E.4  TTAGTGATCTCTCACTGGAGAACACTTGGGAGGCATATCTTTCTTTGAAAGGTAACAGGC
              || ||||||| | ||||  || ||  ||||||  ||||   ||| |  | || || ||| |||
JN872565      TTGGTGATCTGTCCGTTGAAAAGACTTGGGAAGCATTTAAGGTTCTTAAGGGAAAGCGTT
               860        870        880        890        900        910

1840       1850       1860       1870       1880       1890
rmf.C2.F8E.4  TTACTGGCTGTTTTGGTTCTATGTATGGTGTCAAATTGCCTGAAAAACTTACTGATGATC
              | || || | ||||||||     | | |||||||||| | |||||     | || || || |||
JN872565      TAACAGGTTCTTTTGGTCTGCTATGGGGTGTCAAAATCCCTGACTCAATGACAGACGATA
               920        930        940        950        960        970

1900       1910       1920       1930       1940       1950
rmf.C2.F8E.4  TACCCCTTGATGATCTTCCATATTTGGAGCTGTTATACCGTTTTGTTTTGGTAAAAAAT
              |  ||    || ||  | |||||| |   ||| |||     | ||  | |||||| |
JN872565      TGCCATCAGAAGACTTGCCATATCTCGAAATGCTGTACAAGTTTGCCTACAGTAAAAAGT
               980        990       1000       1010       1020       1030

1960       1970       1980       1990       2000       2010
rmf.C2.F8E.4  CTTATTACAACCTAGAAATAACAAAAGACGTAAAGCCACAAAACTAGGACTACAACGATG
              ||||  |||  ||  || |||||||  |  ||||| |||||||||  |  ||| |  ||
JN872565      CTTACTACGACTTACTAATCACAAGGCACGTAGAGCCACAACCGCATGAGGACGAGCGTG
               1040       1050       1060       1070       1080       1090

2020       2030       2040       2050       2060       2070
rmf.C2.F8E.4  AGGTGAG-GGCGACGCGCGACCGTGCGCGCTACTTCGTGCATGTACGCGCGCGCCTTTGC
              |  |||    ||||| | |  |
JN872565      CGAGGAGCTTCGACGAGTGCGATTGTATTTATGCGGTGGAGGCTCAGACGTTTGACTGTG
               1100       1110       1120       1130       1140       1150
```

*BlastN2:*

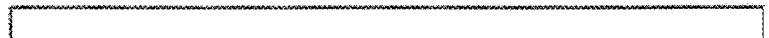

FIGURE 1G

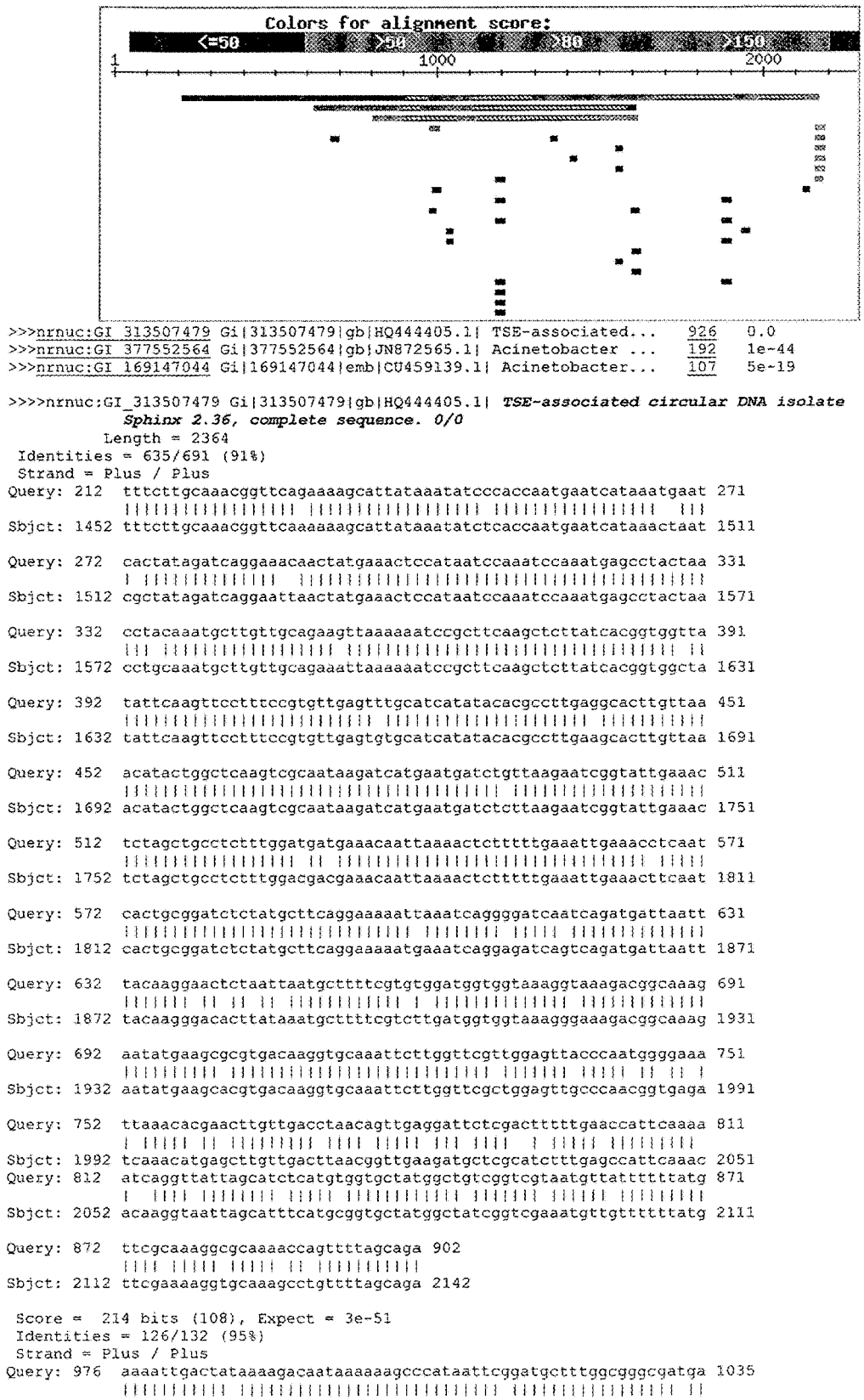

```
>>>nrnuc:GI_313507479  Gi|313507479|gb|HQ444405.1| TSE-associated...    926   0.0
>>>nrnuc:GI_377552564  Gi|377552564|gb|JN872565.1| Acinetobacter ...    192   1e-44
>>>nrnuc:GI_169147044  Gi|169147044|emb|CU459139.1| Acinetobacter...    107   5e-19

>>>>nrnuc:GI_313507479 Gi|313507479|gb|HQ444405.1| TSE-associated circular DNA isolate
         Sphinx 2.36, complete sequence. 0/0
         Length = 2364
 Identities = 635/691 (91%)
 Strand = Plus / Plus
Query: 212   tttcttgcaaacggttcagaaaagcattataaatatcccaccaatgaatcataaatgaat 271
             ||||||||||||||||||| ||||||||||||||||| |||||||||||||||| |||
Sbjct: 1452  tttcttgcaaacggttcaaaaaagcattataaatatctcaccaatgaatcataaactaat 1511

Query: 272   cactatagatcaggaaacaactatgaaactccataatccaaatccaaatgagcctactaa 331
             | ||||||||||||||  |||  |||||||||||||||||||||||||||||||||||
Sbjct: 1512  cgctatagatcaggaattaactatgaaactccataatccaaatccaaatgagcctactaa 1571

Query: 332   cctacaaatgcttgttgcagaagttaaaaaatccgcttcaagctcttatcacggtggtta 391
             ||| ||||||||||||||||||| |||||||||||||||||||||||||||||||| ||
Sbjct: 1572  cctgcaaatgcttgttgcagaaattaaaaaatccgcttcaagctcttatcacggtggcta 1631

Query: 392   tattcaagttcctttccgtgttgagtttgcatcatatacacgccttgaggcacttgttaa 451
             |||||||||||||||||||||||||| |||||||||||||||||||| |||||||||||
Sbjct: 1632  tattcaagttcctttccgtgttgagtgtgcatcatatacacgccttgaagcacttgttaa 1691

Query: 452   acatactggctcaagtcgcaataagatcatgaatgatctgttaagaatcggtattgaaac 511
             |||||||||||||||||||||||||||||||||||||||| ||||||||||||||||||
Sbjct: 1692  acatactggctcaagtcgcaataagatcatgaatgatctcttaagaatcggtattgaaac 1751

Query: 512   tctagctgcctctttggatgatgaaacaattaaaactcttttgaaattgaaacctcaat 571
             ||||||||||||||||| || ||||||||||||||||||||||||||||||| | |||
Sbjct: 1752  tctagctgcctctttggacgacgaaacaattaaaactcttttgaaattgaaacttcaat 1811

Query: 572   cactgcggatctctatgcttcaggaaaaattaaatcaggggatcaatcagatgattaatt 631
             |||||||||||||||||||||||||||||| |||||||| ||||| ||||||||||||
Sbjct: 1812  cactgcggatctctatgcttcaggaaaaatgaaatcaggagatcagtcagatgattaatt 1871

Query: 632   tacaaggaactctaattaatgcttttcgtgtggatggtggtaaaggtaaagacggcaaag 691
             ||||||  ||  || || |||||||||| | |||||||||||||| ||||||||||||
Sbjct: 1872  tacaagggacacttataaatgcttttcgtcttgatggtggtaaagggaaagacggcaaag 1931

Query: 692   aatatgaagcgcgtgacaaggtgcaaattcttggttcgttggagttacccaatggggaaa 751
             ||||||||| | ||||||||||||||||||||||||||| | |||| || || || |
Sbjct: 1932  aatatgaagcacgtgacaaggtgcaaattcttggttcgctggagttgcccaacggtgaga 1991

Query: 752   ttaaacacgaacttgttgacctaacagttgaggattctcgacttttttgaaccattcaaaa 811
             | ||||| || ||||||||| ||| |||| |||| || |||  ||||| ||||||||||
Sbjct: 1992  tcaaacatgagcttgttgacttaacggttgaagatgctcgcatctttgagccattcaaac 2051
Query: 812   atcaggttattagcatctcatgtggtgctatggctgtcggtcgtaatgttatttttttatg 871
             |  || |||||||||| |||||||||||||||||| |||||| |||||||||||| ||||
Sbjct: 2052  acaaggtaattagcatttcatgcggtgctatggctatcggtcgaaatgttgttttttatg 2111

Query: 872   ttcgcaaaggcgcaaaaccagttttagcaga 902
             |||| ||||| ||||| || ||||||||||
Sbjct: 2112  ttcgaaaaggtgcaaagcctgttttagcaga 2142

Score =  214 bits (108), Expect = 3e-51
 Identities = 126/132 (95%)
 Strand = Plus / Plus
Query: 976   aaaattgactataaaagacaataaaaaagcccataattcggatgctttggcgggcgatga 1035
             |||||||||| ||||||||||||||||||||||||||||||| ||||||||||||| ||
```

FIGURE 1H

```
Sbjct:  2233  aaaattgactaaaaaagacaataaaaaagcccataattctgatgctttggcgggcgacga  2292

Query:  1036  attacaggctttgcaatctgctaaggcagatcaacacagggatagaataacacgttttgg  1095
              |||||||||||||||||||||||||| |||||||||||||||||||||| ||||||||||
Sbjct:  2293  attacaggctttgcaatctgctaatgcagatcaacacagggatagaatatcacgttttgg  2352

Query:  1096  aattttgaaaca  1107
              | |||||||||||
Sbjct:  2353  actttgaaaca  2364

Score =  143 bits (72),  Expect = 9e-30
 Identities = 303/380 (79%)
 Strand = Plus / Plus
Query:  1292  cagcatttgctatgtcctatgtgtgctggtgtaagggctgctaagtcaatgagtcgttat  1351
              ||||||||||||||||||| |||||||||||| |  | |||||   ||||||| ||| |||
Sbjct:  180   cagcatttgctatgtccaatgtgtgctggtattcgtgctgcccgttcaatgaatcggtat  239

Query:  1352  attcagcgtattgaagaactaatgcgccagaatcgccatttaaagcccgtcctgatcact  1411
              ||||| || || |||||| ||||||| |||||||||| |||||| |||||||||||||||
Sbjct:  240   attcaacgcatcgaagaaataatgcgtcagaatcgcaagctaaagcccgtattgatcact  299

Query:  1412  ttgacggtaaagaatggccctgacctacaagaacgcttcaaacacccttagagcatcattt  1471
              ||||| || |||||  ||    ||||||||||| |||||||| |||||| |||| |||| |
Sbjct:  300   ttgaccgttaagaacggtgaagacctacaggaacgctttgaacacctcacaggctcattt  359

Query:  1472  agaacgcttttagatcgttataacgattacaagaaaaaggtcgtggttttaatcagttt  1531
              |  |||||||| | ||||    ||||  |||||||||||  |||  |||||||| |||| |
Sbjct:  360   aagacgcttttacagcgttaccgtgattttaagaaaaagggtcgagggtttaatcaatttt  419

Query:  1532  tgtaaaattgatggtgctttttattcaactgaatatacatacaatccaaaaactaaagaa  1591
              || ||||||||||| | ||||| ||||| | || |||| |||||   ||  ||  || ||
Sbjct:  420   tgcaaaattgatggcggttttatacgaccgaatacacctacaacgaaacaacccaacaa  479

Query:  1592  tggcatccgcatattcatattttgccttactcaatcaatggatagaccaggaagaattg  1651
              |||||||||||||||||||| |||| ||  | || |    |||| |||||||||||||| |||
Sbjct:  480   tggcatccgcatattcatattttgcgttagtgactgaccggattgaccaggaggaacta  539

Query:  1652  tccgaaacttggcacgatat  1671
              |  ||||||||||||||||||
Sbjct:  540   gcagaaacttggcacgatat  559

Score = 69.9 bits (35),  Expect = 1e-07
 Identities = 41/43 (95%)
 Strand = Plus / Plus
Query:  2130  cttgtaaggggttcgacccccttagaccccaaagggcgcactta  2172
              ||||||||||||  ||| |||||||||||||||||||||||||||
Sbjct:  1063  cttgtaaggggtcggccccttagaccccaaagggcgcactta  1105

Score = 61.9 bits (31),  Expect = 3e-05
 Identities = 70/83 (84%)
 Strand = Plus / Plus
Query:  1907  cttccatatttggagctgttataccgttttgttttggtaaaaaatcttattacaaccta  1966
              ||||||||| | |||||| | || ||||| |||||||||| |   ||||||||||||||
Sbjct:  796   cttccatatcttgagctgctctatcgtttcgttttggtgaaaggtcttattacaaccta  855

Query:  1967  gaaataacaaaagacgtaaagcc  1989
              ||  |||| || |||||||||||
Sbjct:  856   gagttaactaaggacgtaaagcc  878

>>>>nrnuc:GI_377552564 Gi|377552564|gb|JN872565.1| Acinetobacter baumannii strain DS002
         plasmid pTS236, complete sequence. 0/0
         Length = 2252
 Identities = 226/269 (84%)
 Strand = Plus / Plus
Query:  622   atgattaatttacaaggaactctaattaatgcttttcgtgtggatggtggtaaaggtaaa  681
              |||||||||||||||||||||||||| |||||||| ||| | ||||  ||||||||||||
Sbjct:  1925  atgattaatttacaaggaactctaatcaatgctttccgtatggacggtggtaagggtaaa  1984

Query:  682   gacggcaaagaatatgaagcgcgtgacaaggtgcaaattcttggttcgttggagttaccc  741
              || || ||||| || ||||||||||||||||||||||  |||||| |||||||| |||||
Sbjct:  1985  gatgggaaagagtacgaagcgcgtgacaaggtacaaatacttggttcgctggaactaccc  2044

Query:  742   aatggggaaattaaacacgaacttgttgacctaacagttgaggattctcgacttttgaa  801
              |||||  |||||||||||||||||||||||| ||||||||||| || | |  |  |  |
Sbjct:  2045  aatggagagattaaacacgaacttgttgacctcacagttgatgatgccagtgtctaccag  2104

Query:  802   ccattcaaaaatcaggttattagcatctcatgtggtgctatggctgtcggtcgtaatgtt  861
              ||| | ||||| | || |||    || ||  || || ||||||||||||||||||||||
```

FIGURE 1I

```
Sbjct: 2105  ccactaaaaaataaagtaatttctatttcctgcggtgctatggctgtaggtcgtaatgtt  2164

Query: 862   atttttatgttcgcaaaggcgcaaaacc  890
             |||||||||||||| ||||| ||||||||
Sbjct: 2165  gtttttatgttcgaaaaggtgcaaaacc  2193

Score =  182 bits (92), Expect = 1e-41
 Identities = 143/160 (89%)
 Strand = Plus / Plus Query: 951   gatactattgattaactaggggacaaaaattgactataaaagacaataaaaaagcccata  1010
             ||||||||||||||  |||||||||||||| || ||||||||||||||||||||||||
Sbjct: 19    gatactattgattaaagtggggacaaaaattgcttaaaaagacaataaaaaagcccata  78

Query: 1011  attcggatgctttggcgggcgatgaattacaggctttgcaatctgctaaggcagatcaac  1070
             ||| || |||||||||||| ||  |||||||||||||||||||||| || ||||||||
Sbjct: 79    tttcagaagctttggcgggcggagaaatacaggctttgcaatctgcaaacgcagatcaac  138

Query: 1071  acagggatagaataacacgttttggaattttgaaacatag  1110
             ||||||||||||||||||||||| | ||||||||||||
Sbjct: 139   acagggatagaataacacgttttgcgactttgaaacatag  178

Score = 46.1 bits (23), Expect = 1.6
 Identities = 23/23 (100%)
 Strand = Plus / Plus
Query: 1589  gaatggcatccgcatattcatat  1611
             |||||||||||||||||||||||
Sbjct: 669   gaatggcatccgcatattcatat  691

>>>>nrnuc:GI_169147044 Gi|169147044|emb|CU459139.1| Acinetobacter baumannii str. AYE plasmid
            p4ABAYE, complete genome. 0/0
           Length = 2726
 Score =  107 bits (54), Expect = 5e-19
 Identities = 87/98 (88%)
 Strand = Plus / Plus
Query: 805   ttcaaaaatcaggttattagcatctcatgtggtgctatggctgtcggtcgtaatgttatt  864
             ||||||||| || |||||||||||  |||||||||||||||| |||||| ||||||
Sbjct: 2570  ttcaaaaataagcttattagcatcagttgtggtgctatggctgttggtcgtaacgttatt  2629

Query: 865   ttttatgttcgcaaaggcgcaaaaccagttttagcaga  902
             |||||||||| ||||| || ||||| ||||||||||
Sbjct: 2630  ttttatgttcgaaaaggtgcgaaacctgttttagcaga  2667

Score = 95.6 bits (48), Expect = 2e-15
 Identities = 60/64 (93%)
 Strand = Plus / Plus
Query: 1063  agatcaacacagggatagaataacacgttttggaattttgaaacatagagcgaagctaca  1122
             |||||||| |||||||||||||||||||||||| ||||||||||||||||| ||| |||
Sbjct: 119   agatcaacatagggatagaataacacgttttggcattttgaaacatagatcgaagcaaca  178

Query: 1123  agaa  1126
             ||||
Sbjct: 179   agaa  182

Score = 73.8 bits (37), Expect = 7e-09
 Identities = 94/113 (83%)
 Strand = Plus / Plus Query: 1505  aaaaaaggtcgtggttttaatcagtttttgtaaaattgatggtgcttttattcaactgaa  1564
             |||||||| ||||| |||||| |||| |||||| ||||||| | |||||| |||  |||
Sbjct: 573   aaaaagggcgtggctttaatgaattttgcaaaattaatggtgcgatgtattcatatgag  632

Query: 1565  tatacatacaatccaaaaactaaagaatggcatccgcatattcatattttgc  1617
             |||| |||||| ||||||||| ||||||||||||| |||||||||| |||||
Sbjct: 633   aatacttacaatgaaaaaactaatgaatggcatcctcatattcatatgtttgc  685
```

FIGURE 2A

*HCBI2.170   (rmf.D1.10E.2.11k)   (1707bp)*

```
GAATTCAATA TGTTCGCTTC TAACCATTAC AACGACTTTA CTGGTTCTGG AGATTTATCA GATGATTAAA TTAGAAGGAA
TCGTTTTAAA CGTCTTCACT CAGCAAGGTG GACAAAACAA AAAAGGCGAA TCATTTGATG ATCGTGACAA GGTACAAATT
TTAGGTGCTA TGGATCTGCC CAATGGTGAT GTAAAAAATG AGCTTTTTAC GTTATCTGTA GATGATTATC GGGACTTTAA
AGACTTCCTA AATCGAAAAA TTTGTATTGC TGTTGGTGCA ATGGCAAGTG GCCGTAATGT TATTTTTTAT GTTGCTAAAG
GTGCAAAGCC TATATCAGCA GAATTTGCGT GAAACGCTAA AAAAAACAGT GAGTTAGCCT TGGCTTCTCG CTGTTTTTTC
TTTCTCTTGA TACTATTGAT TAACTAGGGG ACAAAAATTG ACTAAAAAAG ACAATAAAAA AGCCCATAAT TCGGACACTT
TGGCGGGTGA TGAATTACAG GCTTTGCAAT CTGCTAAGGC AGATCAACAC AGGGATAGAA TATCACGTTT TGGACTTTTG
AAACATAGAG CGAAGCTACA AGAACAATAT TTGTGGACGC AGGTTGATTT CAAATCCGAA GGTGAAAATG AGACATCCAA
TAAGGCTCTT AAGGCTGCAA CCAAATTAAA GGGATGCGGT CAATTTTTGC TATTCCATAA CTACTACACA ATTGACCAAG
TTAAACTTGC TAAGGCCCAT TATTGTTCTC AGCATTTGCT TTGCCCTATG TGTGCTGGTG TAAGGGCTGC TAAGTCAATG
AGTAGATATG TTCAACGTAT TGAAGAATTG ATGCGTCAGA ATCGCAAATT AAAGCCCGTA TTGATCACTT TAACGGTTAA
GAATGCGGAA GACCTAGAAG AACGCTTAA ACACTTAGAC GCTCATTTAG GACGCTTTTA GATCGTTATA ACGATTACAA
AAAGAAAGGT CGTGGTTTTA ATCAATTCTG CAAGATTGAT GGTGCTTTTT TATTCCACTG AATATACCTA CAATTCAAAA
ACAAAAGAGT GGCATCCCCA TATCCATATT TTCGCTTTAC TCAATGAATG GATAGACCAG GAAGAATTGG CCGAGACCTG
GCATGACATT ACCCTGGATT CTTATATCGT AGATATTCGT AGAGTTAAAA GGACCAAAGA ACACGGCTAT AGCAAAGCTG
TTGCAGAGGT TTGTAAATAT GCTCTTAAGT TTAGTGATTT GTCACTTGAG AATACGTGGG AAGCTTATCT TTCTTTAAAA
GGTAATAGGC TTACTGGCTG TTTTGGTTCT ATGTATGGTG TCAAGTTGCC TGAAAAACTC ACAGATGATT TACCCCTTGA
TGATCTTCCA TATATGGAGC TGCTATACCG TTTTGTCTTT GGTAAAAAAT AACATTACGG CCACTTGCCA TTGCACCAAC
AGCAATACAA ATTTTTCGAT TTAGGAAGTC TTTAAAGTCC CGATAATCAT CTACAGATAA CGTAAAAAGC TCATTTTTTA
CATCACCATT GGGCAGATCC ATAGCACCTA AAATTTGTAC CTTGTCACGA TCATCAAATG ATTCGCCTTT TTTGTTTTGT
CCACCTTGCT GAGTGAAGAC GTTTAAAACG ATTCCTTCTA ATTTAATCAT CTGATAAATC TCCAGAACCA GTAAAGTCGT
TGTAATGGTT AGAAGCGAAC ATATGAA
```

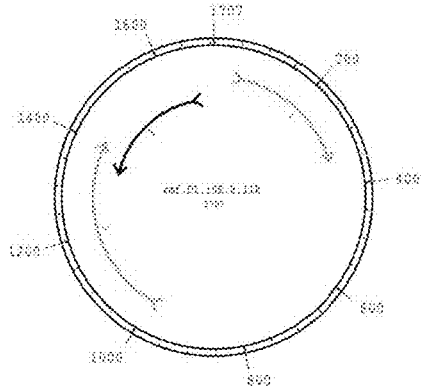

74% nucleotide similarity to Sphinx2.36 (2364bp)

*ORFs:*

137 amino acids    81% similarity to Sphinx2.36 (232aa) replication protein
96 amino acids    53% similarity to Sphinx2.36 (96 aa)  function?

137 amino acids        81% similarity to Sphinx2.36 (232aa)      replication protein

```
                    1                                                        50
SPHINX2.36.96.PEP   MINLQGTLIN AFRLDGGKGK DGKEYEARDK VQILGSLELP NGEIKHELVD
HCBI2.170.137.pep   MIMLEGIVLN VFTQQGGQMK KGESFDDRDK VQILGAMDLP NGDVKNELFT 51                                                       96
SPHINX2.36.96.PEP   LTVEDARIFE PFKHKVISIS CGAMAIGRNV VFYVRKGAKP VLADVM
HCBI2.170.137.pep   LSVDDYRDFK DFLNRKICIA VGAMASGRNV IFYVAKGAKP ISAEFA
```

96 amino acids        53% similarity to Sphinx2.36 (96 aa)       function?

```
                    1                                                       50
SPHINX2.36.232.PEP  MQEQYLWTQV DFKVGSETSI KALKAATKLK GCGQFLLFRN YYTIDQIKLE
HCBI2.170.96.pep    ~~~~~~~~~~ ~~~~~~~~~~ ~~~~~~~~~~ ~~~~~~~~~~ ~~~~~~~~~~
```

FIGURE 2B

```
                         51                                                    100
    SPHINX2.36.232.PEP   KFHVCGQHLL CPMCAGIRAA RSMNRYIQRI EEIMRQNRKL KPVLITLTVK
       HCBI2.170.96.pep  ~~~~~~~~~~ ~~~~~~~~~~ ~~~~~~~~~~ ~~~~~~~~~~ ~~~~MVL...

101                                                   150
    SPHINX2.36.232.PEP   NGEDLQERFE HLTGSFKTLL QRYRDFKKKG RGFNQFCKID GGFYTTEYTY
       HCBI2.170.96.pep  .......... .......... .......... .......... ..FYSTEYTY 151                                                   200
    SPHINX2.36.232.PEP   NETTQQWHPH IHIFALVTDR IDQEELAETW HDITLDSYIV DIRRVKKTKE
       HCBI2.170.96.pep  NSKTKEWHPH IHIFALLNEW IDQEELAETW HDITLDSYIV DIRRVKRTKE 201                                                   250
    SPHINX2.36.232.PEP   HGYAKAVAEV CKYALKFSDL STEKTFQAFF DP~~~~~~~~ ~~~~~~~~~~
       HCBI2.170.96.pep  HGYSKAVAEV CKYALKFSDL SLENTWEAYL SLKGNRLTGC FGSMYGVKLP 251                  276
    SPHINX2.36.232.PEP   ~~~~~~~~~~ ~~~~~~~~~~ ~~~~~~
       HCBI2.170.96.pep  EKLTDDLPLD DLPYMELLYR FVFGKK
```

*BlastN2:*

>>>nrnuc:GI_313507479  Gi|313507479|gb|HQ444405.1| TSE-associated...   159   1e-34
>>>nrnuc:GI_377552564  Gi|377552564|gb|JN872565.1| Acinetobacter ...    96   1e-15
>>>nrnuc:GI_169147044  Gi|169147044|emb|CU459139.1| Acinetobacter...    80   9e-11
>>>nrnuc:GI_510026963  Gi|510026963|gb|GAJD01035297.1| TSA: Ursus...    46   1.2

>>>>nrnuc:GI_313507479 Gi|313507479|gb|HQ444405.1| *TSE-associated circular DNA isolate*
        *Sphinx 2.36, complete sequence. 0/0*
         Length = 2364
 Score =  159 bits (80), Expect = 1e-34
 Identities = 98/104 (94%)
 Strand = Plus / Plus
Query:  462  gcccataattcggacactttggcgggtgatgaattacaggctttgcaatctgctaaggca  521
             ||||||||||| || ||||||||||| || ||||||||||||||||||||||||||  |||
Sbjct: 2261  gcccataattctgatgctttggcgggcgacgaattacaggctttgcaatctgctaatgca  2320

Query:  522  gatcaacacagggatagaatatcacgttttggacttttgaaaca  565
             ||||||||||||||||||||||||||||||||||||||||||||
Sbjct: 2321  gatcaacacagggatagaatatcacgttttggacttttgaaaca  2364

Score =  131 bits (66), Expect = 3e-26
 Identities = 336/425 (79%), Gaps = 7/425 (1%)
 Strand = Plus / Plus
Query:  579  caagaacaatatttgtggacgcaggttgatttcaaatccgaaggtgaaaatgagacatcc  638
             |||||||||||||||||||| ||||||||||||||||       | || || ||| |||||
Sbjct:   15  caagaacaatatttgtggactcaggttgatttcaag------gttggaagtgaaacatct   68

Query:  639  aataaggctcttaaggctgcaaccaaattaaagggatgcggtcaattttttgctattccat  698
             |  || |||||||||||||||||||||||||||||||||||||||||| |||| || | |
Sbjct:   69  atcaaagctcttaaggctgcaaccaaattaaagggatgcggtcaatttctgcttttcgt   128

Query:  699  aactactacacaattgaccaagttaaacttgctaaggcccattattgttctcagcatttg  758
             || |||||||| || || ||| || || ||||||   ||    ||    |||||||||
Sbjct:  129  aattactacaccatagatcaaatcaagctcgaaaaattccacgtatgcggacagcatttg  188

Query:  759  ctttgccctatgtgtgctggtgtaagggctgctaagtcaatgagtagatatgttcaacgt  818
             || || || ||||||||||||| |  | |||||     ||||||| | | ||| ||||||
Sbjct:  189  ctatgtccaatgtgtgctggtattcgtgctgcccgttcaatgaatcggtatattcaacgc  248

Query:  819  attgaagaattgatgcgtcagaatcgcaaattaaagcccgtattgatcactttaacggtt  878

FIGURE 2C

```
              ||  ||||||  |  ||||||||||||||||  ||||||||||||||||||||  ||  |||
Sbjct: 249    atcgaagaaataatgcgtcagaatcgcaagctaaagcccgtattgatcactttgaccgtt 308

Query: 879    aagaatggggaagacctagaagaacgctttaaaca-cttagacgctcatttaggacgctt 937
              ||||  ||  |||||||||  |  ||||||||||  ||||  ||  |  ||||||||||  |||||||
Sbjct: 309    aagaacggtgaagacctacaggaacgctttgaacacctcacaggctcatttaagacgctt 368

Query: 938    ttagatcgttataacgattacaaaaagaaaggtcgtggttttaatcaattctgcaagatt 997
              |||  |  |||||      ||||    ||  ||  ||  |||||  ||  ||||||||||  |||||  |||
Sbjct: 369    ttacagcgttaccgtgattttaagaaaaagggtcgagggtttaatcaattttgcaaaatt 428

Query: 998    gatgg 1002
              |||||
Sbjct: 429    gatgg 433

Score = 54.0 bits (27), Expect = 0.005
 Identities = 45/51 (88%)
 Strand = Plus / Plus
Query: 367    cagtgagttagccttggcttctcgctgtttttctttctcttgatactatt 417
              ||||||||||||  ||||  |  ||||||||||||||||||  ||||||||||||
Sbjct: 2167   cagtgagttaggcttgccgactcgctgtttttcttttacttgatactatt 2217

>>>>nrnuc:GI_377552564 Gi|377552564|gb|JN872565.1| Acinetobacter baumannii strain DS002
        plasmid pTS236, complete sequence. 0/0
           Length = 2252
 Score = 95.6 bits (48), Expect = 1e-15
 Identities = 83/92 (90%), Gaps = 2/92 (2%)
 Strand = Plus / Plus
Query: 478    ctttggcgggtgatgaattacaggctttgcaatctgctaaggcagatcaacacagggata 537
              ||||||||||  |   |||  ||||||||||||||||||||||  ||  |||||||||||||||||||||
Sbjct: 88     ctttggcgggcggagaaatacaggctttgcaatctgcaaacgcagatcaacacagggata 147

Query: 538    gaatatcacgttttg-gactttgaaacatag 568
              |||||  |||||||||  |||  ||||||||||||
Sbjct: 148    gaataacacgttttgcgac-tttgaaacatag 178

Score = 50.1 bits (25), Expect = 0.078
 Identities = 31/33 (93%)
 Strand = Plus / Plus
Query: 391    ctgttttttcttctcttgatactattgattaa 423
              |||||||||||||||    ||||||||||||||||||||
Sbjct: 1      ctgttttttcttttacttgatactattgattaa 33

>>>>nrnuc:GI_169147044 Gi|169147044|emb|CU459139.1| Acinetobacter baumannii str. AYE
        plasmid p4ABAYE, complete genome. 0/0
           Length = 2726
 Score = 79.8 bits (40), Expect = 9e-11
 Identities = 58/64 (90%)
 Strand = Plus / Plus
Query: 521    agatcaacacagggatagaatatcacgttttggacttttgaaacatagagcgaagctaca 580
              ||||||||||  |||||||||||||  ||||||||  ||||||||||||||||||  ||||||  |||
Sbjct: 119    agatcaacatagggatagaataacacgttttggcatttttgaaacatagatcgaagcaaca 178

Query: 581    agaa 584
              ||||
Sbjct: 179    agaa 182

Score = 50.1 bits (25), Expect = 0.078
 Identities = 43/49 (87%)
 Strand = Plus / Plus
Query: 849    ttaaagcccgtattgatcactttaacggttaagaatggggaagacctag 897
              ||||||||||||  ||||||  ||  ||||||||  |||||||  ||||||||
Sbjct: 459    ttaaagcccgttatgatcacgtttacggttaaaaatggggtagacctag 507
```

*FastA \*Geall*

FIGURE 2D

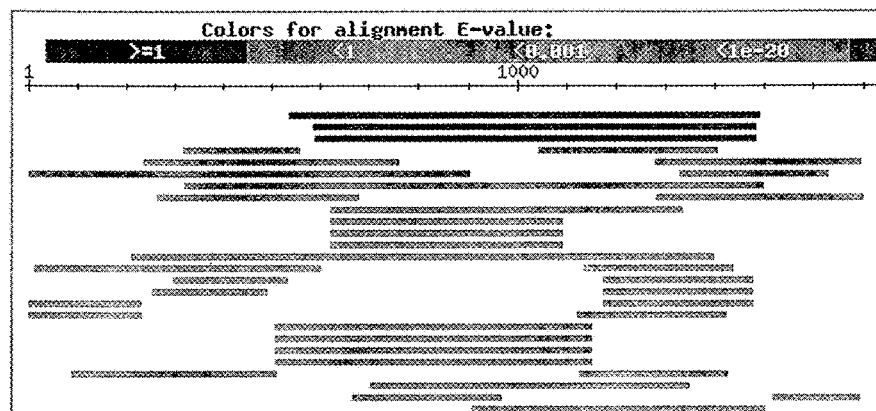

EMSTD_UNC:HQ444405   Begin: 1    End: 885
! Hq444405 TSE-associated circular DN...  1438  1868  2309  1706.3   5.3e-89
EMSTD_PRO:CU459139   Begin: 226  End: 1032
! Cu459139 Acinetobacter baumannii st...  1194  1691  1655  1222.6   4e-62
EMSTD_PRO:JN872565   Begin: 240  End: 1072
! Jn872565 Acinetobacter baumannii st...  1234  1990  1624  1200.2   8.6e-61
EMSTD_UNC:HQ444405   Begin: 1846 End: 2175 Strand: -
! Hq444405 TSE-associated circular DN...   513   580   520   384.2   2.3e-15

EMSTD_UNC:HQ444405
ID    HQ444405; SV 1; circular; genomic DNA; STD; UNC; 2364 BP.
AC    HQ444405;
DE    *TSE-associated circular DNA isolate Sphinx 2.36, complete sequence.*
SCORES   E(): 5.3e-89
>>EMSTD_UNC:HQ444405                                      (2364 nt)
 74.1% identity in 892 nt overlap
 (566-1451:1-885)

540       550       560       570       580       590
HCBI2.170   TAGAATATCACGTTTTGGACTTTTGAAACATAGAGCGAAGC-TACAAGAACAATATTTGT
                                           ||||  |  || |  |  ||||||||||||||||
HQ444405                                  TAGATCTAAACATGCAAGAACAATATTTGT
                                                     10        20        30

600       610       620       630       640       650
HCBI2.170   GGACGCAGGTTGATTTCAAATCCGAAGGTGAAAATGAGACATCCAATAAGGCTCTTAAGG
            ||||  |||||||||||||||      |  ||  || |||  ||| |  |  |||||||||||
HQ444405    GGACTCAGGTTGATTTCA------AGGTTGGAAGTGAAACATCTATCAAAGCTCTTAAGG
                   40        50        60        70        80

660       670       680       690       700       710
HCBI2.170   CTGCAACCAAATTAAAGGGATGCGGTCAATTTTTGCTATTCCATAACTACTACACAATTG
            |||||||||||||||||||||||||||||||||  |||| ||  |  |||  ||||||||  ||  |
HQ444405    CTGCAACCAAATTAAAGGGATGCGGTCAATTTCTGCTTTTTCGTAATTACTACACCATAG
                   90       100       110       120       130       140

720       730       740       750       760       770
HCBI2.170   ACCAAGTTAAACTTGCTAAGGCCCATTATTGTTCTCAGCATTTGCTTTGCCCTATGTGTG
             ||||  |  || ||  ||    |||   ||   ||         |||||||||||||||||
HQ444405    ATCAAATCAAGCTCGAAAAATTCCACGTATGCGGACAGCATTTGCTATGTCCAATGTGTG
                  150       160       170       180       190       200

780       790       800       810       820       830
HCBI2.170   CTGGTGTAAGGGCTGCTAAGTCAATGAGTAGATATGTTCAACGTATTGAAGAATTGATGC
            |||||  |  |  ||||||    ||||||||  |  |||  |||||||  ||||||||  ||||
HQ444405    CTGGTATTCGTGCTGCCCGTTCAATGAATCGGTATATTCAACGCATCGAAGAAATAATGC
                  210       220       230       240       250       260

840       850       860       870       880       890
HCBI2.170   GTCAGAATCGCAAATTAAAGCCCGTATTGATCACTTTAACGGTTAAGAATGGGGAAGACC
            ||||||||||||||   ||||||||||||||||||||||| || ||||||||| ||  |||||||
HQ444405    GTCAGAATCGCAAGCTAAAGCCCGTATTGATCACTTTGACCGTTAAGAACGGTGAAGACC
                  270       280       290       300       310       320

900       910       920       930       940       950
HCBI2.170   TAGAAGAACGCTTTAAACA-CTTAGACGCTCATTTAGGACGCTTTTAGATCGTTATAACG
            || |  ||||||||||| |||| ||  |  |||||||||||| ||||||||||| | |||||         |
HQ444405    TACAGGAACGCTTTGAACACCTCACAGGCTCATTTAAGACGCTTTTACAGCGTTACCGTG

FIGURE 2E

```
                     330       340       350       360       370       380
                     960       970       980       990       1000      1010
HCBI2.170   ATTACAAAAAGAAAGGTCGTGGTTTTAATCAATTCTGCAAGATTGATGGTGCTTTTTTAT
            |||  || || || ||||| || ||||||||||| ||||| ||||||| | |||||||
HQ444405    ATTTTAAGAAAAAGGGTCGAGGGTTTAATCAATTTTGCAAAATTGATGGCG-GTTTTTAT
                     390       400       410       420       430       440

1020      1030      1040      1050      1060      1070
HCBI2.170   TCCACTGAATATACCTACAATTCAAAAACAAAAGAGTGGCATCCCCATATCCATATTTTC
            |  || ||||| |||||||||  || ||| || | |||||||| || ||||| |||||||
HQ444405    ACGACCGAATACACCTACAACGAAACAAACCCAACAATGGCATCCGCATATTCATATTTTT
                     450       460       470       480       490       500

1080      1090      1100      1110      1120      1130
HCBI2.170   GCTTTACTCAATGAATGGATAGACCAGGAAGAATTGGCCGAGACCTGGCATGACATTACC
            || ||| | ||||   ||||  ||||||||| |||  ||||| ||| || || || ||
HQ444405    GCGTTAGTGACTGACCGGATTGACCAGGAGGAACTAGCAGAAACTTGGCACGATATAACG
                     510       520       530       540       550       560

1140      1150      1160      1170      1180      1190
HCBI2.170   CTGGATTCTTATATCGTAGATATTCGTAGAGTTAAAAGGACCAAAGAACACGGCTATAGC
            ||  |||| || || || |||||  |||| || ||||||||||||| |||| ||||| |||
HQ444405    CTTGATTCATACATTGTGGACATCCGCAGGGTCAAAAAAACTAAAGAACACGGATATGCA
                     570       580       590       600       610       620

1200      1210      1220      1230      1240      1250
HCBI2.170   AAAGCTGTTGCAGAGGTTTGTAAATATGCTCTTAAGTTTAGTGATTTGTCACTTGAGAAT
            || |||||||| || || || ||||| ||||||||||||||||| ||| ||| |||||||
HQ444405    AAGGCTGTTGCCGAAGTCTGCAAATACGCTCTTAAGTTTAGCGATCTATCCACTGAGAAA
                     630       640       650       660       670       680

1260      1270      1280      1290      1300      1310
HCBI2.170   ACGTGGGAAGC-TTATCTTTCTTTAAAAGGTAATAGGCTTACTGGCTGTTTTGGTTCTAT
            || |  |||| |||| || | | | || || || ||||||||| || || || || |||||
HQ444405    ACCTTTCAAGCATTTTTTGACCCTTAAGGGCAAAAGGCTTACAGGTTCATTCGGCTCTAT
                     690       700       710       720       730       740

1320      1330      1340      1350      1360      1370
HCBI2.170   GTATGGTGTCAAGTTGCCTGAAAAACTCACAGATGATTTACCCCTTGATGATCTTCCATA
            | |||||||| || | ||||||||     |  |||||| || || ||||| || ||||||
HQ444405    GCATGGTGTAAAAATTCCTGAAAGCGGACCCGATGAAATGCCTAAAGAGGAACTTCCATA
                     750       760       770       780       790       800

1380      1390      1400      1410      1420
HCBI2.170   TATGGAGCTGCTATACCGTTTTGTCTTTGGTAAAAAATAACATTACGGCC---ACTTGCC
            | | ||||||||| ||||| || |||||||| ||||  |||| || |||     | || |
HQ444405    TCTTGAGCTGCTCTATCGTTTCGTTTTTGGTGAAAGGTCTTATTACAACCTAGAGTTAAC
                     810       820       830       840       850       860

1430      1440      1450      1460      1470      1480
HCBI2.170   ATTGCACCAACAGCAATACAAATTTTTCGATTTAGGAAGTCTTTAAAGTCCCGATAATCA
            | ||  | |||  |||||
HQ444405    TAAGGACGTAAAGCCGAACAAAAGGAATGAGGAAAGATGAACGAGGAGCTTCGACGAGGC
                     870       880       890       900       910       920
```

EMSTD_PRO:CU459139
ID   CU459139; SV 1; circular; genomic DNA; STD; PRO; 2726 BP.
AC   CU459139;
DE   *Acinetobacter baumannii* str. AYE plasmid p4ABAYE, complete genome. . . .
SCORES   z-score: 1222.6 E(): 4e-62
>>EMSTD_PRO:CU459139                            (2726 nt)
 67.7% identity in 808 nt overlap
 (616-1419:226-1032)
                     590       600       610       620       630       640
HCBI2.170   AATATTTGTGGACGCAGGTTGATTTCAAATCCGAAGGTGAAAATGAGACATCCAATAAGG
                                       ||||  |   |||| || |   ||| |   |
CU459139    CGTTAGCTAAGATTAAAGAAAATTATCATGCCGATGTAAAAAACGATGAATCTATTCGCG
                     200       210       220       230       240       250

650       660       670       680       690       700
HCBI2.170   CTCTTAAGGCTGCAACCAAATTAAAGGGATGCGGTCAATTTTGCTATTCCATAACTACT
            |  | ||  ||||      ||||||| |  |||||||||  ||| || |||| |   |
CU459139    CCATGAAAACTGCCCAAAAATTAAATGGGTGCGGTAATTTTCTTCTATTCAAAAATTTTT
                     260       270       280       290       300       310

710       720       730       740       750       760
HCBI2.170   ACACAATTGACCAAGTTAAACTTGCTAAGGCCCATTATTGTTCTCAGCATTTGCTTTGCC
            ||||| ||| | ||| ||||||||| |||  ||   |  | ||||||||||| | || |
```

FIGURE 2F

```
CU459139    ACACCATTAATCAAATTAAACTCGCCAAGTTCCAAGCTTGTAGTGAGCATTTGTTATGTC
               320       330       340       350       360       370

770       780       790       800       810       820
HCBI2.170   CTATGTGTGCTGGTGTAAGGGCTGCTAAGTCAATGAGTAGATATGTTCAACGTATTGAAG
            |  | ||||||||| | || ||| ||||| ||||   | |||  |  | ||| ||||
CU459139    CGTTTTGTGCTGGTATTAGAGCTTCTAAGGCAATTCAAAAATACTCTGAGCGTGTTGATC
               380       390       400       410       420       430

830       840       850       860       870       880
HCBI2.170   AATTGATGCGTCAGAATCGCAAATTAAAGCCCGTATTGATCACTTTAACGGTTAAGAATG
            || | |   | | ||||   |||||||| ||  ||||||||||| ||||||   ||||
CU459139    AAGTCTTATCTGAAAATCCTCGTTTAAAGCCCGTTATGATCACGTTTACGGTTAAAAATG
               440       450       460       470       480       490

890       900       910       920       930       940
HCBI2.170   GGGAAGACCTAGAAGAACGCTTTAAACA-CTTAGACGCTCATTTAGGACGCTTTTAGATC
            ||| ||||||||  |||| |||  || |  || |||| |||||| |||| ||||| ||| |
CU459139    GGGTAGACCTAGGGGAACGGTTCACCCATCTTATAAAATCGTTTAGAACGCTTATAGAGC
               500       510       520       530       540       550

950       960       970       980       990       1000
HCBI2.170   GTTATAACGATTACAAAAGAAAGGTCGTGGTTTTAATCAATTCTGCAAGATTGATGGTG
            ||  ||  || || |  ||  ||||| ||||| |||||| ||||  ||||| ||| ||||||
CU459139    GTCGTAGGGACTATATTAAAAAAGGGCGTGGCTTTAATGAATTTTGCAAAATTAATGGTG
               560       570       580       590       600       610

1010      1020      1030      1040      1050      1060
HCBI2.170   CTTTTTTATTCCACTGAATATACCTACAATTCAAAAACAAAAGAGTGGCATCCCCATATC
            |   | |||||   ||| |||| ||||||   || || ||||||||  |||  | ||||
CU459139    C-GATGTATTCATATGAGAATACTTACAATGAAAAAACTAATGAATGGCATCCTCATATT
               620       630       640       650       660       670

1070      1080      1090      1100      1110      1120
HCBI2.170   CATATTTTCGCTTTACTCAATGAATGGATAGACCAGGAAGAATTGGCCGAGACCTGGCAT
            |||||  || ||  |  |||| |||||||||||| |||||  ||||| |       |||||
CU459139    CATATGTTTGCACTTTTGGATGATTGGATAGATCAGGATGAATTGTCTCAATATTGGCAA
               680       690       700       710       720       730

1130      1140      1150      1160      1170      1180
HCBI2.170   GACATTACCCTGGATTCTTATATCGTAGATATTCGTAGAGTTAAAAGGACCAAAGAACAC
            ||||||   ||| |||    |||| ||||||||||||||| ||||     |||||
CU459139    TCCATTACTGGGGACTCTATGGTCGTTGATATTCGTAGAGCCAAAAAACAAAAAGACTTA
               740       750       760       770       780       790

1190      1200      1210      1220      1230      1240
HCBI2.170   GGCTATAGCAAAGCTGTTGCAGAGGTTTGTAAATATGCTCTTAAGTTTAGTGATTTGTCA
            ||||||     |||| || || || |||||||||||||||| |||| |  |  | ||
CU459139    GGCTATTCAGGTGCTGCTGCTGAAGTCTGTAAATATGCTCTCAAATTTGGTGATCTTTCT
               800       810       820       830       840       850

1250      1260      1270      1280      1290      1300
HCBI2.170   CTTGAGAATACGTGGGAAGCTTATCTTTCTTTAAAAGGTAATAGGCTTACTGGCTGTTTT
            |  || || || |||||||||||   |||||||| | |||| |||   | | |||  ||||
CU459139    GTAGAAAAGACTTGGGAAGCTTTCAAAGTTTTGAAAGGTAAGCGATTAAGTGGGGCTTTT
               860       870       880       890       900       910

1310      1320      1330      1340      1350      1360
HCBI2.170   GGTTCTATGTATGGTGTCAAGTTGCCTGAAAAACTCACAGATGATTTACC---CCTTGAT
            || ||| | | || || || | |||||| | | |||||||  | |  |    |  |
CU459139    GGATCTCTTTGGGCGTGAAAATTCCTGAATCATTGATAGATGATCTTCCAGACGATTCT
               920       930       940       950       960       970

1370      1380      1390      1400      1410      1420
HCBI2.170   GATCTTCCATATATGGAGCTGCTATACCGTTTTGTCTTTGGTAAAAAATAACATTACGGC
            ||| | || || ||| ||  || ||  ||  | |  |||||      |  ||||||
CU459139    GATTTACCTTATTTAGAAATGATTTATAAGTTCGTCTTTTCTAAGAAGTCTTATTACGAT
               980       990       1000      1010      1020      1030

1430      1440      1450      1460      1470      1480
HCBI2.170   CACTTGCCATTGCACCAACAGCAATACAAATTTTTCGATTTAGGAAGTCTTTAAAGTCCC

CU459139    TTACAACTTACTCGTCATGTCGAACCTACAGGTAAGGACGACGCCGACGAGCTTCGAGGA
               1040      1050      1060      1070      1080      1090
```

EMSTD_PRO:JN872565
ID    JN872565; SV 1; circular; genomic DNA; STD; PRO; 2252 BP.
AC    JN872565;
DE    *Acinetobacter baumannii* strain DS002 plasmid pTS236, complete sequence.

FIGURE 2G

```
SCORES    z-score: 1200.2 E(): 8.6e-61
>>EMSTD_PRO:JN872565                                            (2252 nt)
  67.0% identity in 836 nt overlap
  (618-1447:240-1072)

EMSTD_UNC:HQ444405
ID   HQ444405; SV 1; circular; genomic DNA; STD; UNC; 2364 BP.
AC   HQ444405;
DT   10-DEC-2010 (Rel. 107, Created)
DT   10-DEC-2010 (Rel. 107, Last updated, Version 1)
DE   TSE-associated circular DNA isolate Sphinx 2.36, complete sequence.
SCORES    z-score: 384.2 E(): 2.3e-15
>>EMSTD_UNC:HQ444405                                            (2364 nt)
  62.7% identity in 332 nt overlap
  (1666-1336:1846-2175)

1690      1680      1670      1660      1650      1640
HCBI2.170   GCTTCTAACCATTACAACGACTTTACTGGTTCTGGAGATTTATCAGATGATTAAATTAGA
                          ||  ||||||    |||||||||||||| |||  |
HQ444405    GCGGATCTCTATGCTTCAGGAAAAATGAAATCAGGAGATCAGTCAGATGATTAATTTACA
                1820      1830      1840      1850      1860      1870

1630      1620      1610      1600      1590      1580
HCBI2.170   AGGAATCGTTTTAAACGTCTTCACTCAGCAAGGTGGACAAAACAAAAAAGGCGAATCATT
            ||| |    || ||||  |    ||    |  | |||||  ||    ||| | ||| || ||
HQ444405    AGGGACACTTATAAATGCTTTTCGTCTTGATGGTGGTAAAGGGAAAGACGGCAAAGAATA
                1880      1890      1900      1910      1920      1930

1570      1560      1550      1540      1530      1520
HCBI2.170   TGATGATCGTGACAAGGTACAAATTTTAGGTGCTATGGATCTGCCCAATGGTGATGTAAA
            ||| |  ||||||||||| |||||| || |||| ||| |||  |||||| ||||  | ||
HQ444405    TGAAGCACGTGACAAGGTGCAAATTCTTGGTTCGCTGGAGTTGCCCAACGGTGAGATCAA
                1940      1950      1960      1970      1980      1990

1510      1500      1490      1480      1470      1460
HCBI2.170   AAATGAGCTTTTTACGTTATCTGTAGATGATTATCGGGACTTTAAAGACTTCCTAAATCG
             |  |||||||| ||    ||| || ||  |||    |||| |    |||  |   |||  |
HQ444405    ACATGAGCTTGTTGACTTAACGGTTGAAGATGCTCGCATCTTTGAGCCATTCAAACACAA
                2000      2010      2020      2030      2040      2050

1450      1440      1430      1420      1410      1400
rmf.D1.10E.2 AAAAATTTGTATTGCTGTTGGTGCAATGGCAAGTGGCCGTAATGTTATTTTTTACCAAAG
             ||||  |||  |    ||||| |||||  ||  ||  |||||||  ||||||   |
HQ444405    GGTAATTAGCATTTCATGCGGTGCTATGGCTATCGGTCGAAATGTTGTTTTTTATGTTCG
                2060      2070      2080      2090      2100      2110

1390      1380      1370      1360      1350      1340
HCBI2.170   ACAAAACGGTATAGCAGCTCCA-TATATGGAAGATCATCAAGGGGTAAATCATCTGTGAG
            | ||   |    | |   | |  | |||||  | ||   |||| |  |     |||||
HQ444405    AAAAGGTGCAAAGCCTGTTTTAGCAGATGTAATGTAATTCA--TGAAAAAAAACAGTGAG
                2120      2130      2140      2150      2160      2170

1330      1320      1310      1300      1290      1280
HCBI2.170   TTTTTCAGGCAACTTGACACCATACATAGAACCAAAACAGCCAGTAAGCCTATTACCTTT
            ||
HQ444405    TTAGGCTTGCCGACTCGCTGTTTTTCTTTTACTTGATACTATTAACTAAAGTGGGGACA
                2180      2190      2200      2210      2220      2230

EMSTD_PRO:CU459139
ID   CU459139; SV 1; circular; genomic DNA; STD; PRO; 2726 BP.
AC   CU459139;
PR   Project:PRJNA28921;
DT   26-FEB-2008 (Rel. 94, Created)
DT   05-NOV-2010 (Rel. 106, Last updated, Version 2)
DE   Acinetobacter baumannii str. AYE plasmid p4ABAYE, complete genome. . . .
SCORES    z-score: 339.5 E(): 6.2e-13
>>EMSTD_PRO:CU459139                                            (2726 nt)
  66.9% identity in 257 nt overlap
  (1656-1403:2380-2634)
```

FIGURE 3A

HCBI3.108  (rkg.T1.5E.2.11k)  (1082bp)

```
GCGAGTGTCT ACGAGCGAAG TTATGAAAGT TCGATTCTTC CCCCCTCTGA AAAACCGCTT TTAAAAATAT TGGCTGCTAG
ATGGTTTTTA CTATCGTGAG CTTTTGCTTT TAAAAAAACA CGAGCGAAGC GAGTTCATAG TTGCTTTTGG GGGTTTCGGG
GGGCTTGCCC CCTGAACAAG ATCACGGAGT GGGAATTTAT CACGGTAGTG AAAAAGTACC CTCTGTGTAT CCTTGCTTAT
TTCTTTTTAA ACCTTTGAAC TTTTTCCCGT AATTTGAAGA AATTGCCCCT CGACTAAGCT TGCTTAGTCA AAAAAGTTTG
AGCAAAGCGA AAACATAGGG CAATTTTCAT GATGAAAATG GGCTTTTAAG GCTTTTAAAT GCTTTTAAGG CTTTTAGACA
TGCTGAAACG CAAGCCTAGC AAGGCATACA GAGGGCATTT AACACCGTTT ACCTACCAAT ACCCCACCGT TTACCTACCA
ATACCCCACC GTTTACCTAC CAATACCCCA CCGTTTACCT ACCTTAATAC ACAATAATAT TTTTATGTGG TATAACGTAA
TAAAATATAT AGGTGGTTTA TGAGTGATTT AATAGTAAAA GATAACGCCC TAATGAACGC TAGTTATAAC TTAGACTTGG
TTGAACAGCG GTTAATTCTT TTAGCTATCC TTGAAGCTAG AGAATCAGGC AAAGGAATTA ACGCAAATGA CCCTCTTACA
GTCCATGCAG AGAGTTATAT CAATCAATTT GGTGTAGCTA GACAGACTGC TTATCAAGCC CTAAAAGATG CCTGCAAAGA
TTTATTTGCC CGTCAATTCA GCTATCAAGA AAAGCGTGAA CGTGGACGAG CTAATATTAC AAGTCGTTGG GTCAGCCAAA
TTGCTTACAT TGATGAAACT GCAACGGTTG AGGTTATTTT CGCCCCTGCG GTTGTTCCAC TGATCACAAG GTTAGAGGAA
CAATTCTCGA AGTACGTAAT TGAACAAATT AGTAGTCTAT CGAGTGCCTA TGCAGTTCGC TTATATGAGT TATTGATCTG
CTGGAGAACA ACAGGAAAGA CACCAGTTAT TGACTTAACA GAATTC
```

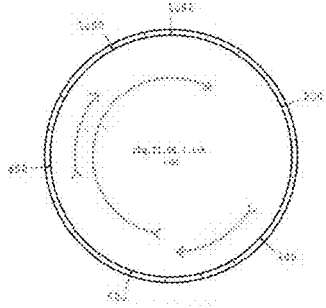

ORF 201 amino acids -- putative replication protein, DNA-binding domain
Similarity to Spinx1.76 (324aa)    88,2% in 169aa

```
                         1                                                          50
SPHINX1.76.324.PEP       MSDLIVKDNA LMNASYNLAL VEQRLILLAI IEARETGKGI NANDPLTVHA
HCBI3.108.201.pep        MSDLIVKDNA LMNASYNLDL VEQRLILLAI LEARESGKGI NANDPLTVHA
                         51                                                         100
SPHINX1.76.324.PEP       GSYINQFNVQ RHTAYQALKD ACKDLFARQF SYQEKRERGR INITSRWVSQ
HCBI3.108.201.pep        ESYINQFGVA RQTAYQALKD ACKDLFARQF SYQEKRERGR ANITSRWVSQ
                         101                                                        150
SPHINX1.76.324.PEP       IGYMDDTATV EIIFAPAVVP LITRLEEQFT QYDIEQISGL SSAYAVRMYE
HCBI3.108.201.pep        IAYIDETATV EVIFAPAVVP LITRLEEQFS KYDIEQISSL SSAYAVRLYE
                         151                                                        200
SPHINX1.76.324.PEP       LLICWRSTGK TPIIELDEFR KRIGVLDTEY TPTDNLKMQV IELALKQINE
HCBI3.108.201.pep        LLICWRTTGK TPVLDLTEFA S.......VY ER........ ..........
                         201                                                        250
SPHINX1.76.324.PEP       HTDITASYEQ HKKGRVITGF SFMFKHKKQN SDKTPDTNAS SPRIVKHSQI
HCBI3.108.201.pep        ......SYES S......... .......... .......... ..........
                         251                                                        300
SPHINX1.76.324.PEP       PTNIVKQFEN AKMSDLEHRA SRVTGEIMRN RLSDRFKQGD ESAIDMMKRI
HCBI3.108.201.pep        ...ILPPSEK PLLKILAARW FLLS~~~~~~ ~~~~~~~~~~ ~~~~~~~~~~
                         301                       324
SPHINX1.76.324.PEP       QSEIITDAIA DQWESKLEEF GVVF
HCBI3.108.201.pep        ~~~~~~~~~~ ~~~~~~~~~~ ~~~~
```

*BLASTN2:*

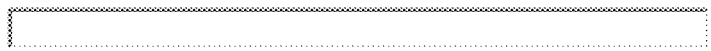

FIGURE 3B

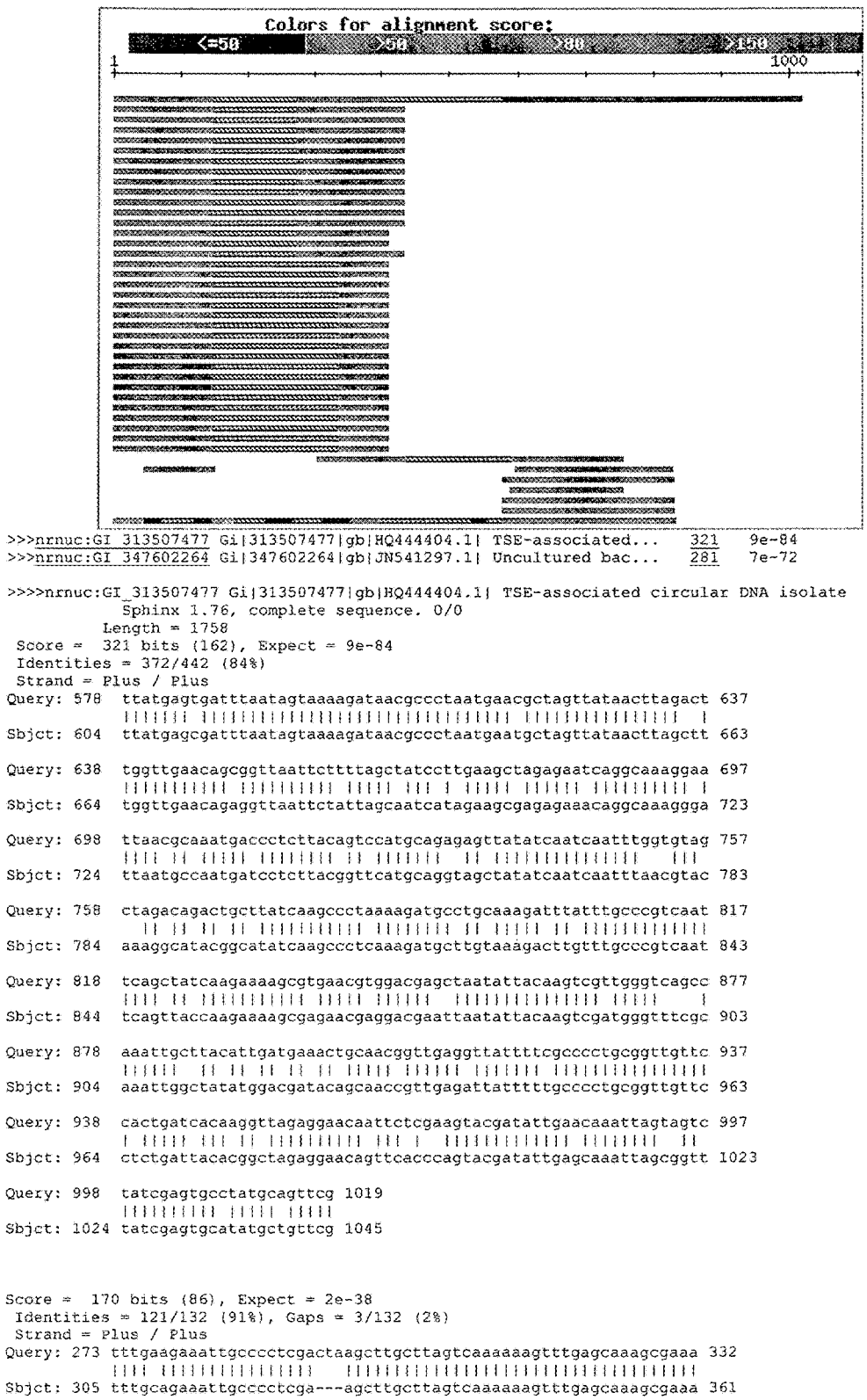

```
>>>nrnuc:GI_313507477  Gi|313507477|gb|HQ444404.1| TSE-associated...   321    9e-84
>>>nrnuc:GI_347602264  Gi|347602264|gb|JN541297.1| Uncultured bac...   281    7e-72

>>>>nrnuc:GI_313507477 Gi|313507477|gb|HQ444404.1| TSE-associated circular DNA isolate
            Sphinx 1.76, complete sequence. 0/0
            Length = 1758
 Score =  321 bits (162), Expect = 9e-84
 Identities = 372/442 (84%)
 Strand = Plus / Plus
Query: 578   ttatgagtgatttaatagtaaaagataacgccctaatgaacgctagttataacttagact 637
             |||||||  |||||||||||||||||||||||||||||||| ||||||||||||||| |
Sbjct: 604   ttatgagcgatttaatagtaaaagataacgccctaatgaatgctagttataacttagctt 663

Query: 638   tggttgaacagcggttaattcttttagctatccttgaagctagagaatcaggcaaaggaa 697
             |||||||||| ||||||||| |||| |||  | |||||||  |||||| ||||||||| |
Sbjct: 664   tggttgaacagaggttaattctattagcaatcatagaagcgagagaaacaggcaaaggaa 723

Query: 698   ttaacgcaaatgaccctcttacagtccatgcagagagttatatcaatcaatttggtgtag 757
             |||| || ||||| |||||||| |||||||| ||||||| || ||||||||||||| ||||
Sbjct: 724   ttaatgccaatgatcctcttacggttcatgcaggtagctatatcaatcaatttaacgtac 783

Query: 758   ctagacagactgcttatcaagccctaaaagatgcctgcaaagatttatttgcccgtcaat 817
                || || || |||||||||||| ||||||||  || |||| || ||||||||||||||
Sbjct: 784   aaaggcatacggcatatcaagccctcaaagatgcttgtaaagacttgtttgcccgtcaat 843

Query: 818   tcagctatcaagaaaagcgtgaacgtggacgagctaatattacaagtcgtgggtcagcc 877
             |||| || |||||||||| ||||| |||||| |||||||||||||||||| |||||   |
Sbjct: 844   tcagttaccaagaaaagcgagaacgaggacgaattaatattacaagtcgatgggtttcgc 903

Query: 878   aaattgcttacattgatgaaactgcaacggttgaggttattttcgccctgcggttgttc 937
             ||||||  || || || || || ||||| |||||| ||||||| ||||||||||||||||
Sbjct: 904   aaattggctatatggacgatacagcaaccgttgagattattttgccccctgcggttgttc 963

Query: 938   cactgatcacaaggttagaggaacaattctcgaagtacgatattgaacaaattagtagtc 997
             | |||||| || ||||||||||||| ||| | ||||||||||||| ||||||||| ||
Sbjct: 964   ctctgattacacggctagaggaacagttcacccagtacgatattgagcaaattagcggtt 1023

Query: 998   tatcgagtgcctatgcagttcg 1019
             |||||||||| ||||| |||||
Sbjct: 1024  tatcgagtgcatatgctgttcg 1045

Score =  170 bits (86), Expect = 2e-38
 Identities = 121/132 (91%), Gaps = 3/132 (2%)
 Strand = Plus / Plus
Query: 273   tttgaagaaattgccctcgactaagcttgcttagtcaaaaagtttgagcaaagcgaaa 332
             ||||  ||||||||||||||||   |||||||||||||||||||||||||||||||||
Sbjct: 305   tttgcagaaattgcccctcga---agcttgcttagtcaaaaagtttgagcaaagcgaaa 361
```

FIGURE 3C

```
Query: 333  acatagggcaattttcatgatgaaaatgggcttttaaggcttttaaatgcttttaaggct 392
            ||||||||||||||||||||| |||| ||||||||||| | |||||||| ||| || |||
Sbjct: 362  acatagggcaattttcatgaagaaattgggcttttaaagttttttaaatgttttaaatgct 421

Query: 393  tttagacatgct 404
            ||||||||||||
Sbjct: 422  tttagacatgct 433

Score =  167 bits (84), Expect = 3e-37
 Identities = 132/149 (88%), Gaps = 1/149 (0%)
 Strand = Plus / Plus Query: 1    gcgagtgtctacgagcgaagttatgaaagttcgattcttcccccctctgaaaaaccgctt 60
            ||||||||||||||||||     ||||||||||||| ||||||| |||| |||||||||
Sbjct: 26   gcgagtgtctacgagcgactcaatgaaagttcgattattccccc-tctggaaaaccgctt 84

Query: 61   ttaaaaatattggctgctagatggtttttactatcgtgagcttttgcttttnnnnnnnca 120
            ||||||||||||||||||||||||||||||||||| ||||| ||||||||          ||
Sbjct: 85   ttaaaaatattggctgctagatggtttttactatagtgaggttttgcttttaaaaaaaca 144

Query: 121  cgagcgaagcgagttcatagttgcttttg 149
            |||||  |||||||||||||||||||||
Sbjct: 145  cgagcaaagcgagttcatagttgcttttg 173

>>>>nrnuc:GI_347602264 Gi|347602264|gb|JN541297.1| Uncultured bacterium plasmid clone
           S6GIO-28 genomic sequence. 0/0
           Length = 1214
 Score =  281 bits (142), Expect = 7e-72
 Identities = 157/162 (96%)
 Strand = Plus / Plus Query: 273  tttgaagaaattgccctcgactaagcttgcttagtcaaaaaagtttgagcaaagcgaaa 332
            ||||  |||||||||||||||||||||||||||||||||||||||||||||||||||||
Sbjct: 869  tttgcagaaattgccctcgactaagcttgcttagtcaaaaaagtttgagcaaagcgaaa 928

Query: 333  acatagggcaattttcatgatgaaaatgggcttttaaggcttttaaatgcttttaaggct 392
            ||||||||||||||||| ||||||||||||||||||| ||||||||||||||| |||
Sbjct: 929  acatagggcaattttcgtgatgaaaatgggcttttaatgttttttaaatgcttttaatgct 988

Query: 393  tttagacatgctgaaacgcaagcctagcaaggcatacagagg 434
            ||||||||||||||||||||||||||||||||||||||||||
Sbjct: 989  tttagacatgctgaaacgcaagcctagcaaggcatacagagg 1030

Score =  167 bits (84), Expect = 3e-37
 Identities = 132/149 (88%), Gaps = 1/149 (0%)
 Strand = Plus / Plus Query: 1    gcgagtgtctacgagcgaagttatgaaagttcgattcttcccccctctgaaaaaccgctt 60
            ||||||||||||||||||     ||||||||||||| ||||||| |||| |||||||||
Sbjct: 590  gcgagtgtctacgagcgactcaatgaaagttcgattattccccc-tctggaaaaccgctt 648

Query: 61   ttaaaaatattggctgctagatggtttttactatcgtgagcttttgcttttnnnnnnnca 120
            ||||||||||||||||||||||||||||||||||| ||||| ||||||||          ||
Sbjct: 649  ttaaaaatattggctgctagatggtttttactatagtgaggttttgcttttaaaaaaaca 708

Query: 121  cgagcgaagcgagttcatagttgcttttg 149
            |||||  |||||||||||||||||||||
Sbjct: 709  cgagcaaagcgagttcatagttgcttttg 737
```

FIGURE 4A

*HCBI4.296*     rmf.C2.F8E.2.31k  (2958bp)

```
CTGAGAAGCG AAGAAAAGAT GCGGTTTTGT GTATTGAACA TCTTGTGACT GCATCACCAG AATGGGACGG CTGGGGAACT
GAAAAAGAAA CTGCATTTTT TGAACAGTCA AGGAAATGGC TTGAAAGCAA ATATGGTAAA AAAAATGTGG TCAGTACAAC
GATTCATAGA GATGAAACAA CTCCACATTT AGTTGCGTAT GTTGTTCCCG TTGACGAAGA AACGGGACGT TTAAATGCTA
AAAAATTTAT TGGTGGATCT CGACATACAC TTTCACAGAT GCAGACTGAT TTTGCAGTTG AAGTAAAGGA TTTAGGATTA
GATCGCGGGG TACAGGGGAG CAAAGCAAAA CATACGTCTA TTCAAGAATA TTATGAAAAA TTGAACAATT ATGAGAATGA
ACCAGGTATT GAAAAAGGAC TCACCTATGA AGTGCCTGAA CCTGAGTTTT TTGAATCTAA AAATGTTTAC GGTGAGAGAG
TCGCAGAAGC TGTGGCTGCT CAGATAATTG ATCAAATTGC ACCTCGATTC GACAATGCTA ATTTATTGGC TAGTCAAACA
AAAAAATTAA AAAAAGAACT GTTAAACACT AGAAAAACGC TTGATGAAGT ACAGAAACGA GCAAAACCCT ATTTGGATAT
AATCAACGAA TATAATCATC CAAATCTTGA GAAAGAATTT AATAAGCAAG TTGCTAAATT AAAAGATAAT TTTGATTCAG
CACTTGACCA TCATAGATTC CTAAAAAGAC AGGAAGAACA AGAAAGATTT AACCAACAAC GTGAACTTCG CAATCAATTA
CACTTAGAGC AAGAGCAAAA AAAAACAACTG GTTGAGCAAG AAAGGCAAGA AAAAGAACGT TTAGCACTTT TAAGACGTCA
AGAATTAGAA AATCAGCGGA AAAATGAGCC TAAAAAACCT GATAATGGCA ATAATAACGA CTACTCACCC TCATAATACC
CGTTTAAACG CAAAAAAAC GGGGGTTTTA GCCCTGTTTG GCCTTTTATG CATAAAAGTA TAATTGAAAT AAAAAAATGC
TCTTAGAACG CAAATGATGA GCATTTAGCG AGTGTCTACG AGCGACACAA TGAAAATTCG CCTATTCCCC CTCTGAAAAA
CTGCTTTTGC TCTTTTTTGC TTCTGGAGAG ACTTGTTAGC GAGTGTCTAC GAGCGAAGTA TTGATGCTTT TGCTCTTAAA
AAAGCATCAG CATAGCGAAT GCATTATCTA TGCTTTTGAC TTTGATTTTG CTCTTGAAAC GACACGAGCA ACGCGAGTGC
CATAGCCTTT GATTTTGCCT TTTTTGGGCT TTTAATGTTT TTAAATGCTT TTAAATGCTT TTAGATAGCC TGAAAGCATT
GCTATACATA TGTTTCAGAG CTTATAAAGA TACAGATTCC TTGCTATAAA GATACAGATT CCTTGCTATA AAGATACAGA
TTCCTTGCTA TAAAGATACA GATTCCTTGC ATTAAGGTAC ATAGTCATAT AATGTATCTT TTAATACATG ATTGTATGAA
ATAACTAATA TGAAAAATGG GTTAGTAGTG AAAGATAATG CGTTAATGAA TGCCAGCTAT AATTTAGAAG TAACAGAACA
GCGCTAATA CTTCTAGCAA TCATTAGTGC AAGAGAAACA GGGCAAGGGA TTACGTCAGA TAGCAAATTA GAAATACATG
CTAGTGACTA AACAAGCAA TTCAGTGTTG CAAAAGAAAC AGCTTATGAG GCACTAAAAA GTGCTGTAAA TAATTTATTT
GAGCGTCAAT TTTCATTTAG AGAAGAAACA AAAAAAGGCA CTGGCATTGT ACGGTCACGA TGGGTTAGCA GAATTAAATA
CATTGATGAC GCAGCAATAC TTGAAATCAC TTTTGCGCCT GACGTTGTAC CATTAATCAC TAGACTTGAA GAACACTTCA
CAAGTTATCA AATCAAGCAA ATAGCACAGC TTACAAGTAA GTACGCTATC CGTTTATATG AACTTCTTAT TGCCTGGGCA
ACTACAGGCA AAGTCCCTGA GCTTGAACTA TCAGAATTTA GAAATAGATT AGGCATGCT AGTAATGAAT ACACAGCAAT
GAACAACTTT AAAAGCCGTG TATTAGAGCC GTCTATTAAG CAGATCAATG AACACACAGA CATTACTGTG ACGTATGAAC
AGCATAAAAA AGGGCGGACA ATTACAGGCT TTTCATTCAG ATTTAAGCAG AGGCAACAAG CAAAAAAAAT AGAAACTAAC
AGAGATCCAA ACACACCTGA CTTTTTTATC AAAATGACCG ATGCTCAACG GCATTTATTC GCTAACAAAA TGTCTGAAAT
GCCCGAAATG GGGAAATACT CACAAGGTAC AGAAAGCTAC CAACAATTCG CTATTCGCAT CGCCGACATG CTTTTACAAC
CTGAAAAATT CAGAGAGCTT TATCCAATTT TAGAAAAAGC CGGATTCAAA GAATGATTGA AAAAGAGATA ACAAAATTTG
AGAAAGAGAT TTTGCTACAA GACAAAATCT CTCAGCTCGA AAATGAACTA AAAGAATTTT CTGATCTTCA AAAAAAAGCA
TATAGCGAAC GGCTTCAAAA AAGTATCGTG GGTTTAGAAA ATAGAATCTA TCGAATCAAG AAAATGCTTT ATACAACCTG
AAAGTTTGTC GGGAGGATTC CCCTTACTCA TGAACTTTCA ATGTACCTTT AGGTGCTTTG AAAGTGGAGT
GAGTCCACTT CGCTATCGCA AAGCTCAAAA ACCTCTGCTA TCGTGTGTTT TTTCGGTATC GGATTTATCA AATGTCATTT
GCTATTTTGC GTATTCAAAA ATTGAAATCG TTTGCAGACG TTGGCGGTAG TCTTTCCGAT AATTATCGCA ATCGAGAAAC
GTTAAATGCA GATGATGCTC GTACTCATTT GAATGAACAT ACGCTAGATA CAAACGAAAA ATGTATGTCC GCAATCAG
```

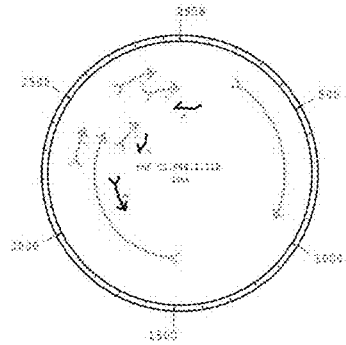

69% nucleotide similarity to Acinetobacter baumannii SDF plasmid p3ABSDF (24922bp) in
    1361nt overlap
70% nucleotide similarity to Acinetobacter baumannii ATCC 17978 plasmid pAB1
    (13408bp) in 964bp overlap

ORFs:
*308 amino acids    58% similarity to Sphinx1.76 (324 aa)    replication protein*
*225 amino acids         mobilization protein (mob)*

*308 amino acids    58% similarity to Sphinx1.76 (324 aa)    replication protein*

FIGURE 4B

```
                      1                                                  50
SPHINX1.76.324.PEP   -MSDLIVKDN ALMNASYNLA LVEQRLILLA IIEARETGKG INANDPLTVH
HCBI4.296.308.pep    MKNGLVVKDN ALMNASYNLE VTEQRLILLA IISARETGQG ITSDSKLEIH 51                                                 100
SPHINX1.76.324.PEP   AGSYINQFNV QRHTAYQALK DACKDLFARQ FSYQEKRERG RINITSRWVS
HCBI4.296.308.pep    ASDYAIQFSV AKETAYEALK SAVNMLFERQ FSFREETKKG TGIVRSRWVS 101                                                150
SPHINX1.76.324.PEP   QIGYMDDTAT VEIIFAPAVV PLITRLEEQF TQYDIEQISG LSSAYAVRMY
HCBI4.296.308.pep    RIKYIDDAAI LEITFAPDVV PLITRLEEHF TSYQIKQIAQ LTSKYAIRLY 151                                                200
SPHINX1.76.324.PEP   ELLICWRSTG KTPIIELDEF RKRIGVLDTE YTRTDNLKMQ VIELALKQIN
HCBI4.296.308.pep    ELLIAWRTTG KVPELELSEF RNRLGIASNE YTAMMNFKSR VLEPSIKQIN 201                                                250
SPHINX1.76.324.PEP   EHTDITASYE QHKKGRVITG FSFMFKHKKQ NSDKTPDTNA SSPR.IVKHS
HCBI4.296.308.pep    EHTDITVTYE QHKKGRTITG FSFRFKQKQQ AKKIETNRDP NTPDFFIKMT 251                                                300
SPHINX1.76.324.PEP   QIPTNIVKQP ENAKMSDLEH RASRVTGEIM RNRLSDRFKQ GDESAIDMMK
HCBI4.296.308.pep    DAQRHLFAN. ...KMSEMPE MG....... ......KYSQ GTESYQQFAI 301             326
SPHINX1.76.324.PEP   RIQSEIITDA IADQWESKLE EFGVVF
HCBI4.296.308.pep    RIADMLLQPE KFRELYPILE KAGFKE
```

*FastA \*Geall*

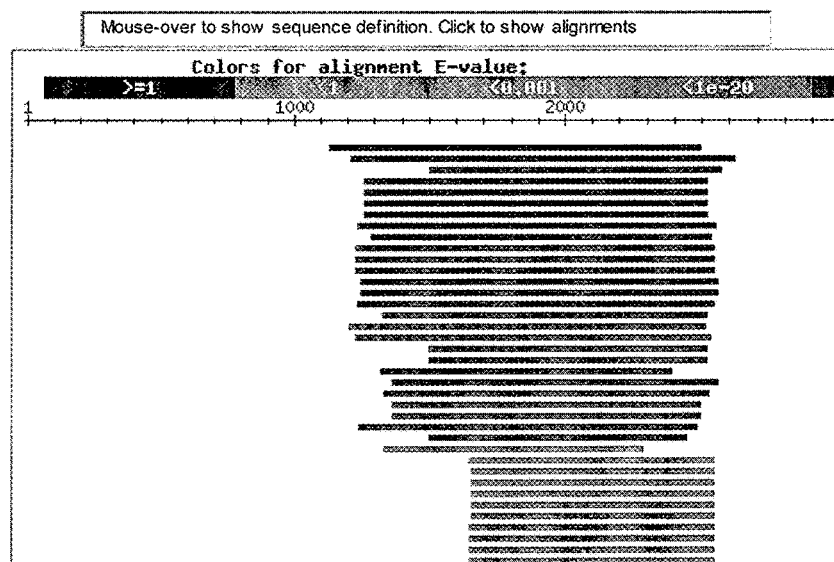

```
EMHTG_HUM:AL391558    Begin: 42149  End: 43446  Strand: -
! Al391558 Human DNA sequence *** SEQ...  1068  2897  2878  2016.7  2.3e-108
EMSTD_PRO:CU468233    Begin: 275    End: 1601
! Cu468233 Acinetobacter baumannii SD...  1182  3120  2725  1914.3  1.1e-101
EMSTD_PRO:CP000522    Begin: 1      End: 957
! Cp000522 Acinetobacter baumannii AT...   946  1947  2123  1492.1  6.9e-78
EMSTD_PRO:EF138630    Begin: 121    End: 1303
! Ef138630 Acinetobacter baumannii is...   570  1739  2096  1473.3  8.4e-77
EMSTD_PRO:JX069966    Begin: 90     End: 1272
```

FIGURE 4C

```
! Jx069966 Acinetobacter baumannii pl...   570  1739  2096  1473.6   9.1e-77
EMSTD_PRO:CP002523      Begin: 953 End: 2135
! Cp002523 Acinetobacter baumannii TC...   570  1876  2096  1474.1   1.1e-76

EMHTG_HUM:AL391558
ID   AL391558; SV 6; linear; genomic DNA; HTG; HUM; 237855 BP.
AC   AL391558;
DE   Human DNA sequence * SEQUENCING CANCELLED * from clone RP11-192D3
KW   HTG; HTGS_CANCELLED; HTGS_PHASE1. . . .
SCORES    z-score: 2016.7 E(): 2.3e-108
>>EMHTG_HUM:AL391558                                              (237855 nt)
 70.4% identity in 1310 nt overlap
 (2463-1172:42149-43446)

2490      2480      2470      2460      2450      2440
rmf.C2.F8E.2 AAAATCTCTTTCTCAAATTTTGTTATCTCTTTTTCAATCATTCTTTGAATCCGGCTTTTT
                                    ||||  |  ||   ||    ||  ||   ||||||
AL391558     TTCTAAAGAAAAGGTCATTTTAACTGAATGTTTTAATTTATGGTTGAAAACCAACTTTTT
                 42120     42130     42140     42150     42160     42170

2430      2420      2410      2400      2390      2380
rmf.C2.F8E.2 CTAAAATTGGATAAAGCTCTCTGAATTTTTCAGGTTGTAAAAGCATGTCGGCGATGCGAA
             ||||||  ||||| || ||||| ||||||||||||| | ||| | ||| |  ||||| || |
AL391558     CTAAAACAGGATACAGTTCTCTAAATTTTTCAGGCTCTAACAACATATTTGCGATACGTA
                 42180     42190     42200     42210     42220     42230

2370      2360      2350      2340      2330      2320
rmf.C2.F8E.2 TAGCAAATTGTTGGTAGCTTTCTGTACCTTGTGAGTATTTCCCCATTTCGGGCATTTCAG
              | |||||||||| |||||||  ||||| ||||| |||||||||||||||||||||||||
AL391558     TGGCAAATTGTTGATAGCTTTCCGTACCCTGTGAATACTTCCCCATTTCGGGCATTTCAG
                 42240     42250     42260     42270     42280     42290

2310      2300      2290      2280      2270      2260
rmf.C2.F8E.2 ACATTTTGTTAGCGAATAAATGCCGTTGAGCATCGGTCATTTTGATAAAAAAGTCAGGTG
             ||||||| || || ||||||||| ||| ||||||||||||||| ||||||||||| |||
AL391558     ACATTTTATTTGCAAATAAATGACGTTGTGCATCGGTCATTTTGACAAAAAAATCAGGGG
                 42300     42310     42320     42330     42340     42350

2250      2240      2230      2220      2210      2200
rmf.C2.F8E.2 TGTTTGGATCTCTGTTAGTTTCTATTTTTTTTGCTTGTTGCTTCTGCTTAAATCTGAATG
              | |||||| |   ||| ||||  |    |||  |     ||||| |  |||||| |||||
AL391558     TATTTGGATCACGTTTAATTTCAA---CTTTCGGCTGTTGTTTATGCTTAAATTTGAATG
                 42360     42370     42380     42390     42400     42410

2190      2180      2170      2160      2150      2140
rmf.C2.F8E.2 AAAAGCCTGTAATTGTCCGCCCTTTTTATGCTGTTCATACGTCACAGTAATGTCTGTGT
             ||||  |||||   ||  ||  |||||||| |||||||||||||   ||   | ||||||| |
AL391558     AAAACCCTGTGATGGTACGCCCTTGTTTATGCTGTTCATAAGTTGCTTTTATGTCTGTAT
                 42420     42430     42440     42450     42460     42470

2130      2120      2110      2100      2090      2080
rmf.C2.F8E.2 GTTCATTGATCTGCTTAATAGACGGCTCTAATACACGGCTTTTAAAGTTGTTCATTGCTG
              | |||||||||  ||||||| || ||||  |  | ||||||||||||  | | |      |
AL391558     GCTCATTGATTTGAGTAATAGCTGTTTCTAGTACACGGCTTTTAAAATGGTGCATACGTT
                 42480     42490     42500     42510     42520     42530

2070      2060      2050      2040      2030      2020
rmf.C2.F8E.2 TGTATTCATTACTAGCTATGCCTAATCTATTTCTAAATTCTGATAGTTCAAGCTCAGGGA
                 ||  |||| |  |  |||||| | |||  |    | ||  |||||||          ||
AL391558     GATACTCATCATCGTCCACACCTAAGTTTTTACGTAGCTGTTGCAGTTCAAAGGTTGGCG
                 42540     42550     42560     42570     42580     42590

2010      2000      1990      1980      1970      1960
rmf.C2.F8E.2 CTTTGCCTGTAGTTCGCCAAGCAATAAGAAGTTCATATAAACGGATAGCGTACTTACTTG
             ||| ||       |||||||||  || |  | ||||||| |  |   | ||||||||||||| |
AL391558     TTTTTCCAACTTCACGCCAAGCGATTAATAATTCATAAAGTCTAGTGGCGTACTTACTCG
                 42600     42610     42620     42630     42640     42650

1950      1940      1930      1920      1910      1900
rmf.C2.F8E.2 TAAGCTGTGCTATTTGCTTGATTTGATAACTTGTGAAGTGTTCTTCAAGTCTAGTGATTA
             |  ||  ||||| |  |||  |||  |  |||  ||     ||||||||  |||||  |||||||
AL391558     TTAGGTGTGCAACTTGTTTCGCTTCATATTTTGTAAAATGCTCTTCCAATCGAGTGATTA
                 42660     42670     42680     42690     42700     42710

1890      1880      1870      1860      1850      1840
rmf.C2.F8E.2 ATGGTACAACGTCAGGCGCAAAAGTGATTTCAAGTATTGCTGCGTCATCAATGTATTTAA
             |  |||||||  || |||| |  ||||| ||||| |||| ||||  |||||||  |  ||
AL391558     AAGGTACTACATCAGGTGCGAAAGTAATTTCTAGTAATGCTAAGTCATCTACATAAAAAA
                 42720     42730     42740     42750     42760     42770
```

FIGURE 4D

```
              1830      1820      1810      1800      1790
rmf.C2.F8E.2 TTCTGCTAACCCATCGTGACCGTACAATGCC-AGT----GCCTTTTTTTGT-TTCTTCTC
             | |  ||||||||| ||  || || ||||| ||| |     | || |||| | ||| |
AL391558     TACGGCTAACCCAACGAGAGCGAACAATACCTACTTTCCCCGTTCTTTTATATTCAGCCG
              42780     42790     42800     42810     42820     42830

1770      1760      1750      1740      1730
rmf.C2.F8E.2 TAAATGAAAATTGACGCTCAAATAAATTATTTACAGCACTTTTTAGTGCCTCATAAGCTG
             || |   ||| || |  | ||| | ||| ||||||||   ||||||  || |  ||| ||
AL391558     TATAGCTAAACTGTCTATTAAACAGATTGTTTACAGCTTCTTTTAGGGCTTTATAGGATG
              42840     42850     42860     42870     42880     42890

1710      1700      1690      1680      1670
rmf.C2.F8E.2 TTTCTTTTGCAACACTGAACTGAATTGCATAGTCACTAGCATGTATTTCTAATTTGCTAT
              |||     |  ||| || ||   |||||||  |||||||||||||||||| ||||||||
AL391558     CATCTGGCGACACATTAAATAGCTTTGCATAATCACTAGCATGTATTTCTAGTTTGCTAT
              42900     42910     42920     42930     42940     42950

1650      1640      1630      1620      1610
rmf.C2.F8E.2 CTGACGTAATCCCTTGCCCTGTTTCTCTTGCACTAATGATTGCTAGAAGTATTAAGCGCT
             ||| ||| || || |||||| |||  ||||||  || ||||| |||| |||||| ||||
AL391558     CTGCCGTGATTCCCTGCCCTAATTCCCTTGCATTAATTATTGCCAGCATAATTAAACGCT
              42960     42970     42980     42990     43000     43010

1590      1580      1570      1560      1550
rmf.C2.F8E.2 GTTCTGTTACTTCTAAATTATAGCTGGCATTCATTAACGCATTATCTTTCACTACTAACC
             ||||||||| |||||||||||| ||||| ||  || || ||| ||| |||||||||||
AL391558     GTTCTGTTAGTTCTAAATTATAACTTGCGTTTATTAATGCATTATCTTTCACAACTAAAC
              43020     43030     43040     43050     43060     43070

1530      1520      1510      1500      1490
rmf.C2.F8E.2 CATTTTTCATATTAGTTA---TTTCATACAATCATGTATTAAAAGA-TACATTATATGAC
             ||||  ||||||| ||      || ||   ||  || || |  || |  ||||  ||| |
AL391558     CATTCTTCATATTAAATACACGTTATTATTAATGTGTATTTACACACTAC---ATAT-AA
              43080     43090     43100     43110     43120     43130

1480      1470      1460      1450      1440      1430
rmf.C2.F8E.2 TATGTACCTTAATGCAAGGAATCTGTATCTTTATAGCAAGGAATCTGTATCTTTATAGCA
             |||||   ||||| ||||  |||  |   ||||  | |||| |||  |   ||||  |
AL391558     TATGTGTGTTAATCAAGAGAATTTGTGTGCTTATACAAGAGAATTTGTGTGCTTATACAA
               43140     43150     43160     43170     43180     43190

1420      1410      1400      1390      1380      1370
rmf.C2.F8E.2 AGGAATCTGTATCTTTATAGCAAGGAATCTGTATCTTTATAAGCTCTGAAACATATGTAT
             |||| ||| |  ||||| | |||| ||| ||| |  |||||    ||||||||| ||  ||
AL391558     GAGAATTTGTGTGCTTATACAAGAGAATTTGTGTGCTTATATAGGCTGAAACATACTGAT
              43200     43210     43220     43230     43240     43250

1360      1350      1340      1330      1320      1310
rmf.C2.F8E.2 AGCAATGCTTTCAGGCTATCTAAAAGCATTTAAAAGCATTTAAAAACATTAAAAGCCCAA
             | |||||||||||| |||| ||||||||||||||||||| || |||| |||||||||| ||
AL391558     ATCAATGCTTTCAGCTAGTCTAAAAGCATTTAAAAGCTTTAAAAATAATTAAAAGCCTAA
              43260     43270     43280     43290     43300     43310

1300      1290      1280      1270      1260
rmf.C2.F8E.2 -AAAAGGCAAAATCAAAGGCTAT-GGCACTCGC-GTTGCTCGT-GTCGTTTCAAGAGC--
              |||  |||  ||  | || |||||   ||||||  ||  ||   |  |
AL391558     CGGCAGGGGAGTACAACTGCCCTAGGTACTCGCTAAAGCTCGTACTCTATTGCTGTTCGC
              43320     43330     43340     43350     43360     43370

1250      1240      1230      1220      1210      1200
rmf.C2.F8E.2 -AAAATCAAAGTCAAAAGCATAGATAATGCATTCGCTATGCTCATGCTTTTTTAAGAGCA
              ||| || |   |||  | ||   |  | ||   ||||| |||| ||||
AL391558     TCTGCTCACAGCGAGGGGCAGTTTTGGTTAATTCTATTTGTGAA-----ATTTAAAAGCA
              43380     43390     43400     43410     43420

1190      1180      1170      1160      1150      1140
rmf.C2.F8E.2 AAAGC-ATCAATACTTCGCTCGTAGACACTCGCTAACAAGTCTCTCCAGAAGCAAAAAAG
             ||||| || |  | ||||||
AL391558     AAAGCAATTATGAATTCGCTACGCTCATAAACCTTTTTTACTCGCTTACGCTCGATCATG
              43430     43440     43450     43460     43470     43480
```

EMSTD_PRO:CU468233
ID    CU468233; SV 1; circular; genomic DNA; STD; PRO; 24922 BP.
AC    CU468233;
*DE   Acinetobacter baumannii SDF plasmid p3ABSDF, complete genome. . . .*
SCORES  Init1: 1182  Initn: 3120  Opt: 2725  z-score: 1914.3 E(): 1.1e-101

FIGURE 4E

```
>>EMSTD_PRO:CU468233                                        (24922 nt)
 initn: 3120 init1: 1182 opt: 2725 Z-score: 1914.3 expect(): 1.1e-101
   69.1% identity in 1361 nt overlap
 (1239-2569:275-1601)

EMSTD_PRO:CP000522
ID   CP000522; SV 1; circular; genomic DNA; STD; PRO; 13408 BP.
AC   CP000522;
DE   Acinetobacter baumannii ATCC 17978 plasmid pAB1, complete sequence. . .
SCORES    z-score: 1492.1 E(): 6.9e-78
>>EMSTD_PRO:CP000522                                         (13408 nt)
   69.6% identity in 964 nt overlap
 (1530-2484:1-957)

EMSTD_PRO:EF138630
ID   EF138630; SV 1; linear; genomic DNA; STD; PRO; 12200 BP.
AC   EF138630;
DT   12-MAY-2007 (Rel. 91, Created)
DT   27-JUN-2007 (Rel. 92, Last updated, Version 3)
DE   Acinetobacter baumannii isolate 186 plasmid pOUR, partial sequence.
KW   . . . .
initn: 1739 init1: 570 opt: 2096 Z-score: 1473.3 expect(): 8.4e-77
   65.1% identity in 1198 nt overlap
 (1292-2484:121-1303)

EMSTD_PRO:JX069966
ID   JX069966; SV 1; circular; genomic DNA; STD; PRO; 10879 BP.
AC   JX069966;
DE   Acinetobacter baumannii plasmid pAB120, complete sequence.
KW   . . . .
SCORES     z-score: 1473.6 E(): 9.1e-77
>>EMSTD_PRO:JX069966                                         (10879 nt)
   65.1% identity in 1198 nt overlap
 (1292-2484:90-1272)
```

FIGURE 5A

*HCBI5.173*    *rmf.C2.F8E.5.23kr  (1732 bp)*

```
CCATTAGCTT TATAGTGCCA AGTAATATCT AGTAAACGGA TATGTTTTAT ATGATCTTTT CTTTGAAAAT GAAGAATCAT
ATCTGAGGTC GAATAGTTGT TATATTTACT TTTTACGTAA TCAGCATAC CGATATGATA ATGCCAAAGA TTATTCGAAT
ATGTGAAATC ATAGATTGGA TCAGTTTTGT CTATTCCACG CCATGAAGGT GCAATTTTAC CTTGGTATTT AGAAAAATCC
TTTAAACCAA ACTCTTCATA GATATCAGTG AAATCTAAAA TTTTTATCTTG TTGATCTTCA GGATAACGCC CAAATTGAAC
TGCAAATTGT TTTCCAAATT CCCAAGAGTA AGACAATTAC TTTTTCCCTG CTTCTAATAT TAATCTTCTT TTCTCTTCTC
TGCTTAAACC TTGAGGCATA ACAAAGGTTT CTGAATCAAG AGCTGATTTC ATTCTATCAA GATTAATACG AACAGGTGCT
GTTTTTTGAT TTGATGTTTG GGTAATAACG AAGCCCATTA CATTCATTTG CCACCTCGAC AAATAAAAAT TTCTTTTAAA
ATTTTAACAA AAAAAATAGC GTAGCGGGTT TTTAATTGTT TTTAAATACT TTTAATTGTT TTTAGACCTG CTGAAACCCG
CTATACAAAA GGCTTTCAGG CCATATAAAA AGACATTTAC CCTGCCATAA AAAGACATTT ACCCTGCCAT AAAAAGACAT
TTACCCTGCC ATAAAAAGAC ATTTACCCTG CTAAAAAGA CATTTTACAA AATGTCTTTT TAATGGTAGC TTTAGGTTGT
TTTTTATAAA AAAAATTGGC GTTAAAAAAA TATGGATTTA GTCGTTAAAG ATAATAATTT GATCAATGCT AGCTACTCCC
TAGGTTTGGT TGAGCAACGT CTTGTATTGC TAGCTATCAT TGAAGCTAGA GAATCTAGTA AGGGGATAGA TTCAGAAACA
TTNTTAGAAA TACATGCTCA ACACTATGCA GATAGATTTG ATGTAAATGT AAAAAATACG TATGCCATGC TTTCAGAGGC
GGCACAGACT CTTTTTAATC GTCAAGTCAC TTACATGATG GTTGATGAAA AAAGGAATAA ACCTGAAAAG CGTGTAATTC
GCTGGGTTAG TGGTATTTCA TATGTAGAAG GGGCTGGAGT TCTTAAACTT CGTTTTTCTC CAGAAATTGT CCCTCTAATA
ACTAGGCTAG AGCAAAATTT TACGAGTTAT GAACTAGAAC AAGTTAAAAG CTTAAACGTA TATGCAACTC GACTATATGA
ATTATTAGTC TGTTGGCGTA GTACAGGTAA AACTCCCATT ATTGAAATAG AAGATTTTCG TTCAAAAATA GGAGTCTTAC
CTACTGAATA TAAAATTAATG AGTGATTTCA AAAAGCGAGT TTTTGAGCCA GCAATACAGC AAATTAATAA AAACACAGAT
TTGACGGTTA ATTATGATCA ACATAAATCA GGCCGTACAA TTACAGGCTT CTCATTTAAA TTTAAGCAAA AGAAAACGAA
ATCAGAAAAG GTCGTAACCG CTAAACGAGA CCCAAATACA CCTGACTTTT TTGTAAAAAT GACCGATTCC CAACGTCATT
TATTCGCAAC TAAACTTTCT GAAATGCCAG AGATGTCTAA ATATTCTCAA GGTACAGAGT CGTATCAACA GTTTGCTATC
CGTATTGCCG ATATGCTTTT AGAACCTGAA AAGTTAAAGA ATTCGAGCTC NG
```

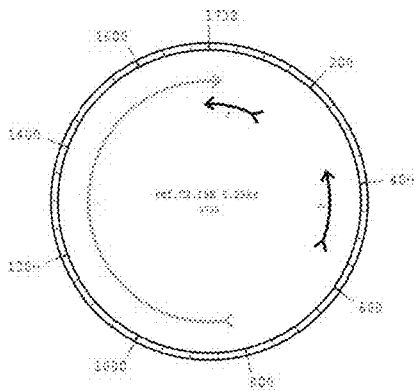

*Nucleotide sequence similarities to:*
Dendroctonus ponderosae genomic DNA (GI_462465081)    70% in 605bp
Acinetobacter baumanii SDF plasmid p3ABSDF (GI_169150781)    74% in 367bp, 72% in 403 and 77% in 71bp

*ORF:*
310 amino acids    49% similarity to Sphinx1.76 (324aa)    replication protein

```
                        1                                                   50
    SPHINX1.76.324.PEP  MSDLIVKDNA LMNASYNLAL VEQRLILLAI IEARETGKGI NANDPLTVHA
    HCBI5.296.310.pep   -MDLVVKDNN LINASYSLGL VEQRLVLLAI IEARESSKGI DSETKLEJHA 51                                                  100
    SPHINX1.76.324.PEP  GSYINQFNVQ RHTAYQALKD ACKDLFARQF SYQEKRERGR ..INITSPWV
    HCBI5.296.310.pep   QHYADRFDVN VKNTYAMLSE AAQTLFNRQV TYMMVDEKRN KPEKRVIRWV 101                                                 150
    SPHINX1.76.324.PEP  SQIGYMDDTA TVEIIFAPAV VPLITRLEEQ FTQYDIEQIS GLSSAYAVRM
    HCBI5.296.310.pep   SGISIVEGAG VLKLPESPEI VPLITRLEQN FTSYELEQVK SLN.VYATRI 151                                                 200
    SPHINX1.76.324.PEP  YELLICWRST GKTPIIELDE FRKRIGVLDT EYTPTDNLKM QVIELALKQI
    HCBI5.296.310.pep   YELLVCWRST GKTPIIEIED FRSKIGVLPT EYKLMSDFKK RVFEPAIQQI 201                                                 250
```

FIGURE 5B

```
SPHINX1.76.324.PEP   NEHTDITASY EQHKKGRVIT GFSFMFKHKK QNSDKTPDTN ASSPRIVKHS
HCBI5.296.310.pep    NKNTDLTVNY DQHKSGRTIT GFSFKFKQKK TKSEKVVTAK RDP.......

251                                             300
SPHINX1.76.324.PEP   QIPTNIVKQP ENAKMSDLEH RASRVTGEIM RNRLSDRFKQ GDESAIDMMK
HCBI5.296.310.pep    NTPDFFVKMT D....SQRHL FATKLS.... EMPEMSKYSQ GTESYQQFAI 301              326
SPHINX1.76.324.PEP   RIQSEIITDA IADQWESKLE EFGVVF
HCBI5.173.299.pep    RIADMLLE.. .....PEKLK NSH~~~
```

*FastA \*Geall*

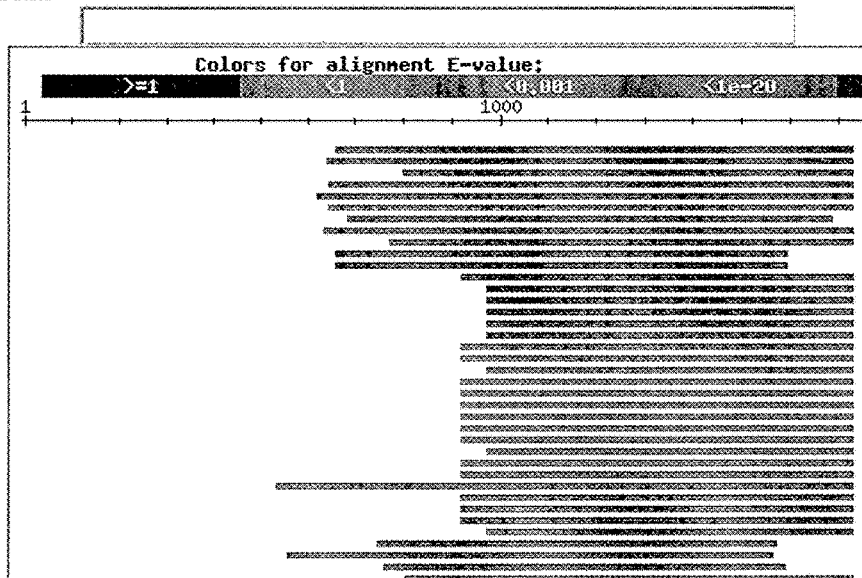

```
EMSTD_PRO:GU978996    Begin: 1    End: 1025
! Gu978996 Acinetobacter baumannii pl...  459  1221  1633  994.9  4.3e-49
EMSTD_PRO:GU978999    Begin: 30   End: 1085
! Gu978999 Acinetobacter baumannii pl...  554  1233  1613  982.7  1.9e-48
EMSTD_PRO:CP000522    Begin: 4    End: 893
! Cp000522 Acinetobacter baumannii AT...  531  1254  1504  908.7  2.1e-45
EMSTD_PRO:DQ278485    Begin: 1    End: 1049
! Dq278485 Acinetobacter venetianus s...  377   683  1445  873.8  2.3e-43
EMSTD_PRO:GU979001    Begin: 8    End: 1085
! Gu979001 Acinetobacter baumannii pl...  402   733  1453  886.1  4.7e-43
EMSTD_ENV:JN098514    Begin: 1    End: 1049
! Jn098514 Uncultured bacterium plasm...  377   683  1445  877.8  4.7e-43
EMSTD_PRO:GQ861437    Begin: 7    End: 910  Strand: -
! Gq861437 Acinetobacter baumannii st...  525  1189  1441  874.7  5.7e-43
EMSTD_PRO:CU468231    Begin: 323  End: 1369
! Cu468231 Acinetobacter baumannii SD...  484  1069  1395  845.5  1.6e-41
EMSTD_PRO:AY541809    Begin: 19   End: 944
```

```
EMSTD_PRO:GU978996
ID    GU978996; SV 1; linear; genomic DNA; STD; PRO; 1065 BP.
AC    GU978996;
DE    Acinetobacter baumannii plasmid p736 plasmid replication protein Aci 7
DE    (repA) gene, complete cds. . . . .
SCORES  z-score: 994.9 E(): 4.3e-49
>>EMSTD_PRO:GU978996                                    (1065 nt)
  63.2% identity in 1034 nt overlap
  (688-1709:1-1025)
              660        670        680        690        700        710
rmf.C2.F8E.5  AGGCCATATAAAAAGACATTTACCCTGCCATAAAAGACATTTACCCTGCCATAAAAGA
                                      ||||| || |||||| ||| ||||| ||
GU978996                              TAAAACGAGGTTTACCTTGCATTAAAACGA
                                               10         20         30

720        730        740        750        760        770
rmf.C2.F8E.5  CATTTACCCTGCCATAAAAGACATTTACCCTGC-TTAAAAGACATT----TTACAAAA
```

FIGURE 5C

```
             ||||||  |||  |||||  ||  ||||||  |||  ||||||  ||  ||       ||  ||   |
GU978996     GGTTTACCTTGCATTAAAACGAGGTTTACCTTGCATTAAAACGAGGTTTACCTTGCATTA
                 40        50        60        70        80        90

780       790       800       810       820       830
rmf.C2.F8E.5 TGTCTTTTTAATGGTAGCTTTAGGTTGTTTTTTATAAAAAAAATTGGCGTT--AAAAAAA
             ||  ||  |||||  ||        ||  |  ||  |||||  ||  ||   ||  |  ||
GU978996     AG-CGAGTTAATAATATAACCTCGTCTTATTAAATTAAAAACATAATCTTTTCATATGAA
                100       110       120       130       140

840       850       860       870       880       890
rmf.C2.F8E.5 TATGGATTTAGTCGTTAAAGATAATAATTTGATCAATGCTAGCTACTCCCTAGGTTTGGT
             |  ||  ||  |  ||||||||||||  ||  ||  |||||  ||  ||   |||  |  |  ||
GU978996     AACAGAACTAATAGTTAAAGATAATGCCTTAATTAATGCCAGTTATAACCTTGATCTAGT
                150       160       170       180       190       200

900       910       920       930       940       950
rmf.C2.F8E.5 TGAGCAACGTCTTGTATTGCTAGCTATCATTGAAGCTAGAGAATCTAGTAAGGGGATAGA
             ||||||||   |    |    |   ||||   |||   |||||||   ||  |||||   ||||   ||  |||   |
GU978996     GGAGCAACGGTTAATTCTTTTAGCGATCCTTGAAGCAAGGGAATCGGGTAAAGGAATAAA
                210       220       230       240       250       260

960       970       980       990       1000      1010
rmf.C2.F8E.5 TTCAGAAACATTNTTAGAAATACATGCTCAACACTATGCAGATAGATTTGATGTAAATGT
             |  |    |        |||   ||   |  |   ||||||   |||        ||   |||||||   |||
GU978996     TGCTAATGATCCTTTAACAGTTCATGCTGAAAGTTATATCAATCAATTTGGTGTTCATCG
                270       280       290       300       310       320

1020      1030      1040      1050      1060
rmf.C2.F8E.5 AAAAAATACGTATGCCATGCTTT--CAGAGGCGGCACAGACTCTTTTTAATCGTCAAGTC
             |||  |  |||  ||  ||  ||   |||  ||      |   |||  ||       |  |||  |
GU978996     AAATACGGCTTAT--CAAGCATTAAAAGATGCTTGTGATGATCTATTCGTAAGACAATTT
                330       340       350       360       370       380

1070      1080      1090      1100      1110      1120
rmf.C2.F8E.5 ACTTACATGATGGTTGATGAAAAAAGGAATAAACCTGAAAAGCGTGTAATTCGCTGGGTT
             |  |||       |       ||  |||||||  |  |||       |        ||  |       |  |||||
GU978996     AGTTATCAAAGCCTTAGTGAAAAAGGAAAT---GTTATTAATCACAAATCAAGATGGGTG
                390       400       410       420       430       440

1130      1140      1150      1160      1170      1180
rmf.C2.F8E.5 AGTGGTATTTCATATGTAGAAGGGGCTGGAGTTCTTAAACTTCGTTTTTCTCCAGAAATT
             ||||      ||   |  |||   ||   ||          ||||   |  |||   |   |||
GU978996     AGTGAGGTTGCTTATATTGATAACGAGGCTGTCGTTAGACTTATCTTTGCTCCCGCTATT
                450       460       470       480       490       500

1190      1200      1210      1220      1230      1240
rmf.C2.F8E.5 GTCCCTCTAATAACTAGGCTAGAGCAAAATTTTACGAGTTATGAACTAGAACAAGTTAAA
             ||  |||  ||||  |||||  |||||   ||  |  |||||  |    ||||||  ||  ||||||   |  |
GU978996     GTGCCTTTAATTACTAGACTAGAAGAACAATTTACAAAGTATGAAATACAACAAATAAGC
                510       520       530       540       550       560

1250      1260      1270      1280      1290      1300
rmf.C2.F8E.5 AGCTTAA-ACGT--ATATGCAACTCGACTATATGAATTATTAGTCTGTTGGCGTAGTACA
             |   |||||  |  ||       |||||  |||    |||||||||   |||||  |        |||||||||||
GU978996     AATTTAACAAGTGCTTATGCCGTTCGTTTATATGAAATATTAATTGCATGGCGTAGTACC
                570       580       590       600       610       620

1310      1320      1330      1340      1350      1360
rmf.C2.F8E.5 GGTAAAACTCCCATTATTGAAATAGAAGATTTTCGTTCAAAAATAGGAGTCTTACCTACT
             ||  |||||  ||   |  ||           |    |    ||  ||       |  |||||||  ||||
GU978996     GGAAAAACGCCTCTCATAACCCTGTACGACTTCAGACAAAAAATAGGTGTACTCGATACT
                630       640       650       660       670       680

1370      1380      1390      1400      1410      1420
rmf.C2.F8E.5 GAATATAAATTAATGAGTGATTTCAAAAAGCGAGTTTTTGAGCCAGCAATACAGCAAATT
             |||||  |||  ||||  ||||||  |||||        ||  ||  ||        |||  ||  |  |||   |
GU978996     GAATACAAACGAATGTATGATTTTAAAAAATATGTCTTGGACATTGCATTAAAACAAGTC
                690       700       710       720       730       740

1430      1440      1450      1460      1470      1480
rmf.C2.F8E.5 AATAAAAACACAGATTTGACGGTTAATTATGATCAACATAAATCAGGCCGTACAATTACA
             |||  ||  |  |  |||  |  ||  |         |||  ||  |||||   |  |||   |        |||||||
GU978996     AATGAACATACCGATATTACTGTCAAAGTTGAACAGCATAAGACGGGCAGATCAATTACT
                750       760       770       780       790       800

1490      1500      1510      1520      1530      1540
rmf.C2.F8E.5 GGCTTCTCATTTAAATTTAAGCAAAAGAAAACGAAATCAGAAAAGGTCGTAACCGCTAAA
             |||||  |||||||||  |||||  |||||||  ||       |       |  |        ||||  |        |||||
```

FIGURE 5D

```
GU978996    GGCTTTTCATTTAGCTTTAAACAAAAAAAGTCAGCTACTCAGTCTGTCGGA---TCTAAA
                 810       820       830       840       850       860

1550      1560      1570      1580      1590      1600
rmf.C2.F8E.5 CGAGACCCAAATACACCTGACTTTTTTGTAAAAATGACCGATTCTCAACGTCATTTATTC
             ||||  ||||||||||  |||  ||||  || ||||||  |||   |||||||||| |||||
GU978996    AGAGATCCAAATACATTGGACCCTTTTTCAACAATGACAGATAAACAACGTCATCTATTC
                 870       880       890       900       910       920

1610      1620      1630      1640      1650      1660
rmf.C2.F8E.5 GCAACTAAACTTTCTGAAATGCCAGAGATGTCTAAATATTCTCAAGGTACAGAGTCGTAT
             || | |||||| || ||  | ||  ||||||  ||||||||| ||||||||  ||   |||
GU978996    GCTAGTAAACTCTCCGAGCTTCCTGAGATGAGTAAATATTCACAAGGTACGGAAAGCTAT
                 930       940       950       960       970       980

1670      1680      1690      1700      1710      1720
rmf.C2.F8E.5 CAACAGTTTGCTATCCGTATTGCCGATATGCTTTTAGAACCTGAAAAGTTAAAGAATTCG
             || ||||||||||  ||||||  || |  ||||| |||   ||| | ||
GU978996    CAGCAGTTTGCTGTACGTATCGCTGGCATGCTGCAAGATACAGAGCGATTTAGGGAAATT
                 990       1000      1010      1020      1030      1040

EMSTD_PRO:GU978999
ID   GU978999; SV 1; linear; genomic DNA; STD; PRO; 1125 BP.
AC   GU978999;
DE   Acinetobacter baumannii plasmid p537 plasmid replication protein Aci 5
DE   (repA) gene, complete cds. . . .
SCORES  z-score: 982.7 E(): 1.9e-48
>>EMSTD_PRO:GU978999                                        (1125 nt)
   63.4% identity in 1069 nt overlap
   (673-1723:30-1085)

EMSTD_PRO:CP000522
ID   CP000522; SV 1; circular; genomic DNA; STD; PRO; 13408 BP.
AC   CP000522;
DE   Acinetobacter baumannii ATCC 17978 plasmid pAB1, complete sequence. . . .
SCORES  z-score: 908.7 E(): 2.1e-45
>>EMSTD_PRO:CP000522                                        (13408 nt)
   64.6% identity in 905 nt overlap
   (829-1723:4-893)
```

*BLASTN2:*

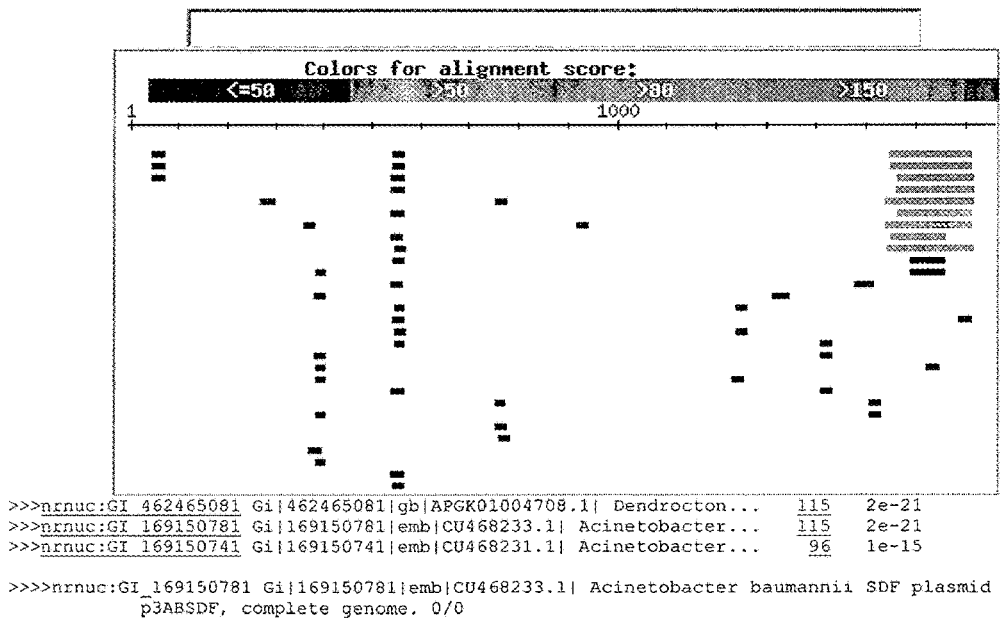

```
>>>nrnuc:GI_462465081 Gi|462465081|gb|APGK01004708.1| Dendrocton...   115  2e-21
>>>nrnuc:GI_169150781 Gi|169150781|emb|CU468233.1| Acinetobacter...   115  2e-21
>>>nrnuc:GI_169150741 Gi|169150741|emb|CU468231.1| Acinetobacter...    96  1e-15

>>>>nrnuc:GI_169150781 Gi|169150781|emb|CU468233.1| Acinetobacter baumannii SDF plasmid
         p3ABSDF, complete genome. 0/0
```

FIGURE 5E

```
         Length = 24922
 Score =  115 bits (58), Expect = 2e-21
 Identities = 133/158 (84%)
 Strand = Plus / Plus
Query: 1555 aatacacctgacttttttgtaaaaatgaccgattctcaacgtcatttattcgcaactaaa 1614
            ||||||||||||||||||| ||||||||| ||| | |||||||||||||| || | ||||
Sbjct: 1283 aatacacctgacttttttgtcaaaatgactgatgcccaacgtcatttatttgccaataaa 1342

Query: 1615 ctttctgaaatgccagagatgtctaaatattctcaaggtacagagtcgtatcaacagttt 1674
            | ||||||||||| || ||| ||||||||| ||||| |||||   || ||||| ||| |||
Sbjct: 1343 atgtctgaaatgcctgatatgagtaaatattcgcaaggaacagaaagctaccaacaattt 1402

Query: 1675 gctatccgtattgccgatatgcttttagaacctgaaaa 1712
            ||||| ||||| || |||||||||||||| |||||||
Sbjct: 1403 gctattcgtatcgctgatatgcttttagagcctgaaaa 1440

Score = 97.6 bits (49), Expect = 4e-16
 Identities = 133/161 (82%)
 Strand = Plus / Plus
Query: 1549 gacccaaatacacctgacttttttgtaaaaatgaccgattctcaacgtcatttattcgca 1608
            |||||||| ||||| ||||| ||| |||||||||| |||| ||| |||||| ||| |||||
Sbjct: 7634 gacccaaacacacccgacttctcttataaaaatgactgatgcacaacgccatctattcgcc 7693

Query: 1609 actaaactttctgaaatgccagagatgtctaaatattctcaaggtacagagtcgtatcaa 1668
            | |||| | ||||||||||||| || ||| ||||||||||||||| ||||    ||||||
Sbjct: 7694 aataaaatgtctgaaatgcctgaaatgattaaatattctcaaggcacagaaagctatcaa 7753

Query: 1669 cagtttgctatccgtattgccgatatgcttttagaaccctga 1709
            ||||||| || || ||||| |||||||||||| ||||||||
Sbjct: 7754 cagtttacaattcgcattgctgatatgcttttacaacctga 7794

>>>>nrnuc:GI_169150741 Gi|169150741|emb|CU468231.1| Acinetobacter baumannii SDF plasmid
            p1ABSDF, complete genome. 0/0
         Length = 6106
 Score = 95.6 bits (48), Expect = 1e-15
 Identities = 126/152 (82%)
 Strand = Plus / Plus
Query: 1564 gacttttttgtaaaaatgaccgattctcaacgtcatttattcgcaactaaactttctgaa 1623
            ||||| ||||| ||||||||||||||||| | ||||| ||| |||||||| | |||| | |||||
Sbjct: 1216 gacttctttgtcaaaatgaccgatgcacaacgccatctattcgccaataaaatgtctgag 1275

Query: 1624 atgccagagatgtctaaatattctcaaggtacagagtcgtatcaacagtttgctatccgt 1683
            |||| || ||| ||||||||| ||||| |||||     |||||||||||||||||||||
Sbjct: 1276 atgcctgaaatgagcaaatattcacaaggcacagaaagctatcaacagtttgctatccgt 1335

Query: 1684 attgccgatatgcttttagaacctgaaaagtt 1715
            || || || ||||||||||| |||||||||||
Sbjct: 1336 atcgctgacatgcttttagagcctgaaaagtt 1367

>>>>nrnuc:GI_169150750 Gi|169150750|emb|CU468232.1| Acinetobacter baumannii SDF plasmid
            p2ABSDF, complete genome. 0/0
         Length = 25014
 Score = 89.7 bits (45), Expect = 9e-14
 Identities = 126/153 (82%)
 Strand = Plus / Plus Query: 1563 tgacttttttgtaaaaatgaccgattctcaacgtcatttattcgcaactaaactttctga 1622
            |||||| ||||| ||||||||||||||||| | |||| ||| ||||||| | |||| | |||||
Sbjct: 11463 tgacttctttgtcaaaatgaccgatgcacaacgccatctattcgccaataaaatgtctga 11522

Query: 1623 aatgccagagatgtctaaatattctcaaggtacagagtcgtatcaacagtttgctatccg 1682
            ||||| || |||  ||||||||| ||||| |||||     |||||||||||| |||||||
Sbjct: 11523 gatgcctgaaatgagcaaatattcacaaggcacagaaagctatcaacagttttctatccg 11582

Query: 1683 tattgccgatatgcttttagaacctgaaaagtt 1715
            ||| || || ||||||||||| |||||||||||
Sbjct: 11583 tatcgctgacatgcttttagagcctgaaaagtt 11615
```

HCBI SEQUENCES AS AN EARLY MARKER FOR THE FUTURE DEVELOPMENT OF CANCER AND DISEASES OF THE CNS AND AS A TARGET FOR CANCER TREATMENT AND PREVENTION

RELATED APPLICATIONS AND INCORPORATION BY REFERENCE

This application is a continuation-in-part application of international patent application Serial No. PCT/EP2014/002912 filed Oct. 30, 2014, which published as PCT Publication No. WO 2015/062726 on May 7, 2015, which claims benefit of European patent application Serial No. EP 13005138.6 filed Oct. 30, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on May 9, 2018, is named $43164_{13}00_{13}2010_{13}$ SL.txt and is 91,909 bytes in size.

FIELD OF THE INVENTION

The present invention relates to HCBI (Healthy Cattle Blood Isolate) nucleotide sequences as well as probes and primers which may comprise part of said nucleotide sequences and antibodies against polypeptides encoded by said nucleotide sequences. Finally, the present invention relates to the use of said compounds as an early marker for the future development of diseases such as cancer and diseases of the CNS.

BACKGROUND OF THE INVENTION

Several epidemiological analyses conducted in recent decades indicate that the long-term consumption of "red" meat processed by different ways (including smoked meat and meat as component of sausages) can be regarded as a risk factor for colon cancer (World Cancer Report 2007, zur Hausen 2012). "Red" meat is regarded as comprising beef, pork, mutton and goat meat, in contrast to "white" meat (poultry meat/fish).

Thus far, chemical carcinogenic substances being produced during roasting, grilling, barbecuing, smoking and air-drying were blamed as risk factors for cancer. However, often the fact was disregarded that the same substances are also produced in comparable concentrations during analogous ways of preparation of poultry meat/fish. Accordingly, this does not support the assumption that these chemical substances play an exclusive role as regards the development of colon cancer. Since, in addition, the current epidemiological analyses suggest that beef is the main risk factor it has been postulated that an additional species-specific—presumably infectious—factor contributes to the triggering of this type of cancer (zur Hausen, 2012). The results of the correlation of analyses of the global spreading of domesticated bovine species with the global incidence of colon cancer seem to suggest that the consumption of meat of bovine species stemming from European/Asian cattle (*Bos taurus*) but not from breedings of zebu, water buffalo or yak might be of importance as a main risk factor.

Citation or identification of any document in this application is not an admission that such document is available as prior art to the present invention.

SUMMARY OF THE INVENTION

Thus, the technical problem underlying the present invention is to identify specific nucleotide sequences that might be associated with diseases like cancer or diseases of the CNS and, thus, to provide means for diagnosis and therapy.

The solution to said technical problem is achieved by providing the embodiments characterized in the claims. During the experiments resulting in the present invention sera of cattle were screened for infectious agents—starting from the assumption that the presence in sera is also indicative for the presence of these agents in "red" meat. Sera from healthy cows were screened and two components of a new viral nucleic acid could be isolated. The DNA sequences and open reading frames of these components showed a clearly recognizable relationship to sequences which were already described for transmissible spongiform enzephalopathies (TSE) for TSE-diseases of sheep, cattle and humans.

Thus, it is reasonable to assume that these viral sequences might be associated with the development of diseases like cancer and diseases of the CNS.

Accordingly, the present invention relates to an HCBI polynucleic acid which may comprise:
(a) a nucleotide sequence depicted in any one of FIGS. 1 to 5;
(b) a nucleotide sequence having at least 90% identity to a nucleotide sequence of (a);
(c) a fragment of a nucleotide sequence of (a) or (b);
(d) a nucleotide sequence being complementary to a nucleotide sequence of (a), (b) or (c); or
(e) a nucleotide sequence which is redundant as a result of the degeneracy of the genetic code compared to any of the above-given nucleotide sequences.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A-I: Nucleotide sequence of HCBI1.225 and putative open reading frames. Also shown are alignments to nucleotide sequences found in data bases and alignments of peptides derived from open reading frames of HCBI1.225 to corresponding "Sphinx" amino acid sequences. Figure 1A-I discloses SEQ ID NOS 1-7, 84, 8, 85, 9, 86, 10-32, respectively, in order of appearance.

FIG. 2A-G: Nucleotide sequence of HCBI2.170 and putative open reading frames. Also shown are alignments to nucleotide sequences found in data bases and alignments of peptides derived from open reading frames of HCBI2.170 to corresponding "Sphinx" amino acid sequences. FIG. 2A-G discloses SEQ ID NOS 33-51, 87, 52, 88, 53, 89, and 54, respectively, in order of appearance.

FIG. 3A-C: Nucleotide sequence of HCBI3.108 and putative open reading frames. Also shown are alignments to nucleotide sequences found in data bases and alignments of peptides derived from open reading frames of HCBI3.108 to corresponding "Sphinx" amino acid sequences. FIG. 3A-C discloses SEQ ID NOS 55-67, respectively, in order of appearance.

FIG. 4A-E: Nucleotide sequence of HCBI4.296 and putative open reading frames. Also shown are alignments to nucleotide sequences found in data bases and alignments of peptides derived from open reading frames of HCBI4.296 to corresponding "Sphinx" amino acid sequences. FIG. 4A-E discloses SEQ ID NOS 68-70, 90, and 71, respectively, in order of appearance.

FIG. 5A-E: Nucleotide sequence of HCBI5.173 and putative open reading frames. Also shown are alignments to nucleotide sequences found in data bases and alignments of peptides derived from open reading frames of HCBI5.173 to corresponding "Sphinx" amino acid sequences. FIG. 5A-E discloses SEQ ID NOS 72-74, 91, and 75-83, respectively, in order of appearance.

DETAILED DESCRIPTION OF THE INVENTION

The term "polynucleic acid" refers to a single-stranded or double-stranded nucleic acid sequence. A polynucleic acid may consist of deoxyribonucleotides or ribonucleotides, nucleotide analogues or modified nucleotides or may have been adapted for diagnostic or therapeutic purposes. A polynucleic acid may also comprise a double stranded cDNA clone which can be used, for example, for cloning purposes.

The HCBI polynucleic acids of the invention can be prepared according to well-known routine methods, for example, by (a) isolating the entire DNA or RNA from a sample, (b) detecting the HCBI sequence by hybridization or PCR and (c) cloning of the HCBI sequence into a vector.

Also included within the present invention are sequence variants of the polynucleic acid of the invention containing either deletions and/or insertions of one or more nucleotides, especially insertions or deletions of one or more codons, mainly at the extremities of oligonucleotides (either 3' or 5') and which show at least 90%, 95% or 98% identity to said polynucleic acid sequences of the invention. Polynucleic acid sequences according to the present invention which are similar to the sequences as shown in FIGS. 1 to 5 can be characterized and isolated according to any of the techniques known in the art, such as amplification by means of sequence-specific primers, hybridization with sequence-specific probes under more or less stringent conditions, sequence determination of the genetic information of HCBI etc.

The present invention also provides fragments of the nucleotide sequences of the present invention described above that are, preferably, capable of replicating autonomously [???]. The skilled person can derive at such fragments without undue experimentation. The lengths of the fragments are not critical, however, fragments having a length of at least 45, at least 55, or at least 65 nt are preferred.

The person skilled in the art can easily determine which nucleic acid sequences are related to a nucleotide sequence of FIGS. 1 to 5 or which fragments are still capable of replicating autonomously by using standard assays.

The present invention also provides polynucleic acid sequences which are redundant as a result of the degeneracy of the genetic code compared to any of the above-given nucleotide sequences. These variant polynucleic acid sequences will thus encode the same amino acid sequence as the polynucleic acids they are derived from.

The HCBI polynucleic acids of the invention might be present as an extrachromosomal episome, might be integrated into the host's genome and/or might be linked to a host cell DNA.

The present invention also relates to an oligonucleotide primer which may comprise or consisting of part of a polynucleic acid as defined above, with said primer being able to act as primer for specifically sequencing or specifically amplifying TT virus HCR polynucleic acid of the invention and attached cellular DNA sequences.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow priming the synthesis of the extension products. Preferably the primer is about 5-50 nucleotides. Specific length and sequence will depend on the complexity of the required DNA or RNA targets, as well as on the conditions of primer use such as temperature and ionic strength.

The fact that amplification primers do not have to match exactly with corresponding template sequence to warrant proper amplification is amply documented in the literature. The amplification method used can be either polymerase chain reaction (PCR), ligase chain reaction (LCR), nucleic acid sequence-based amplification (NASBA), transcription-based amplification system (TAS), strand displacement amplification (SDA) or amplification by means of Qβ replicase or any other suitable method to amplify nucleic acid molecules using primer extension. During amplification, the amplified products can be conveniently labelled either using labelled primers or by incorporating labelled nucleotides.

Labels may be isotopic (32P, 35S, etc.) or non-isotopic (biotin, digoxigenin, etc.). The amplification reaction is repeated between 20 and 70 times, advantageously between 25 and 45 times.

Any of a variety of sequencing reactions known in the art can be used to directly sequence the viral genetic information and determine the orf by translating the sequence of the sample into the corresponding amino acid sequence. Exemplary sequencing reactions include those based on techniques developed by Sanger or Maxam and Gilbert. It is also contemplated that a variety of automated sequencing procedures may be utilized when performing the subject assays including sequencing by mass spectrometry (see, for example: PCT publication WO 94/16101). It will be evident to one skilled in the art that, for example the occurrence of only two or three nucleic bases needs to be determined in the sequencing reaction.

Preferably, these primers are about 5 to 50 nucleotides long, more preferably from about 10 to 25 nucleotides. Most preferred are primers having a length of at least 13 bases.

The present invention also relates to an oligonucleotide probe which may comprise or consisting of part of a HCBI polynucleic acid as defined above, with said probe being able to act as a hybridization probe for specific detection of a HCBI polynucleic acid according to the invention.

The probe can be labelled or attached to a solid support.

The term "probe" refers to single stranded sequence-specific oligonucleotides which have a sequence which is complementary to the target sequence of a HCBI polynucleic acid to be detected.

Preferably, these probes are about 5 to 50 nucleotides long, more preferably from about 10 to 25 nucleotides. Most preferred are probes having a length of at least 13 bases.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The oligonucleotides according to the present invention, used as primers or probes may also contain or consist of nucleotide analoges such as phosphorothioates, alkylphosphoriates or peptide nucleic acids or may contain intercalating agents. These modifications will necessitate adaptions with respect to the conditions under which the oligonucleotide should be used to obtain the required specificity and sensitivity. However, the eventual results will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The polynucleic acids of the invention may be comprised in a composition of any kind. Said composition may be for diagnostic, therapeutic or prophylactic use.

The present invention also relates to a recombinant expression vector which may comprise an HCBI polynucleic acid of the invention as defined above operably linked to prokaryotic, eukaryotic or viral transcription and translation control elements as well as host cells containing such vector.

The term "vector" may comprise a plasmid, a cosmid, an artificial chromosome, a phage, or a virus or a transgenic non-human animal. Particularly useful for vaccine development may be HCBI recombinant molecules, BCG or adenoviral vectors, as well as avipox recombinant viruses.

The term "recombinant expression" used within the context of the present invention refers to the fact that the polypeptides of the present invention are produced by recombinant expression methods be it in prokaryotes, or lower or higher eukaryotes as discussed in detail below.

The term "host cell" refers to cells which can be or have been, used as recipients for a recombinant vector or other transfer polynucleotide, and include the progeny of the original cell which has been transfected.

It is understood that the progeny of a single parental cell may not necessarily be completely identical in morphology or in genomic or total DNA complement as the original parent, due to natural, accidental, or deliberate mutation or recombination.

The term "lower eukaryote" refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluiveromyces, Pichia* (e.g. *Pichia pastoris*), *Hansenula* (e.g. *Hansenula polymorph*), *Schwaniomyces, Schizosaccharomyces, Yarowia, Zygosaccharomyces* and the like. *Saccharomyces cerevisiae, S. carlsbergensis* and *K. lactis* are the most commonly used yeast hosts, and are convenient fungal hosts.

The term "higher eukaryote" refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic non-human animals.

The term "prokaryotes" refers to hosts such as *E. coli, Lactobacillus, Lactococcus, Salmonella, Streptococcus, Bacillus subtilis* or *Streptomyces*. Also these hosts are contemplated within the present invention.

The segment of the HCBI DNA encoding the desired sequence inserted into the vector sequence may be attached to a signal sequence. Said signal sequence may be that from a non-HCBI source, but particularly preferred constructs according to the present invention contain signal sequences appearing in the HCBI genome before the respective start points of the proteins.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. For vaccination of humans the avipox and Ankara Modified Virus (AMV) are particularly useful vectors.

Also known are insect expression transfer vectors derived from baculovirus Autographa californica nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

The present invention also relates to a polypeptide having an amino acid sequence encoded by an HBCI polynucleic acid as defined above, or a part or an analogue thereof being substantially similar and biologically equivalent.

The term "polypeptide" refers to a polymer of amino acids and does not refer to a specific length of the product. Thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, peptide nucleic acid (PNA), etc.), polypeptides with substituted linkages, as well as other modifications known in the art, both naturally occurring and non-naturally occurring.

The polypeptides according to the present invention contain preferably at least 3, preferably 4 or 5 contiguous HCBI amino acids, 6 or 7 preferably however at least 8 contiguous HCBI amino acids, at least 10 or at least 15.

The polypeptides of the invention, and particularly the fragments, can be prepared by classical chemical synthesis. The synthesis can be carried out in homogeneous solution or in solid phase. The polypeptides according to this invention can also be prepared by means of recombinant DNA techniques. The present invention also relates to a method for production of a recombinant polypeptide as defined above, which may comprise: (a) transformation of an appropriate cellular host with a recombinant vector, in which a polynucleic acid or a part thereof as defined above has been inserted under the control of the appropriate regulatory elements, (b) culturing said transformed cellular host under conditions enabling the expression of said insert, and (c) harvesting said polypeptide.

The present invention also relates to an antibody raised upon immunization with at least one polypeptide as defined above, with said antibody being specifically reactive with any of said polypeptides, and with said antibody being preferably a monoclonal antibody. The term "antibody", preferably, relates to antibodies which consist essentially of pooled monoclonal antibodies with different epitopic specifities, as well as distinct monoclonal antibody preparations. Monoclonal antibodies are made from an antigen containing, e.g., a polypeptide encoded by an HCBI polynucleic acid of the invention or a fragment thereof by methods well known to those skilled in the art. As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. Thus, these fragments are preferred, as well as the products of a FAB or other immunoglobulin expression library. Moreover, antibodies useful for the purposes of the present invention include chimerical, single chain, and humanized antibodies.

Preferably, the antibody or antigen binding fragment thereof carries a detectable label. The antibody/fragment can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

The present invention also relates to a diagnostic kit for use in determining the presence of a HCBI polynucleic acid or polypeptide of the invention, said kit which may comprise a primer, a probe, and/or an antibody of the invention.

The present invention also relates to a method for the detection of an HCBI polynucleic acid according to the invention present in a biological sample, which may comprise: (a) optionally extracting sample polynucleic acid, (b) amplifying the polynucleic acid as described above with at least one primer as defined above, optionally a labelled primer, and (c) detecting the amplified polynucleic acids.

The term "polynucleic acid" can also be referred to as analyte strand and corresponds to a single- or double-stranded polynucleic acid molecule.

The term "labelled" refers to the use of labelled nucleic acids. This may include the use of labelled nucleotides incorporated during the polymerase step of the amplification or labelled primers, or by any other method known to the person skilled in the art.

The present invention also relates to a method for the detection of an HBCI polynucleic acid according to the invention present in a biological sample, which may comprise: (a) optionally extracting sample polynucleic acid, (b) hybridizing the polynucleic acid as described above with at least one probe as defined above, and (c) detecting the hybridized polynucleic acids.

The hybridization and washing conditions are to be understood as stringent and are generally known in the art. However, according to the hybridization solution (SSC, SSPE, etc.), these probes should be hybridized at their appropriate temperature in order to attain sufficient specificity.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions.

Suitable assay methods for purposes of the present invention to detect hybrids formed between the oligonucleotide probes and the HCBI polynucleic acid sequences in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the polynucleic acids of the sample and the oligonucleotide probes according to the present invention may be used.

The present invention also relates to a method for detecting a polypeptide encoded by an HCBI polynucleic acid of the present invention or an antibody against said polypeptide present in a biological sample, which may comprise: (a) contacting the biological sample for the presence of such polypeptide or antibody as defined above, and (b) detecting the immunological complex formed between said antibody and said polypeptide.

The immunoassay methods according to the present invention may utilize antigens from different domains of the new and unique polypeptide sequences of the present invention. It is within the scope of the invention to use for instance single or specific oligomeric antigens, dimeric antigens, as well as combinations of single or specific oligomeric antigens. The HCBI antigens of the present invention may be employed in virtually any assay format that employs a known antigen to detect antibodies. Of course, a format that denatures the HCBI conformational epitope should be avoided or adapted. A common feature of all of these assays is that the antigen is contacted with the body component suspected of containing HCBI antibodies under conditions that permit the antigen to bind to any such antibody present in the component. Such conditions will typically be physiologic temperature, pH and ionic strength using an excess of antigen. The incubation of the antigen with the specimen is followed by detection of immune complexes which may be comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon), diazotized paper, nylon membranes, activated beads, and Protein A beads. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of HCBI antibodies in the antibody-antigen complexes is directly monitored. This may be accomplished by determining whether (labelled) anti-xenogeneic (e.g. anti-human) antibodies which recognize an epitope on anti-HCBI antibodies will bind due to complex formation. In a competitive format, the amount of HCBI antibodies in the sample is deduced by monitoring the competitive effect on the binding of a known amount of labeled antibody (or other competing ligand) in the complex.

Complexes formed which may comprise anti-HCBI antibody (or in the case of competitive assays, the amount of competing antibody) are detected by any of a number of known techniques, depending on the format. For example, unlabeled HCBI antibodies in the complex may be detected using a conjugate of anti-xenogeneic Ig complexed with a label (e.g. an enzyme label).

In an immunoprecipitation or agglutination assay format the reaction between the HCBI antigens and the antibody forms a network that precipitates from the solution or suspension and forms a visible layer or film of precipitate. If no anti-HCBI antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen/antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin.

The above methods are useful for evaluating the risk of developing diseases like cancer or an autoimmune disease due to the deleterious effects of the presence of a subgenomic HCBI polynucleotide sequence by itself or linked to a particular host gene or gene fragment within the patient's cells and allow taking appropriate counter measures.

Thus, the present invention also relates to an antisense oligonucleotide or iRNA specific for the HCBI virus polynucleic acid of the invention.

The generation of suitable antisense oligonucleotides or iRNAs includes determination of a site or sites within the HCBI polynucleic acid for the antisense interaction to occur such that the desired effect, e.g., inhibition of expression of the polypeptide, will result. A preferred intragenic site is (a) the region encompassing the translation initiation or termination codon of the open reading frame (ORF) of the gene or (b) a region of the mRNA which is a "loop" or "bulge", i.e., not part of a secondary structure. Once one or more target sites have been identified, oligonucleotides are chosen which are sufficiently complementary to the target, i.e., hybridize sufficiently well and with sufficient specificity, to give the desired effect. In the context of this invention, "hybridization" means hydrogen bonding, which may be Watson-Crick, Hoogsteen or reversed Hoogsteen hydrogen bonding, between complementary nucleoside or nucleotide bases. "Complementary" as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

"Oligonucleotide" (in particular in the context of antisense compounds) refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention may comprise from about 8 to about 50 nucleobases (i.e. from about 8 to about 50 linked nucleosides). Particularly preferred antisense compounds are antisense oligonucleotides, even more preferably those which may comprise from about 15 to about 25 nucleobases. Antisense compounds include ribozymes, external guide sequences (EGS), oligonucleotides (oligozymes), and other short catalytic RNAs or catalytic oligonucleotides which hybridize to the target nucleic acid and inhibit its expression. The antisense compounds also include an iRNA which may comprise a sense sequence and an antisense sequence, wherein the sense and antisense sequences form an RNA duplex and wherein the antisense sequence may comprise a nucleotide sequence sufficiently complementary to the nucleotide sequence of an HCBI polynucleic acid of the present invention.

Alternatively, the invention provides a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, herpes virus, vaccinia, or, more preferably, an RNA virus such as a retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957. The HCBI polynucleotide sequences of the invention may also serve as a suitable vector itself, either composed solely of rearranged HCBI sequences or of chimeric HCBI host cell DNA sequences. In addition, the nucleotide sequences of the invention may be used for the construction of artificial chromosomes.

In order to achieve expression only in the target organ, the DNA sequences for transcription of the antisense oligonucleotides can be linked to a tissue specific promoter and used for gene therapy. Such promoters are well known to those skilled in the art.

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which can result in increased stability are known to the person skilled in the art, preferably such modification is a phosphorothioate linkage.

A preferred oligonucleotide mimetic is an oligonucleotide mimetic that has been shown to have excellent hybridization properties, and is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Modified oligonucleotides may also contain one or more substituted or modified sugar moieties. Preferred oligonucleotides may comprise one of the following at the 2' position: OH; F; 0-, S—, or N-alkyl; 0-, S—, or N-alkenyl; 0-, S— or N-alkynyl; or 0-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. A particularly preferred modified sugar moiety is a 2'-O-methoxyethyl sugar moiety.

Antisense-oligonucleotides of the invention may also include nucleobase modifications or substitutions. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine etc., with 5-methylcytosine substitutions being preferred since these modifications have been shown to increase nucleic acid duplex stability.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, a thiocholesterol, an aliphatic chain, e.g., dodecandiol or undecyl residues, a phospholipid, a polyamine or a polyethylene glycol chain, or adamantane acetic acid, a palmityl moiety, or an octadecylamine or hexylamino-carbonyl-oxycholesterol moiety.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

The present invention also relates to a pharmaceutical composition which may comprise an antibody or antisense oligonucleotide of the invention and a suitable excipient, diluent or carrier. Preferably, in a pharmaceutical composition, such compound as described above is combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose.

An "effective dose" refers to an amount of the active ingredient that is sufficient to prevent the disease or to affect the course and the severity of the disease, leading to the reduction or remission of such pathology. An "effective dose" useful for treating and/or preventing these diseases or disorders may be determined using methods known to one skilled in the art.

Administration of the suitable compositions may be effected by different ways, e.g. by intravenous, intraperitoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

In a preferred embodiment of the present invention, the disease that can be prevented/treated is cancer, preferably colorectal cancer or a disease of the CNS, preferably Alzheimer's disease or multiple sclerosis (MS). The terms "cancer" and "disease of the CNS" also may comprise early stages of said diseases.

The present invention also relates to a vaccine for immunizing a mammal against an HCBI infection, which may comprise at least one polypeptide or HCBI polynucleic acid as defined above, in a pharmaceutically acceptable carrier.

A "vaccine" is an immunogenic composition capable of eliciting protection against HCBI, whether partial or complete. A vaccine may also be useful for treatment of an individual, in which case it is called a therapeutic vaccine.

The term "therapeutic" refers to a composition capable of treating HCBI infection. The term "effective amount" refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. Effective amounts will be found within a relatively large, non-critical range. An appropriate effective amount can be readily determined using only routine experimentation. Preferred ranges of proteins for prophylaxis of HCBI caused diseases are 0.01 to 100 µg/dose, preferably 0.1 to 50 µg/dose. Several doses may be needed per individual in order to achieve a sufficient immune response and subsequent protection against an HCBBI infection and an HCBI caused disease, respectively.

Pharmaceutically acceptable carriers include any carrier that does not itself induce the production of antibodies harmful to the individual receiving the vaccine. Suitable carriers are typically large, slowly metabolized macromolecules such as proteins, polysaccharides, polylactic acids, polyglycolic acids, polymeric amino acids, and amino acid copolymers. Such carriers are well known to those of ordinary skill in the art.

Preferred adjuvants to enhance effectiveness of the composition include, but are not limited to: aluminim hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl sn-glycero-3-hydroxy-phosphoryloxy)-ethylamine (MTP-PE) and RIBI, which contains three components extracted from bacteria, monophosphoryl lipid A, trehalose dimycolate, and cell wall Skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, MA) or SAF-1 (Syntex) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions. Solid forms suitable for solution in, or suspension in, liquid vehicles prior to injection may also be prepared. The preparation also may be emulsified or encapsulated in liposomes for enhanced adjuvant effect. The proteins may also be incorporated into Immune Stimulating Complexes together with saponins, for example Quil A (ISCOMS).

Immunogenic compositions used as vaccines may comprise a "sufficient amount" or "an immunologically effective amount" of the proteins of the present invention, as well as any other of the above mentioned components, as needed. "Immunologically effective amount" means that the administration of that amount to an individual, either in a single dose or as part of a series, is effective for treatment, as defined above. This amount varies depending upon the health and physical condition of the individual to be treated, the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. Usually, the amount will vary from 0.01 to 1000 µg/dose, more particularly from 0.1-100 µg/dose.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

The following examples are intended to illustrate, but not to limit the invention. While such examples are typical of those that might be used, other methods known to those skilled in the art may alternatively be utilized.

EXAMPLE 1

Material and Methods
(A) Fractionation of Bovine Sera on Density-Sedimentation Gradients with Subsequent Cloning Bovine sera were separated on Optiprep (iodixanol) step gradients as previously described (Buck et al., 2004). Fractions were collected and DNA extracted. Rolling circle amplification was performed (de Villiers et al., 2011) on each fraction before digestion with the restriction enzymes BamH1 and EcoR1. Resulting fragments were cloned into pUC18 or pUC19 prior to sequencing.
(B) In Vitro Replication (de Villiers et al., 2011) of HCBI1.225

Linear full-length HCBI1.225 was transfected into 293TT cells (Lipofectamine). Cultures were passaged every 2-3 days. DNA and RNA were extracted from a fraction of the cells upon passaging. Input DNA was removed by Dpn1 digestion. DNA and RNA of HCBI1.225 were demonstrated up to day 17 in cell culture.

EXAMPLE 2

Characterization of the HCBI Sequences 120 sera from healthy cows obtained from the "Veterinärinstitut der Universität Leipzig" (Professor Müller) were screened and after purification of viral particles, DNA extraction and "rolling circle" amplification (de Villiers et al., 2011) two components of a new viral nucleic acid could be isolated. The DNA sequences and open reading frames of these components showed a clearly recognizable relationship to sequences which were already described for transmissible spongiform enzephalopathies (TSE) for TSE-diseases of sheep, cattle and humans (Manuelidis, 2011). These agents were not further characterized and designated as "Sphinx virus". Since the DNA sequences (and open reading frames) obtained in the present invention from healthy cows show homologies to the corresponding sequences described by Manuelidis but are not identical the designation HCBI (Healthy Cattle Blood Isolate) is proposed.

In this context, diseases of the CNS (e.g., Multiple Sclerosis, Alzheimer's disease) are also highly interesting since the similar sequences described by Manuelidis are primarily found in the CNS.

The "Shinx" sequences (Manuelidis, 2011) show high homologies to plasmid sequences of the bacterium *Acinetobacter* (Vallenet et al., 2008; Longkummer et al., 2013). The sequences obtained in the present invention also exhibit striking homologies to the corresponding plasmid sequences. Thus, at first glance it is tempting to speculate that the results are due to contamination of the samples with *Acinetobacter* viruses. Although meanwhile a plethora of *Acinetobacter* plasmids has been sequenced none of these sequences corresponds to the DNA sequences of the present invention that were obtained from three different batches of sera. Since initially the isolation of these DNAs was achieved by purification of the viruses via density gradient centrifugation the apparently common presence of these viruses in blood of cow sera is not necessarily attributable to viral contamination derived from bacteria. Moreover, the presence of DNA sequences of these viruses in human cancer cells is incommensurate with such interpretation.

Interestingly, a group of scientists in the UK published serological data again and again for years pointing to an increased selective formation of antibodies against *Acinetobacter* proteins but not against other bacterial antigenes obtained from patients suffering from multiple sclerosis (see review article: Ebringer et al., 2012). These results could not be confirmed by the group of Chapman (Chapman et al., 2005). However, it has to be stressed that the group of Chapman used a different type of *Acinetobacter* (*Acinetobacter calcoaceticus*). Unequivocal results were obtained by the group of Ebringer for three strains of *Acinetobacter* (*Acinetobacter lwoffii, A. radioesistens* and a specific isolate, A. 11171). However, the results obtained for *A. junii* 17908 were less impressive and significant reactivity was hardly detectable (Hughes et al., 2001). These results suggest that we are dealing with strain-specific reactivities wherein this sero-reactivity is due to strain-specific plasmids exhibiting homologies to the DNA sequences obtained in the present invention.

REFERENCES

Buck C B, Pastrana D V, Lowy D R, Schiller J T. Efficient intracellular assembly of papillomaviral vectors. J. Virol. 2004; 78:751-757.

Chapman M D, Hughes L E, Wilson C D, Namnyak S, Thompson E J, Giovannoni G. No evidence for production of intrathecal immunoglobulin G against *Acinetobacter* or *Pseudomonas* in multiple sclerosis. Eur Neurol. 2005; 53(1):27-31.

de Villiers E M, Borkosky S S, Kimmel R, Gunst K, and Fei J W. (2011) The diversity of Torque teno viruses: In vitro replication leads to the formation of additional replication-competent subviral Molecules. J Virol 2011; 85(14):7284-7295

Ebringer A, Hughes L, Rashid T, Wilson C. *Acinetobacter* Immune Responses in Multiple Sclerosis: Etiopathogenetic Role and Its Possible Use as a Diagnostic Marker. Arch Neurol. 2005; 62:33-36.

Ebringer A, Rashid T, Wilson C. The role of *Acinetobacter* in the pathogenesis of multiple sclerosis examined by using Popper sequences. Med Hypotheses. 2012; 78(6):763-769.

Hughes, L. E., Bonell, S., Natt, R. S., Wilson, C., Tiwana, H., Ebringer, A., Cunningham, P., Chamoun, V., Thompson, E. J., Croker, J., and Vowles, J. Antibody responses to *Acinetobacter* spp. and *Pseudomonas aeroginosa* in multiple sclerosis: prospects for diagnosis using the myelin-*Acinetobacter*-neurofilament antibody index. Clin. Diagn. Laboratory Immunol. 2001; 8: 1181-1188.

Longkumer T, Kamireddy S, Muthyala V R, Akbarpasha S, Pitchika G K, Kodetham G, Ayaluru M, Siddavattam D. Scientific Reports 2013; 3:2240.

Manuelidis L. Nuclease resistant circular DNAs copurify with infectivity in scrapie and CJD. J. Neurovirol. 2011; 17:131-145.

Vallenet D, Nordmann P, Barbe V, Poirel L, Mangenot S, Bataille E, Dossat C, Gas S, Kreimeyer A, Lenoble P, Oztas S, Poulain J, Segurens B, Robert C, Abergel C, Claverie J-M, Raoult D, Medigue C, Weissenbach J, Cruveiller S. Comparative analysis of Acinetobacters: three genomes for three lifestyles. PLoS One 2008; 3(3):e1805-e1805.

Xu B, Zhi N, Hu G, Wan Z, Zheng X, Liu X, Wong S, Kajigaya S, Zhao K, Mao Q, Young N S. Hybrid DNA virus in Chinese patients with seronegative hepatitis discovered by deep sequencing. Proc Natl Acad Sci USA. 2013; 110: 10264-9.

zur Hausen H. Red meat consumption and cancer: Reasons to suspect involvement of bovine infectious factors in colorectal cancer. Int J Cancer 2012; 130:2475-2483.

zur Hausen H. World Cancer Report, IARC, Lyon, 2013.

The invention is further described by the following numbered paragraphs:

1. An HCBI polynucleic acid comprising:
   (a) a nucleotide sequence depicted in any one of FIGS. 1 to 5;
   (b) a nucleotide sequence having at least 90% identity to a nucleotide sequence of (a);
   (c) a fragment of a nucleotide sequence of (a) or (b);
   (d) a nucleotide sequence being complementary to a nucleotide sequence of (a), (b) or (c); or
   (e) a nucleotide sequence which is redundant as a result of the degeneracy of the genetic code compared to any of the above-given nucleotide sequences.

2. An oligonucleotide primer comprising part of an HCBI polynucleic acid of paragraph 1, said primer being capable of acting as primer for specifically sequencing or specifically amplifying the nucleic acid of a certain HCBI isolate containing a nucleotide sequence of paragraph 1.

3. An oligonucleotide probe comprising part of an HVBI polynucleic acid of paragraph 1, said probe being capable of acting as a hybridization probe for specific detection of the nucleic acid of a certain HCBI isolate containing a nucleotide sequence of paragraph 1.

4. The oligonucleotide primer of paragraph 2 or the oligonucleotide probe of paragraph 3, which is detectably labelled or attached to a solid support.

5. The oligonucleotide primer of paragraph 2 or the oligonucleotide probe of paragraph 3 having a length of at least 13 bases.

6. An expression vector comprising an HCBI polynucleic acid of any one of paragraphs 1 to 5 operably linked to prokaryotic, eukaryotic or viral transcription and translation control elements.

7. A host cell transformed with an expression vector according to paragraph 6.

8. A polypeptide being encoded by an HCBI polynucleic acid of paragraph 1.

9. An antibody or antigen binding fragment thereof specifically binding to a polypeptide of paragraph 8.

10. The antibody or antigen binding fragment thereof of paragraph 9, wherein said antibody or fragment is detectably labelled.

11. A diagnostic kit for use in determining the presence of an HCBI polynucleic acid of paragraph 1 or a polypeptide of paragraph 8, said kit comprising a primer according to paragraph 2, 4 or 5, a probe according to any one of paragraphs 3 to 5, or an antibody or fragment thereof according to paragraph 9 or 10.

12. Use of a primer according to paragraph 2, 4 or 5, a probe according to any one of paragraphs 3 to 5, a polypeptide of paragraph 8, or an antibody or fragment thereof according to paragraph 9 or 10 for the preparation of a diagnostic composition for the diagnosis of a predisposition or an early stage of cancer or a disease of the CNS.

13. A method for the detection of an HCBI polynucleic acid according to paragraph 1 in a biological sample, comprising: (a) optionally extracting sample polynucleic acid, (b) amplifying the polynucleic acid as described above with at least one primer according to paragraph 2, 4 or 5, optionally a labelled primer, and (c) detecting the amplified polynucleic acid.

14. A method for the detection of an HBCI polynucleic acid according to paragraph 1 in a biological sample, comprising: (a) optionally extracting sample polynucleic acid, (b) hybridizing the polynucleic acid as described above with at least one probe according to any one of paragraphs 3 to 5, optionally a labelled probe, and (c) detecting the hybridized polynucleic acid.

15. A method for detecting a polypeptide of paragraph 8 or an antibody of paragraph 9 present in a biological sample, comprising: (a) contacting the biological sample for the presence of such polypeptide or antibody as defined above, and (b) detecting the immunological complex formed between said antibody and said polypeptide.

16. An antisense oligonucleotide reducing or inhibiting the expression of an HCBI polynucleic acid of paragraph 1 or a vector containing said antisense oligonucleotide.

17. The antisense oligonucleotide of paragraph 16, which is an iRNA comprising a sense sequence and an antisense sequence, wherein the sense and antisense sequences form an RNA duplex and wherein the antisense sequence comprises a nucleotide sequence sufficiently complementary to the nucleotide sequence of an HCBI polynucleic acid of paragraph 1.

18. A pharmaceutical composition comprising the antibody or antigen binding fragment thereof of paragraph 9 or the antisense oligonucleotide of paragraph 16 or 17 and a suitable pharmaceutical carrier.

19. The antibody or antigen binding fragment thereof of paragraph 9 or the antisense oligonucleotide of paragraph 16 or 17 for use in a method of preventing or treating cancer or a disease of the CNS or early stages thereof. 20. The compounds of paragraph 19 for the use according to paragraph 19, wherein said cancer is colon cancer.

21. The compounds of paragraph 19 for the use according to paragraph 19, wherein said disease of the CNS is Alzheimer s disease or MS.

22. A vaccine comprising an HCBI polynucleic acid of paragraph 1 or a polypeptide according to paragraph 8.

23. An HCBI polynucleic acid of paragraph 1 or a polypeptide according to paragraph 8 for use in a method of immunizing a mammal against an HCBI infection.

24. Use of an HCBI polynucleic acid of paragraph 1 as a lead component for the development of a medicament for prevention or treatment of cancer.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An expression vector comprising a Healthy Cattle Blood Isolate (HCBI) polynucleic acid comprising:
   a nucleotide sequence depicted in any one of SEQ ID NOS. 1, 33, 55, 68 or 72,
   wherein the vector is adenoviral, vaccinia virus, avipox virus, herpes virus, or a retrovirus vector.

2. The expression vector of claim 1 wherein the retrovirus vector is Moloney murine leukemia virus (MoMuLV), Harvey murine sarcoma virus (HaMuSV), murine mammary tumor virus (MuMTV), Rous sarcoma virus (RSV), gibbon ape leukemia virus (GaLV).

3. A host cell transformed with an expression vector according to claim 1.

4. A host cell transformed with an expression vector according to claim 2.

5. The host cell of claim 3, wherein the cell is a Chinese hamster cell, a monkey cell, a baby hamster kidney cell, a pig kidney cell, a rabbit kidney cell, a human osteosarcoma cell, a HeLa cell a human hepatoma cell, or an insect cell.

6. The host cell of claim 4, wherein the cell is a Chinese hamster cell, a monkey cell, a baby hamster kidney cell, a pig kidney cell, a rabbit kidney cell, a human osteosarcoma cell, a HeLa cell a human hepatoma cell, or an insect cell.

7. The host cell of claim 5, wherein the monkey cell is a COS or Vero cell, the pig kidney cell is a PK15 cell, the rabbit kidney cell is a RK13 cell, the human osteosarcoma cell is a 143B cell line cell, the human heptoma cell is a Hep G2 cell, and the insect cell is a *Spodoptera frugiperda* cell.

8. The host cell of claim 6, wherein the monkey cell is a COS or Vero cell, the pig kidney cell is a PK15 cell, the rabbit kidney cell is a RK13 cell, the human osteosarcoma cell is a 143B cell line cell, the human heptoma cell is a Hep G2 cell, and the insect cell is a *Spodoptera frugiperda* cell.

* * * * *

SEQUENCE LISTING

```
<160> NUMBER OF SEQ ID NOS: 83

<210> SEQ ID NO 1
<211> LENGTH: 2251
<212> TYPE: DNA
<213> ORGANISM: artificial sequences
<220> FEATURE:
<221> NAME/KEY: source
<222> LOCATION: 1..2251
<223> OTHER INFORMATION: /mol_type="DNA"
      /note="HCBI 1.225"
      /organism="artificial sequences"

<400> SEQUENCE: 1 cctttccct  gattacaagc  tcccatctgc  tccagatcgg  gagcttttag  ccatcccgaa      60
tgggtggcga  cacaaattac  aggcgaaaaa  aaagaccata  ttggccttcg  gtttagattg     120
gctgccgtat  cagccaattt  gattgagtgc  cgcatcactc  aatctatcaa  gtgccgcatc     180
acctgattac  tcaaatctac  atgaaatttt  ctttcttgca  aacggttcag  aaaagcatta     240
taaatatccc  accaatgaat  cataaatgaa  tcactataga  tcaggaaaca  actatgaaac     300
tccataatcc  aaatccaaat  gagcctacta  acctacaaat  gcttgttgca  gaagttaaaa     360
aatccgcttc  aagctcttat  cacggtggtt  atattcaagt  tcctttccgt  gttgagtttg     420
catcatatac  acgccttgag  gcacttgtta  aacatactgg  ctcaagtcgc  aataagatca     480
tgaatgatct  gttaagaatc  ggtattgaaa  ctctagctgc  ctctttggat  gatgaaacaa     540
ttaaaactct  ttttgaaatt  gaaacctcaa  tcactgcgga  tctctatgct  tcaggaaaaa     600
ttaaatcagg  ggatcaatca  gatgattaat  ttacaaggaa  ctctaattaa  tgcttttcgt     660
gtggatggtg  gtaaaggtaa  agacggcaaa  gaatatgaag  cgcgtgacaa  ggtgcaaatt     720
cttggttcgt  tggagttacc  caatgggggaa  attaaacacg  aacttgttga  cctaacagtt     780
gaggattctc  gacttttga   accattcaaa  aatcaggtta  ttagcatctc  atgtggtgct     840
atggctgtcg  gtcgtaatgt  tatttttat   gttcgcaaag  gcgcaaaacc  agttttagca     900
```

```
gaacaaatgt gaaacccgaa aaaaaaaaca gtgagttagc gaagcaactc gatactattg    960
attaactagg ggacaaaaat tgactataaa agacaataaa aaagcccata attcggatgc   1020
tttggcgggc gatgaattac aggctttgca atctgctaag gcagatcaac acagggatag   1080
aataacacgt tttggaattt tgaaacatag agcgaagcta caagaacaat atttgtggac   1140
gcaagttgat tttaaatccg aaggtgaaaa tgatctatct aataaggctc ttaaggctgc   1200
aaccaaactc aagggatgcg gtcaatttct cttattccat aattactaca caatagacca   1260
agttaaactt gctaaggcct attactgttc tcagcatttg ctatgtccta tgtgtgctgg   1320
tgtaagggct gctaagtcaa tgagtcgtta tattcagcgt attgaagaac taatgcgcca   1380
gaatcgccat ttaaagcccg tcctgatcac tttgacggta agaatggcc ctgacctaca   1440 agaacgcttc aaacacctta gagcatcatt tagaacgctt ttagatcgtt ataacgatta   1500
caagaaaaaa ggtcgtggtt ttaatcagtt ttgtaaaatt gatggtgctt tttattcaac   1560
tgaatataca tacaatccaa aaactaaaga atggcatccg catattcata tttttgcctt   1620
actcaatcaa tggatagacc aggaagaatt gtccgaaact tggcacgata ttactctgga   1680
ttcttatatc gtcgatattc gtagagttaa aaaaaccaaa gaacacggct atagcaaagc   1740
tgttgctgag gtatgtaaat acgcccttaa gtttagtgat ctctcactgg agaacacttg   1800
ggaggcatat ctttctttga aaggtaacag gcttactggc tgttttggtt ctatgtatgg   1860
tgtcaaattg cctgaaaaac ttactgatga tctacccctt gatgatcttc catatttgga   1920
gctgttatac cgttttgttt ttggtaaaaa atcttattac aacctagaaa taacaaaaga   1980
cgtaaagcca caaaactagg actacaacga tgaggtgagg gcgacgcgcg accgtgcgcg   2040
ctacttcgtg catgtacgcg cgcgcctttg cctctttgtt gcgaggtgtg gacgaaaaaa   2100
gcaaggatac atacagaccc ctgcatgacc ttgtaagggg ttcgacccct tagaccccaa   2160
agggcgcact tatgcaaact cttcgagttc gccagtgctc ccaccagtaa cagagggcgc   2220
ggagtgcgcc cgaactgacg ctatagaatt c                                 2251
```

<210> SEQ ID NO 2
<211> LENGTH: 232
<212> TYPE: PRT
<213> ORGANISM: artificial sequences
<220> FEATURE:
<221> NAME/KEY: SOURCE
<222> LOCATION: 1..232
<223> OTHER INFORMATION: /mol_type="protein"
     /note="Sphinx2.36 ORF 229 amino acids"
     /organism="artificial sequences"

<400> SEQUENCE: 2

```
Met Gln Glu Gln Tyr Leu Trp Thr Gln Val Asp Phe Lys Val Gly Ser
1               5                   10                  15

Glu Thr Ser Ile Lys Ala Leu Lys Ala Ala Thr Lys Leu Lys Gly Cys
            20                  25                  30

Gly Gln Phe Leu Leu Phe Arg Asn Tyr Tyr Thr Ile Asp Gln Ile Lys
        35                  40                  45

Leu Glu Lys Phe His Val Cys Gly Gln His Leu Leu Cys Pro Met Cys
    50                  55                  60

Ala Gly Ile Arg Ala Ala Arg Ser Met Asn Arg Tyr Ile Gln Arg Ile
65                  70                  75                  80

Glu Glu Ile Met Arg Gln Asn Arg Lys Leu Lys Pro Val Leu Ile Thr
                85                  90                  95

Leu Thr Val Lys Asn Gly Glu Asp Leu Gln Glu Arg Phe Glu His Leu
```

```
                        100                 105                 110
Thr Gly Ser Phe Lys Thr Leu Leu Gln Arg Tyr Arg Asp Phe Lys Lys
            115                 120                 125

Lys Gly Arg Gly Phe Asn Gln Phe Cys Lys Ile Asp Gly Gly Phe Tyr
130                 135                 140

Thr Thr Glu Tyr Thr Tyr Asn Glu Thr Gln Gln Trp His Pro His
145                 150                 155                 160

Ile His Ile Phe Ala Leu Val Thr Asp Arg Ile Asp Gln Glu Leu
                165                 170                 175

Ala Glu Thr Trp His Asp Ile Thr Leu Asp Ser Tyr Ile Val Asp Ile
            180                 185                 190

Arg Arg Val Lys Lys Thr Lys Glu His Gly Tyr Ala Lys Ala Val Ala
            195                 200                 205

Glu Val Cys Lys Tyr Ala Leu Lys Phe Ser Asp Leu Ser Thr Glu Lys
        210                 215                 220

Thr Phe Gln Ala Phe Phe Asp Pro
225                 230
```

<210> SEQ ID NO 3
<211> LENGTH: 229
<212> TYPE: PRT
<213> ORGANISM: artificial sequences
<220> FEATURE:
<221> NAME/KEY: SOURCE
<222> LOCATION: 1..229
<223> OTHER INFORMATION: /mol_type="protein"
      /note="HCBI ORF 229aa"
      /organism="artificial sequences"

<400> SEQUENCE: 3

```
Met Cys Ala Gly Val Arg Ala Ala Lys Ser Met Ser Arg Tyr Ile Gln
1               5                   10                  15

Arg Ile Glu Glu Leu Met Arg Gln Asn Arg His Leu Lys Pro Val Leu
            20                  25                  30

Ile Thr Leu Thr Val Lys Asn Gly Pro Asp Leu Gln Glu Arg Phe Lys
        35                  40                  45

His Leu Arg Ala Ser Phe Arg Thr Leu Leu Asp Arg Tyr Asn Asp Tyr
    50                  55                  60

Lys Lys Lys Gly Arg Gly Phe Asn Gln Phe Cys Lys Ile Asp Gly Ala
65                  70                  75                  80

Phe Tyr Ser Thr Glu Tyr Thr Tyr Asn Pro Lys Thr Lys Glu Trp His
                85                  90                  95

Pro His Ile His Ile Phe Ala Leu Leu Asn Gln Trp Ile Asp Gln Glu
            100                 105                 110

Glu Leu Ser Glu Thr Trp His Asp Ile Thr Leu Asp Ser Tyr Ile Val
        115                 120                 125

Asp Ile Arg Arg Val Lys Lys Thr Lys Glu His Gly Tyr Ser Lys Ala
    130                 135                 140

Val Ala Glu Val Cys Lys Tyr Ala Leu Lys Phe Ser Asp Leu Ser Leu
145                 150                 155                 160

Glu Asn Thr Trp Glu Ala Tyr Leu Ser Leu Lys Gly Asn Arg Leu Thr
                165                 170                 175

Gly Cys Phe Gly Ser Met Tyr Gly Val Lys Leu Pro Glu Lys Leu Thr
            180                 185                 190

Asp Asp Leu Pro Leu Asp Asp Leu Pro Tyr Leu Glu Leu Leu Tyr Arg
        195                 200                 205
```

```
Phe Val Phe Gly Lys Lys Ser Tyr Tyr Asn Leu Glu Ile Thr Lys Asp
        210                 215                 220

Val Lys Pro Gln Asn
225
```

<210> SEQ ID NO 4
<211> LENGTH: 96
<212> TYPE: PRT
<213> ORGANISM: artificial sequences
<220> FEATURE:
<221> NAME/KEY: SOURCE
<222> LOCATION: 1..96
<223> OTHER INFORMATION: /mol_type="protein"
      /note="Sphinx 96aa"
      /organism="artificial sequences"

<400> SEQUENCE: 4

```
Met Ile Asn Leu Gln Gly Thr Leu Ile Asn Ala Phe Arg Leu Asp Gly
1               5                   10                  15

Gly Lys Gly Lys Asp Gly Lys Glu Tyr Glu Ala Arg Asp Lys Val Gln
            20                  25                  30

Ile Leu Gly Ser Leu Glu Leu Pro Asn Gly Glu Ile Lys His Glu Leu
        35                  40                  45

Val Asp Leu Thr Val Glu Asp Ala Arg Ile Phe Glu Pro Phe Lys His
    50                  55                  60

Lys Val Ile Ser Ile Ser Cys Gly Ala Met Ala Ile Gly Arg Asn Val
65                  70                  75                  80

Val Phe Tyr Val Arg Lys Gly Ala Lys Pro Val Leu Ala Asp Val Met
                85                  90                  95
```

<210> SEQ ID NO 5
<211> LENGTH: 127
<212> TYPE: PRT
<213> ORGANISM: artificial sequences
<220> FEATURE:
<221> NAME/KEY: SOURCE
<222> LOCATION: 1..127
<223> OTHER INFORMATION: /mol_type="protein"
      /note="HCBI 96aa"
      /organism="artificial sequences"

<400> SEQUENCE: 5

```
Met Met Lys Gln Leu Lys Leu Phe Leu Lys Leu Lys Pro Gln Ser Leu
1               5                   10                  15

Arg Ile Ser Met Leu Gln Glu Lys Leu Asn Gln Gly Ile Asn Gln Met
            20                  25                  30

Ile Asn Leu Gln Gly Thr Leu Ile Asn Ala Phe Arg Val Asp Gly Gly
        35                  40                  45

Lys Gly Lys Asp Gly Lys Glu Tyr Glu Ala Arg Asp Lys Val Gln Ile
    50                  55                  60

Leu Gly Ser Leu Glu Leu Pro Asn Gly Glu Ile Lys His Glu Leu Val
65                  70                  75                  80

Asp Leu Thr Val Glu Asp Ser Arg Leu Phe Glu Pro Phe Lys Asn Gln
                85                  90                  95

Val Ile Ser Ile Ser Cys Gly Ala Met Ala Val Gly Arg Asn Val Ile
            100                 105                 110

Phe Tyr Val Arg Lys Gly Ala Lys Pro Val Leu Ala Glu Gln Met
        115                 120                 125
```

<210> SEQ ID NO 6
<211> LENGTH: 124

<212> TYPE: PRT
<213> ORGANISM: artificial sequences
<220> FEATURE:
<221> NAME/KEY: SOURCE
<222> LOCATION: 1..124
<223> OTHER INFORMATION: /mol_type="protein"
     /note="Sphinx 111aa"
     /organism="artificial sequences"

<400> SEQUENCE: 6

Met Asn His Lys Leu Ile Ala Ile Asp Gln Glu Leu Thr Met Lys Leu
1               5                   10                  15

His Asn Pro Asn Pro Asn Glu Pro Thr Asn Leu Gln Met Leu Val Ala
            20                  25                  30

Glu Ile Lys Lys Ser Ala Ser Ser Ser Tyr His Gly Gly Tyr Ile Gln
        35                  40                  45

Val Pro Phe Arg Val Glu Cys Ala Ser Tyr Thr Arg Leu Glu Ala Leu
    50                  55                  60

Val Lys His Thr Gly Ser Ser Arg Asn Lys Ile Met Asn Asp Leu Leu
65                  70                  75                  80

Arg Ile Gly Ile Glu Thr Leu Ala Ala Ser Leu Asp Asp Glu Thr Ile
                85                  90                  95

Lys Thr Leu Phe Glu Ile Glu Thr Ser Ile Thr Ala Asp Leu Tyr Ala
            100                 105                 110

Ser Gly Lys Met Lys Ser Gly Asp Gln Ser Asp Asp
        115                 120

<210> SEQ ID NO 7
<211> LENGTH: 111
<212> TYPE: PRT
<213> ORGANISM: artificial sequences
<220> FEATURE:
<221> NAME/KEY: SOURCE
<222> LOCATION: 1..111
<223> OTHER INFORMATION: /mol_type="protein"
     /note="HCBI 111aa"
     /organism="artificial sequences"

<400> SEQUENCE: 7

Met Lys Leu His Asn Pro Asn Pro Asn Glu Pro Thr Asn Leu Gln Met
1               5                   10                  15

Leu Val Ala Glu Val Lys Lys Ser Ala Ser Ser Ser Tyr His Gly Gly
            20                  25                  30

Tyr Ile Gln Val Pro Phe Arg Val Glu Phe Ala Ser Tyr Thr Arg Leu
        35                  40                  45

Glu Ala Leu Val Lys His Thr Gly Ser Ser Arg Asn Lys Ile Met Asn
    50                  55                  60

Asp Leu Leu Arg Ile Gly Ile Glu Thr Leu Ala Ala Ser Leu Asp Asp
65                  70                  75                  80

Glu Thr Ile Lys Thr Leu Phe Glu Ile Glu Thr Ser Ile Thr Ala Asp
                85                  90                  95

Leu Tyr Ala Ser Gly Lys Ile Lys Ser Gly Asp Gln Ser Asp Asp
            100                 105                 110

<210> SEQ ID NO 8
<211> LENGTH: 898
<212> TYPE: DNA
<213> ORGANISM: artificial sequences
<220> FEATURE:
<221> NAME/KEY: source
<222> LOCATION: 1..898
<223> OTHER INFORMATION: /mol_type="DNA"

/note="HQ444405"
          /organism="artificial sequences"

<400> SEQUENCE: 8
ataatttgcg gtcactgtgc cgaatcacta cgcaatattt tattacccat aatttaacca      60
attcttaatt tcttgcaaac ggttcaaaaa agcattataa atatctcacc aatgaatcat     120
aaactaatcg ctatagatca ggaattaact atgaaactcc ataatccaaa tccaaatgag     180
cctactaacc tgcaaatgct tgttgcagaa attaaaaaat ccgcttcaag ctcttatcac     240
ggtggctata ttcaagttcc tttccgtgtt gagtgtgcat catatacacg ccttgaagca     300
cttgttaaac atactggctc aagtcgcaat aagatcatga atgatctctt aagaatcggt     360
attgaaactc tagctgcctc tttggacgac gaaacaatta aaactctttt tgaaattgaa     420
acttcaatca ctgcggatct ctatgcttca ggaaaaatga atcaggaga tcagtcagat     480 gattaattta caagggacac ttataaatgc ttttcgtctt gatggtggta aagggaaaga     540
cggcaaagaa tatgaagcac gtgacaaggt gcaaattctt ggttcgctgg agttgcccaa     600
cggtgagatc aaacatgagc ttgttgactt aacggttgaa gatgctcgca tctttgagcc     660
attcaaacac aaggtaatta gcatttcatg cggtgctatg gctatcggtc gaaatgttgt     720
tttttatgtt cgaaaaggtg caaagcctgt tttagcagat gtaatgtaat tcatgaaaaa     780
aaacagtgag ttaggcttgc cgactcgctg tttttctttt tacttgatac tattaactaa     840
agtggggaca aaattgacta aaaagacaa taaaaaagcc cataattctg atgctttg      898

<210> SEQ ID NO 9
<211> LENGTH: 958
<212> TYPE: DNA
<213> ORGANISM: artificial sequences
<220> FEATURE:
<221> NAME/KEY: source
<222> LOCATION: 1..958
<223> OTHER INFORMATION: /mol_type="DNA"
          /note="CU459139"
          /organism="artificial sequences"

<400> SEQUENCE: 9 aaaactatt atttcgtta gctaagatta aagaaaatta tcatgccgat gtaaaaaacg        60
atgaatctat tcgcgccatg aaaactgccc aaaaattaaa tgggtgcggt aattttcttc     120
tattcaaaaa ttttttacacc attaatcaaa ttaaactcgc caagttccaa gcttgtagtg     180
agcatttgtt atgtccgttt tgtgctggta ttagagcttc taaggcaatt caaaaatact     240
ctgagcgtgt tgatcaagtc ttatctgaaa atcctcgttt aaagcccgtt atgatcacgt     300
ttacggttaa aaatggggta gacctagggg aacggttcac ccatcttata aaatcgttta     360
gaacgcttat agagcgtcgt agggactata ttaaaaaagg gcgtggcttt aatgaattt      420 gcaaaattaa tggtgcgatg tattcatatg agaatactta caatgaaaaa actaatgaat     480
ggcatcctca tattcatatg tttgcacttt tggatgattg gatagatcag gatgaattgt     540
ctcaatattg gcaatccatt actggggact ctatggtcgt tgatattcgt agagccaaaa     600
aacaaaaaga cttaggctat tcaggtgctg ctgctgaagt ctgtaaatat gctctcaaat     660
ttggtgatct ttctgtagaa aagacttggg aagctttcaa agttttgaaa ggtaagcgat     720
taagtggggc ttttggatct ctttgggcg tgaaaattcc tgaatcattg atagatgatc     780
ttccagacga ttctgattta ccttatttag aaatgattta agttcgtc ttttctaaga     840 agtcttatta cgatttacaa cttactcgtc atgtcgaacc tacaggtaag gacgacgccg     900
acgagcttcg aggagaagaa ggacgcaacc tgttggtgag catggacggg cgaggagc        958

<210> SEQ ID NO 10
<211> LENGTH: 959
<212> TYPE: DNA
<213> ORGANISM: artificial sequences
<220> FEATURE:
<221> NAME/KEY: source
<222> LOCATION: 1..959
<223> OTHER INFORMATION: /mol_type="DNA"
       /note="JN872565"
       /organism="artificial sequences"

<400> SEQUENCE: 10
aaaattattt atttaccctg gctaagttta aagagaacta tgaaaaagac gttaaaaacg         60
aagaatctat caaggctcta aaatctgctc agaaattgaa tgaatgcgga aactatctgc        120
tattcaaaaa ttttttacaca ataggcgaag ttaaactctc caagctccgc acctgcggac       180
agcatttgct ttgcccttttc tgtgctgcca ttcgtgcttc tcgtgctatc caaaaatacg       240
ttgaacgtat tgatcaagtc ctgcaagaaa tcgcaagct caagcccgtt ctaatcacgc         300
tcaccgttaa aaacggctct gacctagcag aacgctccga acatcttatg aagtccttta       360
gaacgctcct agagcgtcgt agggactatg aaaagaaagg tcgaggtttt aatgagttct       420
gtaaggttca aggggctatg tactcctatg aaaatacatt caatgaaaaa acaggcgaat        480
ggcatccgca tattcatatg ttcgctttgg ttgatcaatg gattgatcag caagagttt         540 cagaatattg gcatagcctt actggggact cgatggttgt cgatgtccgc agggcaagaa        600
aagaaaaagg ttacggttat agcaaagcgg ctgccgaagt ctgtaagtat gctttgaagt       660
ttggtgatct gtccgttgaa aagacttggg aagcatttaa ggttcttaag ggaaagcgtt       720
taacaggttc ttttggtctg ctatggggtg tcaaaatccc tgactcaatg acagacgatt       780
gccatcagaa gacttgccat atctcgaaat gctgtacaag tttgcctaca gtaaaaagtc       840
ttactacgac ttactaatca caaggcacgt agagccacaa ccgcatgagg acgagcgtgc       900
gaggagcttc gacgagtgcg attgtattta tgcggtggag gctcagacgt tgactgtg         959

<210> SEQ ID NO 11
<211> LENGTH: 690
<212> TYPE: DNA
<213> ORGANISM: artificial sequences
<220> FEATURE:
<221> NAME/KEY: source
<222> LOCATION: 1..690
<223> OTHER INFORMATION: /mol_type="DNA"
       /note="Blast N2 Query1"
       /organism="artificial sequences"

<400> SEQUENCE: 11
tttcttgcaa acggttcaga aaagcattat aaatatccca ccaatgaatc ataaatgaat         60
cactatagat caggaaacaa ctatgaaact ccataatcca aatccaaatg agcctactaa        120
cctacaaatg cttgttgcag aagttaaaaa atccgcttca agctcttatc acggtggtta       180
tattcaagtt cctttccgtg ttgagtttgc atcatataca cgccttgagg cacttgttaa       240
acatactggc tcaagtcgca ataagatcat gaatgatctg ttaagaatcg gtattgaaac       300
tctagctgcc tctttggatg atgaaacaat taaaactctt tttgaaattg aaacctcaat       360
cactgcggat ctctatgctt caggaaaaat taaatcaggg gatcaatcag atgattaatt       420
tacaaggaac tctaattaat gcttttcgtg tggatggtgg taaaggtaaa gacggcaaag       480
aatatgaagc gcgtgacaag gtgcaaattc ttggttcgtt ggagttaccc aatggggaat       540

```
tcgcaaaggc gcaaaaccag ttttagcaga atcaggttat tagcatctca tgtggtgcta    600
tggctgtcgg tcgtaatgtt attttttatg ttaaacacga acttgttgac ctaacagttg    660
aggattctcg acttttgaa ccattcaaaa                                      690
```

<210> SEQ ID NO 12
<211> LENGTH: 692
<212> TYPE: DNA
<213> ORGANISM: artificial sequences
<220> FEATURE:
<221> NAME/KEY: source
<222> LOCATION: 1..692
<223> OTHER INFORMATION: /mol_type="DNA"
      /note="BlastN2 Query1"
      /organism="artificial sequences"

<400> SEQUENCE: 12

```
tttcttgcaa acggttcaaa aaagcattat aaatatctca ccaatgaatc ataaactaat    60
cgctatagat caggaattaa ctatgaaact ccataatcca aatccaaatg agcctactaa   120
cctgcaaatg cttgttgcag aaattaaaaa atccgcttca agctcttatc acggtggcta   180
tattcaagtt cctttccgtg ttgagtgtgc atcatataca cgccttgaag cacttgttaa   240
acatactggc tcaagtcgca ataagatcat gaatgatctc ttaagaatcg gtattgaaac   300
tctagctgcc tctttggacg acgaaacaat taaaactctt tttgaaattg aaacttcaat   360
cactgcggat ctctatgctt caggaaaaat gaaatcagga gatcagtcag atgattaatt   420
tacaagggac acttataaat gcttttcgtc ttgatggtgg taaagggaaa gacggcaaag   480
aatatgaagc acgtgacaag gtgcaaattc ttggttcgct ggagttgccc aacggtgaga   540
ttcgaaaagg tgcaaagcct gttttagcag astcaaacat gagcttgttg acttaacggt   600
tgaagatgct cgcatctttg agccattcaa acacaaggta attagcattt catgcggtgc   660
tatggctatc ggtcgaaatg ttgttttta tg                                   692
```

<210> SEQ ID NO 13
<211> LENGTH: 132
<212> TYPE: DNA
<213> ORGANISM: artificial sequences
<220> FEATURE:
<221> NAME/KEY: source
<222> LOCATION: 1..132
<223> OTHER INFORMATION: /mol_type="DNA"
      /note="BlastN2 Query2"
      /organism="artificial sequences"

<400> SEQUENCE: 13

```
aaaattgact ataaaagaca ataaaaaagc ccataattcg gatgctttgg cgggcgatga    60
attacaggct ttgcaatctg ctaaggcaga tcaacacagg gatagaataa cacgttttgg   120
aattttgaaa ca                                                        132
```

<210> SEQ ID NO 14
<211> LENGTH: 132
<212> TYPE: DNA
<213> ORGANISM: artificial sequences
<220> FEATURE:
<221> NAME/KEY: source
<222> LOCATION: 1..132
<223> OTHER INFORMATION: /mol_type="DNA"
      /note="BlastN2 Subject2"
      /organism="artificial sequences"

<400> SEQUENCE: 14

```
acttttgaaa caattacagg ctttgcaatc tgctaatgca gatcaacaca gggatagaat    60
atcacgtttt ggaaaattga ctaaaaaaga caataaaaaa gcccataatt ctgatgcttt   120
ggcgggcgac ga                                                       132
```

```
<210> SEQ ID NO 15
<211> LENGTH: 380
<212> TYPE: DNA
<213> ORGANISM: artificial sequences
<220> FEATURE:
<221> NAME/KEY: source
<222> LOCATION: 1..380
<223> OTHER INFORMATION: /mol_type="DNA"
      /note="lastN2 Query3"
      /organism="artificial sequences"

<400> SEQUENCE: 15
```

```
cagcatttgc tatgtcctat gtgtgctggt gtaagggctg ctaagtcaat gagtcgttat    60
attcagcgta ttgaagaact aatgcgccag aatcgccatt taaagcccgt cctgatcact   120
ttgacggtaa agaatggccc tgacctacaa gaacgcttca aacaccttag agcatcattt   180
agaacgcttt tagatcgtta taacgattac aagaaaaaag gtcgtggttt taatcagttt   240
tgtaaaattg atggtgcttt ttattcaact gaatatacat acaatccaaa aactaaagaa   300
tggcatccgc atattcatat ttttgcctta ctcaatcaat ggatagacca ggaagaattg   360
tccgaaactt ggcacgatat                                               380
```

```
<210> SEQ ID NO 16
<211> LENGTH: 380
<212> TYPE: DNA
<213> ORGANISM: artificial sequences
<220> FEATURE:
<221> NAME/KEY: source
<222> LOCATION: 1..380
<223> OTHER INFORMATION: /mol_type="DNA"
      /note="BlastN2 Subject3"
      /organism="artificial sequences"

<400> SEQUENCE: 16
```

```
cagcatttgc tatgtccaat gtgtgctggt attcgtgctg cccgttcaat gaatcggtat    60
attcaacgca tcgaagaaat aatgcgtcag aatcgcaagc taaagcccgt attgatcact   120
ttgaccgtta agaacggtga agacctacag gaacgctttg aacacctcac aggctcattt   180
aagacgcttt tacagcgtta ccgtgatttt aagaaaaagg gtcgagggtt taatcaattt   240
tgcaaaattg atggcggttt ttatacgacc gaatacacct acaacgaaac aacccaacaa   300
tggcatccgc atattcatat ttttgcgtta gtgactgacc ggattgacca ggaggaacta   360
gcagaaactt ggcacgatat                                               380
```

```
<210> SEQ ID NO 17
<211> LENGTH: 43
<212> TYPE: DNA
<213> ORGANISM: artificial sequences
<220> FEATURE:
<221> NAME/KEY: source
<222> LOCATION: 1..43
<223> OTHER INFORMATION: /mol_type="DNA"
      /note="BlastN2 Query4"
      /organism="artificial sequences"

<400> SEQUENCE: 17
```

```
cttgtaaggg gttcgacccc ttagacccca aagggcgcac tta                     43
```

```
<210> SEQ ID NO 18
<211> LENGTH: 43
<212> TYPE: DNA
<213> ORGANISM: artificial sequences
<220> FEATURE:
<221> NAME/KEY: source
<222> LOCATION: 1..43
<223> OTHER INFORMATION: /mol_type="DNA"
      /note="BlastN2 Subject4"
      /organism="artificial sequences"

<400> SEQUENCE: 18
cttgtaaggg ggtcggcccc ttagacccca aagggcgcac tta          43

<210> SEQ ID NO 19
<211> LENGTH: 83
<212> TYPE: DNA
<213> ORGANISM: artificial sequences
<220> FEATURE:
<221> NAME/KEY: source
<222> LOCATION: 1..83
<223> OTHER INFORMATION: /mol_type="DNA"
      /note="BlastN2 Query5"
      /organism="artificial sequences"

<400> SEQUENCE: 19
cttccatatt tggagctgtt ataccgtttt gttttggta aaaaatctta ttacaaccta    60
gaaataacaa aagacgtaaa gcc                                           83

<210> SEQ ID NO 20
<211> LENGTH: 83
<212> TYPE: DNA
<213> ORGANISM: artificial sequences
<220> FEATURE:
<221> NAME/KEY: source
<222> LOCATION: 1..83
<223> OTHER INFORMATION: /mol_type="DNA"
      /note="BlastN2 Subject5"
      /organism="artificial sequences"

<400> SEQUENCE: 20
cttccatatc ttgagctgct ctatcgtttc gttttggtg aaaggtctta ttacaaccta    60
gagttaacta aggacgtaaa gcc                                           83

<210> SEQ ID NO 21
<211> LENGTH: 269
<212> TYPE: DNA
<213> ORGANISM: artificial sequences
<220> FEATURE:
<221> NAME/KEY: source
<222> LOCATION: 1..269
<223> OTHER INFORMATION: /mol_type="DNA"
      /note="BlastN2 Query6"
      /organism="artificial sequences"

<400> SEQUENCE: 21
atgattaatt tacaaggaac tctaattaat gcttttcgtg tggatggtgg taaaggtaaa    60
gacggcaaag aatatgaagc gcgtgacaag gtgcaaattc ttggttcgtt ggagttaccc   120
attttttatg ttcgcaaagg cgcaaaaccc cattcaaaaa tcaggttatt agcatctcat   180
gtggtgctat ggctgtcggt cgtaatgtta atggggaaat taaacacgaa cttgttgacc   240
taacagttga ggattctcga cttttttgaa                                    269

<210> SEQ ID NO 22
<211> LENGTH: 269
<212> TYPE: DNA
```

```
<213> ORGANISM: artificial sequences
<220> FEATURE:
<221> NAME/KEY: source
<222> LOCATION: 1..269
<223> OTHER INFORMATION: /mol_type="DNA"
      /note="BlastN2 Subject6"
      /organism="artificial sequences"

<400> SEQUENCE: 22
atgattaatt tacaaggaac tctaatcaat gctttccgta tggacggtgg taagggtaaa      60
gttttttatg ttcgaaaagg tgcaaaacca atggagagat taaacacgaa cttgttgacc     120
tcacagttga tgatgccagt gtctaccagc cactaaaaaa taagtaatt tctatttcct      180 gcggtgctat ggctgtaggt cgtaatgttg atgggaaaga gtacgaagcg cgtgacaagg     240
tacaaatact tggttcgctg gaactaccc                                       269

<210> SEQ ID NO 23
<211> LENGTH: 160
<212> TYPE: DNA
<213> ORGANISM: artificial sequences
<220> FEATURE:
<221> NAME/KEY: source
<222> LOCATION: 1..160
<223> OTHER INFORMATION: /mol_type="DNA"
      /note="BlastN2 Query7"
      /organism="artificial sequences"

<400> SEQUENCE: 23
acagggatag aataacacgt tttggaattt tgaaacatag attcggatgc tttggcgggc      60
gatgaattac aggctttgca atctgctaag gcagatcaac gatactattg attaactagg     120
ggacaaaaat tgactataaa agacaataaa aaagcccata                           160

<210> SEQ ID NO 24
<211> LENGTH: 160
<212> TYPE: DNA
<213> ORGANISM: artificial sequences
<220> FEATURE:
<221> NAME/KEY: source
<222> LOCATION: 1..160
<223> OTHER INFORMATION: /mol_type="DNA"
      /note="BlastN2 Subject7"
      /organism="artificial sequences"

<400> SEQUENCE: 24
acagggatag aataacacgt tttgcgactt tgaaacatag tttcagaagc tttggcgggc      60
ggagaaatac aggctttgca atctgcaaac gcagatcaac gatactattg attaaagtgg     120
ggacaaaaat tgcttaaaaa agacaataaa aaagcccata                           160

<210> SEQ ID NO 25
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="BlastN2 Query8"
      /organism="artificial sequences"

<400> SEQUENCE: 25
gaatggcatc cgcatattca tat                                              23

<210> SEQ ID NO 26
<211> LENGTH: 23
```

```
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="BlastN2 Subject8"
      /organism="artificial sequences"

<400> SEQUENCE: 26
gaatggcatc cgcatattca tat                                           23

<210> SEQ ID NO 27
<211> LENGTH: 98
<212> TYPE: DNA
<213> ORGANISM: artificial sequences
<220> FEATURE:
<221> NAME/KEY: source
<222> LOCATION: 1..98
<223> OTHER INFORMATION: /mol_type="DNA"
      /note="BlastN2 Query9"
      /organism="artificial sequences"

<400> SEQUENCE: 27
ttcaaaaatc aggttattag catctcatgt ggtgctatgg ctgtcggtcg taatgttatt    60
ttttatgttc gcaaaggcgc aaaaccagtt ttagcaga                           98

<210> SEQ ID NO 28
<211> LENGTH: 98
<212> TYPE: DNA
<213> ORGANISM: artificial sequences
<220> FEATURE:
<221> NAME/KEY: source
<222> LOCATION: 1..98
<223> OTHER INFORMATION: /mol_type="DNA"
      /note="BlastN2 Subject9"
      /organism="artificial sequences"

<400> SEQUENCE: 28
ttcaaaaata agcttattag catcagttgt ggtgctatgg ctgttggtcg taacgttatt    60
ttttatgttc gaaaaggtgc gaaacctgtt ttagcaga                           98

<210> SEQ ID NO 29
<211> LENGTH: 64
<212> TYPE: DNA
<213> ORGANISM: artificial sequences
<220> FEATURE:
<221> NAME/KEY: source
<222> LOCATION: 1..64
<223> OTHER INFORMATION: /mol_type="DNA"
      /note="BlastN2 Query10"
      /organism="artificial sequences"

<400> SEQUENCE: 29
agaaagatca acacagggat agaataacac gttttggaat tttgaaacat agagcgaagc    60
taca                                                                64

<210> SEQ ID NO 30
<211> LENGTH: 64
<212> TYPE: DNA
<213> ORGANISM: artificial sequences
<220> FEATURE:
<221> NAME/KEY: source
<222> LOCATION: 1..64
<223> OTHER INFORMATION: /mol_type="DNA"
      /note="BlastN2 Subject10"
      /organism="artificial sequences"
```

```
<400> SEQUENCE: 30
agaaagatca acatagggat agaataacac gttttggcat tttgaaacat agatcgaagc    60
aaca                                                                64

<210> SEQ ID NO 31
<211> LENGTH: 113
<212> TYPE: DNA
<213> ORGANISM: artificial sequences
<220> FEATURE:
<221> NAME/KEY: source
<222> LOCATION: 1..113
<223> OTHER INFORMATION: /mol_type="DNA"
      /note="BlastN2 Query11"
      /organism="artificial sequences"

<400> SEQUENCE: 31
tatacataca atccaaaaac taaagaatgg catccgcata ttcatatttt tgcaaaaaag    60
gtcgtggttt aatcagtttt tgtaaaattg atggtgcttt ttattcaact gaa          113

<210> SEQ ID NO 32
<211> LENGTH: 113
<212> TYPE: DNA
<213> ORGANISM: artificial sequences
<220> FEATURE:
<221> NAME/KEY: source
<222> LOCATION: 1..113
<223> OTHER INFORMATION: /mol_type="DNA"
      /note="BlastN2 Subject11"
      /organism="artificial sequences"

<400> SEQUENCE: 32
aatacttaca atgaaaaaac taatgaatgg catcctcata ttcatatgtt tgcaaaaaag    60
ggcgtggctt taatgaattt tgcaaaatta atggtgcgat gtattcatat gag          113

<210> SEQ ID NO 33
<211> LENGTH: 1707
<212> TYPE: DNA
<213> ORGANISM: artificial sequences
<220> FEATURE:
<221> NAME/KEY: source
<222> LOCATION: 1..1707
<223> OTHER INFORMATION: /mol_type="DNA"
      /note="HCBI2.170"
      /organism="artificial sequences"

<400> SEQUENCE: 33
gaattcaata tgttcgcttc taaccattac aacgacttta ctggttctgg agatttatca    60
gatgattaaa ttagaaggaa tcgttttaaa cgtcttcact cagcaaggtg acaaaacaa    120 aaaaggcgaa tcatttgatg atcgtgacaa ggtacaaatt ttaggtgcta tggatctgcc   180
caatggtgat gtaaaaaatg agcttttttac gttatctgta gatgattatc gggactttaa  240
agacttccta aatcgaaaaa tttgtattgc tgttggtgca atggcaagtg gccgtaatgt   300 tatttttttat gttgctaaag gtgcaaagcc tatatcagca gaatttgcgt gaaacgctaa  360
aaaaaacagt gagttagcct tggcttctcg ctgtttttc tttctcttga tactattgat   420
taactagggg acaaaaattg actaaaaaag acaataaaaa agcccataat tcggacactt  480
tggcgggtga tgaattacag gctttgcaat ctgctaaggc agatcaacac agggatagaa   540
tatcacgttt tggactttg aaacatagag cgaagctaca agaacaatat tgtggacgc    600 aggttgattt caaatccgaa ggtgaaaatg agacatccaa taaggctctt aaggctgcaa   660
ccaaattaaa gggatgcggt caattttgc tattccataa ctactacaca attgaccaag    720
```

```
ttaaacttgc taaggcccat tattgttctc agcatttgct ttgccctatg tgtgctggtg      780
taagggctgc taagtcaatg agtagatatg ttcaacgtat tgaagaattg atgcgtcaga      840
atcgcaaatt aaagcccgta ttgatcactt taacggttaa gaatggggaa gacctagaag      900
aacgctttaa acacttagac gctcatttag gacgctttta gatcgttata acgattacaa      960
aaagaaaggt cgtggtttta atcaattctg caagattgat ggtgcttttt tattccactg     1020
aatataccta caattcaaaa acaaaagagt ggcatcccca tatccatatt ttcgctttac     1080
tcaatgaatg gatagaccag gaagaattgg ccgagacctg gcatgacatt accctggatt     1140
cttatatcgt agatattcgt agagttaaaa ggaccaaaga acacggctat agcaaagctg     1200
ttgcagaggt ttgtaaatat gctcttaagt ttagtgattt gtcacttgag aatacgtggg     1260
aagcttatct ttctttaaaa ggtaataggc ttactggctg ttttggttct atgtatggtg     1320
tcaagttgcc tgaaaaactc acagatgatt taccccttga tgatcttcca tatatggagc     1380
tgctataccg ttttgtcttt ggtaaaaaat aacattacgg ccacttgcca ttgcaccaac     1440
agcaatacaa attttttcgat ttaggaagtc tttaaagtcc cgataatcat ctacagataa     1500
cgtaaaaagc tcattttttta catcaccatt gggcagatcc atagcaccta aaatttgtac     1560
cttgtcacga tcatcaaatg attcgccttt tttgttttgt ccaccttgct gagtgaagac     1620
gtttaaaacg attccttcta atttaatcat ctgataaatc tccagaacca gtaaagtcgt     1680
tgtaatggtt agaagcgaac atatgaa                                          1707
```

<210> SEQ ID NO 34
<211> LENGTH: 96
<212> TYPE: PRT
<213> ORGANISM: artificial sequences
<220> FEATURE:
<221> NAME/KEY: SOURCE
<222> LOCATION: 1..96
<223> OTHER INFORMATION: /mol_type="protein"
      /note="Sphinx 2.36.96"
      /organism="artificial sequences"

<400> SEQUENCE: 34

```
Met Ile Asn Leu Gln Gly Thr Leu Ile Asn Ala Phe Arg Leu Asp Gly
1               5                   10                  15

Gly Lys Gly Lys Asp Gly Lys Glu Tyr Glu Ala Arg Asp Lys Val Gln
            20                  25                  30

Ile Leu Gly Ser Leu Glu Leu Pro Asn Gly Glu Ile Lys His Glu Leu
        35                  40                  45

Val Asp Leu Thr Val Glu Asp Ala Arg Ile Phe Glu Pro Phe Lys His
    50                  55                  60

Lys Val Ile Ser Ile Ser Cys Gly Ala Met Ala Ile Gly Arg Asn Val
65                  70                  75                  80

Val Phe Tyr Val Arg Lys Gly Ala Lys Pro Val Leu Ala Asp Val Met
                85                  90                  95
```

<210> SEQ ID NO 35
<211> LENGTH: 96
<212> TYPE: PRT
<213> ORGANISM: artificial sequences
<220> FEATURE:
<221> NAME/KEY: SOURCE
<222> LOCATION: 1..96
<223> OTHER INFORMATION: /mol_type="protein"
      /note="HCBI2.170.137"
      /organism="artificial sequences"

<400> SEQUENCE: 35

Leu Ser Val Asp Asp Tyr Arg Asp Phe Lys Asp Phe Leu Asn Arg Lys
1               5                   10                  15

Ile Cys Ile Ala Val Gly Ala Met Ala Ser Gly Arg Asn Val Ile Phe
                20                  25                  30

Tyr Val Ala Lys Gly Ala Lys Pro Ile Ser Ala Glu Phe Ala Met Ile
            35                  40                  45

Lys Leu Glu Gly Ile Val Leu Asn Val Phe Thr Gln Gln Gly Gly Gln
    50                  55                  60

Asn Lys Lys Gly Glu Ser Phe Asp Asp Arg Asp Lys Val Gln Ile Leu
65              70                  75                  80

Gly Ala Met Asp Leu Pro Asn Gly Asp Val Lys Asn Glu Leu Phe Thr
                85                  90                  95

<210> SEQ ID NO 36
<211> LENGTH: 232
<212> TYPE: PRT
<213> ORGANISM: artificial sequences
<220> FEATURE:
<221> NAME/KEY: SOURCE
<222> LOCATION: 1..232
<223> OTHER INFORMATION: /mol_type="protein"
      /note="Sphinx 2.36.232"
      /organism="artificial sequences"

<400> SEQUENCE: 36

Met Gln Glu Gln Tyr Leu Trp Thr Gln Val Asp Phe Lys Val Gly Ser
1               5                   10                  15

Glu Thr Ser Ile Lys Ala Leu Lys Ala Ala Thr Lys Leu Lys Gly Cys
                20                  25                  30

Gly Gln Phe Leu Leu Phe Arg Asn Tyr Tyr Thr Ile Asp Gln Ile Lys
            35                  40                  45

Leu Glu Lys Phe His Val Cys Gly Gln His Leu Leu Cys Pro Met Cys
    50                  55                  60

Ala Gly Ile Arg Ala Ala Arg Ser Met Asn Arg Tyr Ile Gln Arg Ile
65              70                  75                  80

Glu Glu Ile Met Arg Gln Asn Arg Lys Leu Lys Pro Val Leu Ile Thr
                85                  90                  95

Leu Thr Val Lys Asn Gly Glu Asp Leu Gln Glu Arg Phe Glu His Leu
                100                 105                 110

Thr Gly Ser Phe Lys Thr Leu Leu Gln Arg Tyr Arg Asp Phe Lys Lys
            115                 120                 125

Lys Gly Arg Gly Phe Asn Gln Phe Cys Lys Ile Asp Gly Gly Phe Tyr
    130                 135                 140

Thr Thr Glu Tyr Thr Tyr His Gly Tyr Ala Lys Ala Val Ala Glu Val
145             150                 155                 160

Cys Lys Tyr Ala Leu Lys Phe Ser Asp Leu Ser Thr Glu Lys Thr Phe
                165                 170                 175

Gln Ala Phe Phe Asp Pro Asn Glu Thr Thr Gln Gln Trp His Pro His
            180                 185                 190

Ile His Ile Phe Ala Leu Val Thr Asp Arg Ile Asp Gln Glu Glu Leu
    195                 200                 205

Ala Glu Thr Trp His Asp Ile Thr Leu Asp Ser Tyr Ile Val Asp Ile
210                 215                 220

Arg Arg Val Lys Lys Thr Lys Glu
225                 230

<210> SEQ ID NO 37
<211> LENGTH: 137
<212> TYPE: PRT
<213> ORGANISM: artificial sequences
<220> FEATURE:
<221> NAME/KEY: SOURCE
<222> LOCATION: 1..137
<223> OTHER INFORMATION: /mol_type="protein"
    /note="HCBI2.170.96.PEP"
    /organism="artificial sequences"

<400> SEQUENCE: 37

```
Met Val Leu Phe Tyr Ser Thr Glu Tyr Thr Tyr Asn Ser Lys Thr Lys
1               5                   10                  15

Glu Trp His Pro His Ile His Ile Phe Ala Leu Leu Asn Glu Trp Ile
            20                  25                  30

Asp Gln Glu Glu Leu Ala Glu Thr Trp His Asp Ile Thr Leu Asp Ser
        35                  40                  45

Tyr Ile Val Asp Ile Arg Arg Val Lys Arg Thr Lys Glu Glu Lys Leu
    50                  55                  60

Thr Asp Asp Leu Pro Leu Asp Asp Leu Pro Tyr Met Glu Leu Leu Tyr
65                  70                  75                  80

Arg Phe Val Phe Gly Lys Lys His Gly Tyr Ser Lys Ala Val Ala Glu
                85                  90                  95

Val Cys Lys Tyr Ala Leu Lys Phe Ser Asp Leu Ser Leu Glu Asn Thr
            100                 105                 110

Trp Glu Ala Tyr Leu Ser Leu Lys Gly Asn Arg Leu Thr Gly Cys Phe
        115                 120                 125

Gly Ser Met Tyr Gly Val Lys Leu Pro
    130                 135
```

<210> SEQ ID NO 38
<211> LENGTH: 104
<212> TYPE: DNA
<213> ORGANISM: artificial sequences
<220> FEATURE:
<221> NAME/KEY: source
<222> LOCATION: 1..104
<223> OTHER INFORMATION: /mol_type="DNA"
    /note="BlastN2 Query12"
    /organism="artificial sequences"

<400> SEQUENCE: 38
gatcaacaca gggatagaat atcacgtttt ggacttttga aacagcccat aattcggaca    60
ctttggcggg tgatgaatta caggctttgc aatctgctaa ggca                   104

<210> SEQ ID NO 39
<211> LENGTH: 104
<212> TYPE: DNA
<213> ORGANISM: artificial sequences
<220> FEATURE:
<221> NAME/KEY: source
<222> LOCATION: 1..104
<223> OTHER INFORMATION: /mol_type="DNA"
    /note="BlastN2 Subject1212"
    /organism="artificial sequences"

<400> SEQUENCE: 39
gatcaacaca gggatagaat atcacgtttt ggacttttga aacagcccat aattctgatg    60
ctttggcggg cgacgaatta caggctttgc aatctgctaa tgca                   104

<210> SEQ ID NO 40

```
<211> LENGTH: 424
<212> TYPE: DNA
<213> ORGANISM: artificial sequences
<220> FEATURE:
<221> NAME/KEY: source
<222> LOCATION: 1..424
<223> OTHER INFORMATION: /mol_type="DNA"
      /note="lastN2 Query13"
      /organism="artificial sequences"

<400> SEQUENCE: 40
caagaacaat atttgtggac gcaggttgat ttcaaatccg aaggtgaaaa tgagacatcc    60 ataaggctc ttaaggctgc aaccaaatta aagggatgcg gtcaatttt gctattccat    120 aactactaca caattgacca agttaaactt gctaaggccc attattgttc tcagcatttg    180
ctttgcccta tgtgtgctgg tgtaagggct gctaagtcaa tgagtagata tgttcaacgt    240
attgaagaat tgatgcgtca gaatcgcaaa ttaaagcccg tattgatcac tttaacggtt    300
gatggttaga tcgttataac gattacaaaa agaaaggtcg tggttttaat caattctgca    360
agattaagaa tggggaagac ctagaagaac gctttaaaca cttagacgct catttaggac    420
gctt                                                                 424

<210> SEQ ID NO 41
<211> LENGTH: 419
<212> TYPE: DNA
<213> ORGANISM: artificial sequences
<220> FEATURE:
<221> NAME/KEY: source
<222> LOCATION: 1..419
<223> OTHER INFORMATION: /mol_type="DNA"
      /note="BlastN2 Subject13"
      /organism="artificial sequences"

<400> SEQUENCE: 41
caagaacaat atttgtggac tcaggttgat ttcaaggttg gaagtgaaac atctatcaaa    60
gctcttaagg ctgcaaccaa attaaaggga tgcggtcaat ttctgctttt tcgtaattac    120
tacaccatag atcaaatcaa gctcgaaaaa ttccacgtat gcggacagca tttgctatgt    180
ccaatgtgtg ctggtattcg tgctgcccgt tcaatgaatc ggtatattca acgcatcgaa    240
gaaataatgc gtcagaatcg caagctaaag cccgtattga tcactttgac cgttaagaac    300
ggtgaagacc tacaggaacg cttttgaacac ctcacaggct catttaagac gcttgatggt    360
tacagcgtta ccgtgatttt aagaaaaagg gtcgagggtt taatcaattt tgcaaaatt    419

<210> SEQ ID NO 42
<211> LENGTH: 51
<212> TYPE: DNA
<213> ORGANISM: artificial sequences
<220> FEATURE:
<221> NAME/KEY: source
<222> LOCATION: 1..51
<223> OTHER INFORMATION: /mol_type="DNA"
      /note="BlastN2 Query14"
      /organism="artificial sequences"

<400> SEQUENCE: 42
cagtgagtta gccttggctt ctcgctgttt tttctttctc ttgatactat t              51

<210> SEQ ID NO 43
<211> LENGTH: 51
<212> TYPE: DNA
<213> ORGANISM: artificial sequences
<220> FEATURE:
<221> NAME/KEY: source
```

-continued

```
<222> LOCATION: 1..51
<223> OTHER INFORMATION: /mol_type="DNA"
      /note="BlastN2 Subject14"
      /organism="artificial sequences"

<400> SEQUENCE: 43
cagtgagtta ggcttgccga ctcgctgttt tttcttttac ttgatactat t          51

<210> SEQ ID NO 44
<211> LENGTH: 91
<212> TYPE: DNA
<213> ORGANISM: artificial sequences
<220> FEATURE:
<221> NAME/KEY: source
<222> LOCATION: 1..91
<223> OTHER INFORMATION: /mol_type="DNA"
      /note="BlastN2 Query15"
      /organism="artificial sequences"

<400> SEQUENCE: 44
gaatatcacg ttttggactt ttgaaacata gctttggcgg gtgatgaatt acaggctttg    60
caatctgcta aggcagatca acacagggat a                                  91

<210> SEQ ID NO 45
<211> LENGTH: 91
<212> TYPE: DNA
<213> ORGANISM: artificial sequences
<220> FEATURE:
<221> NAME/KEY: source
<222> LOCATION: 1..91
<223> OTHER INFORMATION: /mol_type="DNA"
      /note="BlastN2 Subject15"
      /organism="artificial sequences"

<400> SEQUENCE: 45
gaataacacg ttttgcgact ttgaaacata gctttggcgg gcggagaaat acaggctttg    60
caatctgcaa acgcagatca acacagggat a                                  91

<210> SEQ ID NO 46
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="BlastN2 Query16"
      /organism="artificial sequences"

<400> SEQUENCE: 46 ctgtttttc tttctcttga tactattgat taa                                 33

<210> SEQ ID NO 47
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="BlastN2 Subject16"
      /organism="artificial sequences"

<400> SEQUENCE: 47 ctgtttttc ttttacttga tactattgat taa                                 33

<210> SEQ ID NO 48
```

```
<211> LENGTH: 60
<212> TYPE: DNA
<213> ORGANISM: artificial sequences
<220> FEATURE:
<221> NAME/KEY: source
<222> LOCATION: 1..60
<223> OTHER INFORMATION: /mol_type="DNA"
      /note="BlastN2 Query17"
      /organism="artificial sequences"

<400> SEQUENCE: 48
agatcaacac agggatagaa tatcacgttt tggacttttg aaacatagag cgaagctaca    60

<210> SEQ ID NO 49
<211> LENGTH: 60
<212> TYPE: DNA
<213> ORGANISM: artificial sequences
<220> FEATURE:
<221> NAME/KEY: source
<222> LOCATION: 1..60
<223> OTHER INFORMATION: /mol_type="DNA"
      /note="BlastN2 Subject17"
      /organism="artificial sequences"

<400> SEQUENCE: 49
agatcaacat agggatagaa taacacgttt tggcattttg aaacatagat cgaagcaaca    60

<210> SEQ ID NO 50
<211> LENGTH: 49
<212> TYPE: DNA
<213> ORGANISM: artificial sequences
<220> FEATURE:
<221> NAME/KEY: source
<222> LOCATION: 1..49
<223> OTHER INFORMATION: /mol_type="DNA"
      /note="BlastN2 Query18"
      /organism="artificial sequences"

<400> SEQUENCE: 50
ttaaagcccg tattgatcac tttaacggtt aagaatgggg aagacctag                49

<210> SEQ ID NO 51
<211> LENGTH: 49
<212> TYPE: DNA
<213> ORGANISM: artificial sequences
<220> FEATURE:
<221> NAME/KEY: source
<222> LOCATION: 1..49
<223> OTHER INFORMATION: /mol_type="DNA"
      /note="BlastN2 Subject18"
      /organism="artificial sequences"

<400> SEQUENCE: 51
ttaaagcccg ttatgatcac gtttacggtt aaaaatgggg tagacctag                49

<210> SEQ ID NO 52
<211> LENGTH: 923
<212> TYPE: DNA
<213> ORGANISM: artificial sequences
<220> FEATURE:
<221> NAME/KEY: source
<222> LOCATION: 1..923
<223> OTHER INFORMATION: /mol_type="DNA"
      /note="HQ444405"
      /organism="artificial sequences"

<400> SEQUENCE: 52
tagatctaaa catgcaagaa caatatttgt ggactcaggt tgatttcaag gttggaagtg    60
aaacatctat caaagctctt aaggctgcaa ccaaattaaa gggatgcggt caatttctgc   120
```

```
tttttcgtaa ttactacacc atagatcaaa tcaagctcga aaaattccac gtatgcggac      180
agcatttgct atgtccaatg tgtgctggta ttcgtgctgc ccgttcaatg aatcggtata      240
ttcaacgcat cgaagaaata atgcgtcaga atcgcaagct aaagcccgta ttgatcactt      300
tgaccgttaa gaacggtgaa gacctacagg aacgctttga acacctcaca ggctcattta      360
agacgctttt acagcgttac cgtgtaagga cgtaaagccg aacaaaagga atgaggaaag      420
atgaacgagg agcttcgacg aggcacgacc gaatacacct acaacgaaac aacccaacaa      480
tggcatccgc atattcatat ttttgcgtta gtgactgacc ggattgacca ggaggaacta      540
gcagaaactt ggcacgatat aacgcttgat tcatacattg tggacatccg cagggtcaaa      600
aaaactaaag aacacggata tgcaaaggct gttgccgaag tctgcaaata cgctcttaag      660
tttagcgatc tatccactga gaaaaccttt caagcatttt ttgacccctta agggcaaaag     720 gcttacaggt tcattcggct ctatgcatgg tgtaaaaatt cctgaaagcg acccgatga      780 aatgcctaaa gaggaacttc catatcttga gctgctctat cgtttcgttt ttggtgaaag      840
gtcttattac aacctagagt taacatttta agaaaaaggg tcgagggttt aatcaatttt      900
gcaaaattga tggcggtttt tat                                              923
```

```
<210> SEQ ID NO 53
<211> LENGTH: 899
<212> TYPE: DNA
<213> ORGANISM: artificial sequences
<220> FEATURE:
<221> NAME/KEY: source
<222> LOCATION: 1..899
<223> OTHER INFORMATION: /mol_type="DNA"
    /note="CU459139"
    /organism="artificial sequences"

<400> SEQUENCE: 53
```

```
cgttagctaa gattaaagaa aattatcatg ccgatgtaaa aaacgatgaa tctattcgcg       60
ccatgaaaac tgcccaaaaa ttaaatgggt gcggtaattt tcttctattc aaaaattttt      120
acaccattaa tcaaattaaa ctcgccaagt tccaagcttg tagtgagcat ttgttatgtc      180
cgttttgtgc tggtattaga gcttctaagg caattcaaaa atactctgag cgtgttgatc      240
aagtcttatc tgaaaatcct cgtttaaagc ccgttatgat cacgtttacg gttaaaaatg      300
gggtagacct aggggaacgg ttcacccatc ttataaaatc gtttagaacg cttatagagc      360
gtcgtaggga ctatattaaa aaagggcgtg gctttaatga attttgcaaa attaatggtg      420
cgatgtattc atatgagaat acttacaatg aaaaaactaa tgaatggcat cctcatattc      480
atatgtttgc acttttggat gattggatag atcaggatga attgtctcaa tattggcaat      540
ccattactgg ggactctatg gtcgttgata ttcgtagagc caaaaaacaa aaagacttag      600
gctattcagg tgctgctgct gaagtctgta aatatgctct caaatttggt gatctttctg      660
tagaaaagac ttgggaagct ttcaaagttt tgaaaggtaa gcgattaagt ggggcttttg      720
gatctctttg gggcgtgaaa attcctgaat cattgataga tgatcttcca gacgattctt      780
tacaacttac tcgtcatgtc gaacctacag gtaaggacga cgccgacgag cttcgaggag      840 atttaccttta tttagaaatg atttataagt tcgtcttttc taagaagtct tattacgat      899
```

```
<210> SEQ ID NO 54
<211> LENGTH: 418
<212> TYPE: DNA
<213> ORGANISM: artificial sequences
<220> FEATURE:
```

```
<221> NAME/KEY: source
<222> LOCATION: 1..418
<223> OTHER INFORMATION: /mol_type="DNA"
      /note="444405"
      /organism="artificial sequences"

<400> SEQUENCE: 54
gcggatctct atgcttcagg aaaaatgaaa tcaggagatc agtcagatga ttaatttaca    60
agggacactt ataaatgctt ttcgtcttga tggtggtaaa gggaaagacg gcaaagaata   120
tgaagcacgt gacaaggtgc aaattcttgg ttcgctggag ttgcccaacg gtgagatcaa   180
acatgagctt gttgacttaa cggttgaaga tgctcgcatc tttgagccat tcaaacacaa   240
ggtaattagc atttcatgcg gtgctatggc tatcggtcga aatgttgttt tttatgttcg   300
ttaggcttgc cgactcgctg tttttttcttt tacttgatac tattaactaa agtggggaca   360
aaaaggtgca aagcctgttt tagcagatgt aatgtaattc atgaaaaaaa acagtgag     418

<210> SEQ ID NO 55
<211> LENGTH: 1086
<212> TYPE: DNA
<213> ORGANISM: artificial sequences
<220> FEATURE:
<221> NAME/KEY: source
<222> LOCATION: 1..1086
<223> OTHER INFORMATION: /mol_type="DNA"
      /note="3.108"
      /organism="artificial sequences"

<400> SEQUENCE: 55
gcgagtgtct acgagcgaag ttatgaaagt tcgattcttc cccctctga aaaccgctt      60 ttaaaaatat tggctgctag atggttttta ctatcgtgag cttttgcttt taaaaaaaca   120
cgagcgaagc gagttcatag ttgcttttgg gggtttcggg gggcttgccc cctgaacaag   180
atcacggagt gggaatttat cacggtagtg aaaaagtacc ctctgtgtat ccttgcttat   240
ttctttttaa acctttgaac ttttttcccgt aatttgaaga aattgcccct cgactaagct   300
tgcttagtca aaaaagtttg agcaaagcga aaacataggg caattttcat gatgaaaatg   360
ggcttttaag gcttttaaat gcttttaagg cttttagaca tgctgaaacg caagcctagc   420
aaggcataca gagggcattt aacaccgttt acctaccaat accccaccgt ttacctacca   480 atacccacc gttacctac caataccca ccgtttacct accttaatac acaataatat     540
ttttatgtgg tataacgtaa taaaatatat aggtggttta tgagtgattt aatagtaaaa   600
gataacgccc taatgaacgc tagttataac ttagacttgg ttgaacagcg gttaattctt   660
ttagctatcc ttgaagctag agaatcaggc aaaggaatta acgcaaatga ccctcttaca   720
gtccatgcag agagttatat caatcaattt ggtgtagcta gacagactgc ttatcaagcc   780
ctaaaagatg cctgcaaaga tttatttgcc cgtcaattca gctatcaaga aaagcgtgaa   840
cgtggacgag ctaatattac aagtcgttgg gtcagccaaa ttgcttacat tgatgaaact   900
gcaacggttg aggttatttt cgcccctgcg gttgttccac tgatcacaag gttagaggaa   960
caattctcga agtacgatat tgaacaaatt agtagtctat cgagtgccta tgcagttcgc  1020
ttatatgagt tattgatctg ctggagaaca acaggaaaga caccagttat tgacttaaca  1080
gaattc                                                             1086

<210> SEQ ID NO 56
<211> LENGTH: 324
<212> TYPE: PRT
<213> ORGANISM: artificial sequences
```

```
<220> FEATURE:
<221> NAME/KEY: SOURCE
<222> LOCATION: 1..324
<223> OTHER INFORMATION: /mol_type="protein"
      /note="Sphinx1.76.324.PEP"
      /organism="artificial sequences"

<400> SEQUENCE: 56
```

| | | | | | | | | | | | | | | | |
|---|---|---|---|---|---|---|---|---|---|---|---|---|---|---|---|
| Gln | Ser | Glu | Ile | Ile | Thr | Asp | Ala | Ile | Ala | Asp | Gln | Trp | Glu | Ser | Lys |
| 1 | | | | 5 | | | | | 10 | | | | | 15 | |
| Leu | Glu | Glu | Phe | Gly | Val | Val | Phe | Gly | Ser | Tyr | Ile | Asn | Gln | Phe | Asn |
| | | | 20 | | | | | 25 | | | | | 30 | | |
| Val | Gln | Arg | His | Thr | Ala | Tyr | Gln | Ala | Leu | Lys | Asp | Ala | Cys | Lys | Asp |
| | | 35 | | | | | 40 | | | | | 45 | | | |
| Leu | Phe | Ala | Arg | Gln | Phe | Ser | Tyr | Gln | Glu | Lys | Arg | Glu | Arg | Gly | Arg |
| | 50 | | | | | 55 | | | | | 60 | | | | |
| Ile | Asn | Ile | Thr | Ser | Arg | Trp | Val | Ser | Gln | Ile | Gly | Tyr | Met | Asp | Asp |
| 65 | | | | | 70 | | | | | 75 | | | | | 80 |
| Thr | Ala | Thr | Val | Glu | Ile | Ile | Phe | Ala | Pro | Ala | Val | Val | Pro | Leu | Ile |
| | | | | 85 | | | | | 90 | | | | | 95 | |
| Thr | Arg | Leu | Glu | Glu | Gln | Phe | Thr | Gln | Tyr | Asp | Ile | Glu | Gln | Ile | Ser |
| | | | 100 | | | | | 105 | | | | | 110 | | |
| Gly | Leu | Ser | Ser | Ala | Tyr | Ala | Val | Arg | Met | Tyr | Glu | Leu | Leu | Ile | Cys |
| | | 115 | | | | | 120 | | | | | 125 | | | |
| Trp | Arg | Ser | Thr | Gly | Lys | Thr | Pro | Ile | Ile | Glu | Leu | Asp | Glu | Phe | Arg |
| | 130 | | | | | 135 | | | | | 140 | | | | |
| Lys | Arg | Ile | Gly | Val | Leu | Asp | Thr | Glu | Tyr | Thr | Arg | Thr | Asp | Asn | Leu |
| 145 | | | | | 150 | | | | | 155 | | | | | 160 |
| Lys | Met | Gln | Val | Ile | Glu | Leu | Ala | Leu | Lys | Gln | Ile | Asn | Glu | His | Thr |
| | | | | 165 | | | | | 170 | | | | | 175 | |
| Asp | Ile | Thr | Ala | Ser | Tyr | Glu | Gln | His | Lys | Lys | Gly | Arg | Val | Ile | Thr |
| | | | 180 | | | | | 185 | | | | | 190 | | |
| Gly | Phe | Ser | Phe | Met | Phe | Lys | His | Lys | Lys | Gln | Asn | Ser | Asp | Lys | Thr |
| | | 195 | | | | | 200 | | | | | 205 | | | |
| Pro | Asp | Thr | Asn | Ala | Ser | Ser | Pro | Arg | Ile | Val | Lys | His | Ser | Gln | Ile |
| | 210 | | | | | 215 | | | | | 220 | | | | |
| Pro | Thr | Asn | Ile | Val | Lys | Gln | Pro | Glu | Asn | Ala | Lys | Met | Ser | Asp | Leu |
| 225 | | | | | 230 | | | | | 235 | | | | | 240 |
| Glu | His | Arg | Ala | Ser | Arg | Val | Thr | Gly | Glu | Ile | Met | Arg | Asn | Arg | Leu |
| | | | | 245 | | | | | 250 | | | | | 255 | |
| Ser | Asp | Arg | Phe | Lys | Gln | Gly | Asp | Glu | Ser | Ala | Ile | Asp | Met | Met | Lys |
| | | | 260 | | | | | 265 | | | | | 270 | | |
| Arg | Ile | Met | Ser | Asp | Leu | Ile | Val | Lys | Asp | Asn | Ala | Leu | Met | Asn | Ala |
| | | 275 | | | | | 280 | | | | | 285 | | | |
| Ser | Tyr | Asn | Leu | Ala | Leu | Val | Glu | Gln | Arg | Leu | Ile | Leu | Leu | Ala | Ile |
| | 290 | | | | | 295 | | | | | 300 | | | | |
| Ile | Glu | Ala | Arg | Glu | Thr | Gly | Lys | Gly | Ile | Asn | Ala | Asn | Asp | Pro | Leu |
| 305 | | | | | 310 | | | | | 315 | | | | | 320 |
| Thr | Val | His | Ala | | | | | | | | | | | | |

```
<210> SEQ ID NO 57
<211> LENGTH: 201
<212> TYPE: PRT
<213> ORGANISM: artificial sequences
<220> FEATURE:
<221> NAME/KEY: SOURCE
<222> LOCATION: 1..201
```

<223> OTHER INFORMATION: /mol_type="protein"
        /note="HCBI3.108.201.PEP"
        /organism="artificial sequences"

<400> SEQUENCE: 57

```
Met Ser Asp Leu Ile Val Lys Asp Asn Ala Leu Met Asn Ala Ser Tyr
1               5                   10                  15

Asn Leu Asp Leu Val Glu Gln Arg Leu Ile Leu Leu Ala Ile Leu Glu
            20                  25                  30

Ala Arg Glu Ser Gly Lys Gly Ile Asn Ala Asn Asp Pro Leu Thr Val
        35                  40                  45

His Ala Ile Leu Pro Pro Ser Glu Lys Pro Leu Leu Lys Ile Leu Ala
    50                  55                  60

Ala Arg Trp Phe Leu Leu Ser Ile Ala Tyr Ile Asp Glu Thr Ala Thr
65                  70                  75                  80

Val Glu Val Ile Phe Ala Pro Ala Val Pro Leu Ile Thr Arg Leu
                85                  90                  95

Glu Glu Gln Phe Ser Lys Tyr Asp Ile Glu Gln Ile Ser Ser Leu Ser
            100                 105                 110

Ser Ala Tyr Ala Val Arg Leu Tyr Glu Leu Leu Ile Cys Trp Arg Thr
        115                 120                 125

Thr Gly Lys Thr Pro Val Ile Asp Leu Thr Glu Phe Ala Ser Val Tyr
    130                 135                 140

Glu Arg Ser Tyr Glu Ser Ser Glu Ser Tyr Ile Asn Gln Phe Gly Val
145                 150                 155                 160

Ala Arg Gln Thr Ala Tyr Gln Ala Leu Lys Asp Ala Cys Lys Asp Leu
                165                 170                 175

Phe Ala Arg Gln Phe Ser Tyr Gln Glu Lys Arg Glu Arg Gly Arg Ala
            180                 185                 190

Asn Ile Thr Ser Arg Trp Val Ser Gln
        195                 200
```

<210> SEQ ID NO 58
<211> LENGTH: 442
<212> TYPE: DNA
<213> ORGANISM: artificial sequences
<220> FEATURE:
<221> NAME/KEY: source
<222> LOCATION: 1..442
<223> OTHER INFORMATION: /mol_type="DNA"
        /note="BlastN2Query19"
        /organism="artificial sequences"

<400> SEQUENCE: 58

```
ttatgagtga tttaatagta aaagataacg ccctaatgaa cgctagttat aacttagact    60
tggttgaaca gcggttaatt cttttagcta tccttgaagc tagagaatca ggcaaaggaa   120
ttaacgcaaa tgaccctctt acagtccatg cagagagtta tatcaatcaa tttggtgtag   180
tatcgagtgc ctatgcagtt cgctagacag actgcttatc aagccctaaa agatgcctgc   240
aaagatttat ttgcccgtca attcagctat caagaaaagc gtgaacgtgg acgagctaat   300
attacaagtc gttgggtcag ccaaattgct tacattgatg aaactgcaac ggttgaggtt   360
attttcgccc ctgcggttgt tccactgatc acaaggttag aggaacaatt ctcgaagtac   420
gatattgaac aaattagtag tc                                            442
```

<210> SEQ ID NO 59
<211> LENGTH: 442
<212> TYPE: DNA

```
<213> ORGANISM: artificial sequences
<220> FEATURE:
<221> NAME/KEY: source
<222> LOCATION: 1..442
<223> OTHER INFORMATION: /mol_type="DNA"
      /note="BlastN2 Subject19"
      /organism="artificial sequences"

<400> SEQUENCE: 59
tatcgagtgc atatgctgtt cgtggttgaa cagaggttaa ttctattagc aatcatagaa      60
gcgagagaaa caggcaaagg gattaatgcc aatgatcctc ttacggttca tgcaggtagc     120
tatatcaatc aatttaacgt acaaaggcat acggcatatc aagccctcaa agatgcttgt     180
aaagacttgt ttgcccgtca attcagttac caagaaaagc gagaacgagg acgaattaat     240
attacaagtc gatgggtttc gcaaattggc tatatggacg atacagcaac cgttgagatt     300
atttttgccc ctgcggttgt tcctctgatt acacggctag aggaacagtt cacccagtac     360
gatattgagc aaattagcgg ttttatgagc gatttaatag taaaagataa cgccctaatg     420
aatgctagtt ataacttagc tt                                              442

<210> SEQ ID NO 60
<211> LENGTH: 132
<212> TYPE: DNA
<213> ORGANISM: artificial sequences
<220> FEATURE:
<221> NAME/KEY: source
<222> LOCATION: 1..132
<223> OTHER INFORMATION: /mol_type="DNA"
      /note="BlastN2 Query20"
      /organism="artificial sequences"

<400> SEQUENCE: 60
tttgaagaaa ttgcccctcg actaagcttg cttagtcaaa aaagtttgag caaagcgaaa      60
acatagggca atttccatga tgaaaatggg ctttttaaggc ttttaaatgc ttttaaggct    120
tttagacatg ct                                                         132

<210> SEQ ID NO 61
<211> LENGTH: 130
<212> TYPE: DNA
<213> ORGANISM: artificial sequences
<220> FEATURE:
<221> NAME/KEY: source
<222> LOCATION: 1..130
<223> OTHER INFORMATION: /mol_type="DNA"
      /note="BlastN2 Subject20"
      /organism="artificial sequences"

<400> SEQUENCE: 61
tttgcagaaa ttgcccctcg aagcttgctt agtcaaaaaa gtttgagcaa agcgaaattt      60
agacatgcts acatagggca attttcatga agaaattggg cttttaaagt ttttaaatgt    120
tttaaatgct                                                            130

<210> SEQ ID NO 62
<211> LENGTH: 149
<212> TYPE: DNA
<213> ORGANISM: artificial sequences
<220> FEATURE:
<221> NAME/KEY: source
<222> LOCATION: 1..149
<223> OTHER INFORMATION: /mol_type="DNA"
      /note="BlastN2 Query21"
      /organism="artificial sequences"

<400> SEQUENCE: 62
```

```
cgagcgaagc gagttcatag ttgcttttgt taaaaatatt ggctgctaga tggttttttac    60 tatcgtgagc ttttgctttt nnnnnnncag cgagtgtcta cgagcgaagt tatgaaagtt   120
cgattcttcc ccctctgaa aaaccgctt                                      149
```

<210> SEQ ID NO 63
<211> LENGTH: 148
<212> TYPE: DNA
<213> ORGANISM: artificial sequences
<220> FEATURE:
<221> NAME/KEY: source
<222> LOCATION: 1..148
<223> OTHER INFORMATION: /mol_type="DNA"
      /note="BlastN2 Subject21"
      /organism="artificial sequences"

<400> SEQUENCE: 63

```
gcgagtgtct acgagcgact caatgaaagt tcgattattc ccctctgga aaaccgcttc     60 gagcaaagcg agttcatagt tgcttttgtt aaaaatattg ctgctagat ggttttact    120 atagtgaggt tttgctttta aaaaaaca                                      148
```

<210> SEQ ID NO 64
<211> LENGTH: 162
<212> TYPE: DNA
<213> ORGANISM: artificial sequences
<220> FEATURE:
<221> NAME/KEY: source
<222> LOCATION: 1..162
<223> OTHER INFORMATION: /mol_type="DNA"
      /note="BlastN2 Query22"
      /organism="artificial sequences"

<400> SEQUENCE: 64

```
tttagacatg ctgaaacgca agcctagcaa ggcatacaga ggacataggg caattttcat    60
gatgaaaatg ggcttttaag gcttttaaat gcttttaagg cttttgaaga aattgcccct   120
cgactaagct tgcttagtca aaaagtttg agcaaagcga aa                       162
```

<210> SEQ ID NO 65
<211> LENGTH: 162
<212> TYPE: DNA
<213> ORGANISM: artificial sequences
<220> FEATURE:
<221> NAME/KEY: source
<222> LOCATION: 1..162
<223> OTHER INFORMATION: /mol_type="DNA"
      /note="BlastN2 Subject22"
      /organism="artificial sequences"

<400> SEQUENCE: 65

```
tttgcagaaa ttgcccctcg actaagcttg cttagtcaaa aagtttgag caaagcgaaa     60 acatagggca attttcgtga tgaaaatggg cttttaatgt ttttaaatgc ttttaatgct   120
tttagacatg ctgaaacgca agcctagcaa ggcatacaga gg                      162
```

<210> SEQ ID NO 66
<211> LENGTH: 149
<212> TYPE: DNA
<213> ORGANISM: artificial sequences
<220> FEATURE:
<221> NAME/KEY: source
<222> LOCATION: 1..149
<223> OTHER INFORMATION: /mol_type="DNA"
      /note="BlastN2 Query23"
      /organism="artificial sequences"

<400> SEQUENCE: 66
cgagcgaagc gagttcatag ttgcttttgt taaaaatatt ggctgctaga tggtttttac    60
tatcgtgagc ttttgctttt nnnnnnncag cgagtgtcta cgagcgaagt tatgaaagtt   120
cgattcttcc cccctctgaa aaaccgctt                                      149

<210> SEQ ID NO 67
<211> LENGTH: 148
<212> TYPE: DNA
<213> ORGANISM: artificial sequences
<220> FEATURE:
<221> NAME/KEY: source
<222> LOCATION: 1..148
<223> OTHER INFORMATION: /mol_type="DNA"
      /note="BlastN2 Subject23"
      /organism="artificial sequences"

<400> SEQUENCE: 67
cgagcaaagc gagttcatag ttgcttttgt taaaaatatt ggctgctaga tggtttttac    60
tatagtgagg ttttgctttt aaaaaaacag cgagtgtcta cgagcgactc aatgaaagtt   120
cgattattcc ccctctggaa aaccgctt                                       148

<210> SEQ ID NO 68
<211> LENGTH: 2958
<212> TYPE: DNA
<213> ORGANISM: artificial sequences
<220> FEATURE:
<221> NAME/KEY: source
<222> LOCATION: 1..2958
<223> OTHER INFORMATION: /mol_type="DNA"
      /note="HCBI4.296"
      /organism="artificial sequences"

<400> SEQUENCE: 68
ctgagaagcg aagaaaagat gcggttttgt gtattgaaca tcttgtgact gcatcaccag    60
aatgggacgg ctggggaact gaaaagaaa ctgcattttt tgaacagtca aggaaatggc   120
ttgaaagcaa atatggtaaa aaaaatgtgg tcagtacaac gattcataga gatgaaacaa   180
ctccacattt agttgcgtat gttgttcccg ttgacgaaga aacgggacgt ttaaatgcta   240
aaaaatttat tggtggatct cgacatacac tttcacagat gcagactgat tttgcagttg   300
aagtaaagga tttaggatta gatcgcgggg tacaggggag caaagcaaaa catacgtcta   360
ttcaagaata ttatgaaaaa ttgaacaatt atgagaatga accaggtatt gaaaaaggac   420
tcacctatga agtgcctgaa cctgagtttt tgaatctaa aaatgtttac ggtgagagag   480
tcgcagaagc tgtggctgct cagataattg atcaaattgc acctcgattc gacaatgcta   540
atttattggc tagtcaaaca aaaaaattaa aaaaagaact gttaaacact agaaaaacgc   600
ttgatgaagt acagaaacga gcaaaaccct atttggatat aatcaacgaa tataatcatc   660
caaatcttga gaaagaattt aataagcaag ttgctaaatt aaaagataat tttgattcag   720
cacttgagca tcatagattc ctaaaaagac aggaagaaca agaaagattt aaccaacaac   780
gtgaacttcg caatcaatta cacttagagc aagagcaaaa aaaacaactg gttgagcaag   840
aaaggcaaga aaaagaacgt ttagcacttt taagacgtca agaattagaa atcagcgga   900 aaaatgagcc taaaaaacct gataatggca ataataacga ctactcaccc tcataatacc   960
cgtttaaacg caaaaaaaac gggggtttta gccctgtttg gccttttatg cataaaagta  1020
taattgaaat aaaaaaaatgc tcttagaacg caaatgatga gcatttagcg agtgtctacg  1080
agcgacacaa tgaaaattcg cctattcccc ctctgaaaaa ctgcttttgc tctttttgc   1140

```
ttctggagag acttgttagc gagtgtctac gagcgaagta ttgatgcttt tgctcttaaa    1200
aaagcatgag catagcgaat gcattatcta tgcttttgac tttgattttg ctcttgaaac    1260
gacacgagca acgcgagtgc catagccttt gattttgcct tttttgggct tttaatgttt    1320
ttaaatgctt ttaaatgctt ttagatagcc tgaaagcatt gctatacata tgtttcagag    1380
cttataaaga tacagattcc ttgctataaa gatacagatt ccttgctata aagatacaga    1440
ttccttgcta taaagataca gattccttgc attaaggtac atagtcatat aatgtatctt    1500
ttaatacatg attgtatgaa ataactaata tgaaaatgg gttagtagtg aaagataatg     1560
cgttaatgaa tgccagctat aatttagaag taacagaaca gcgcttaata cttctagcaa    1620
tcattagtgc aagagaaaca gggcaaggga ttacgtcaga tagcaaatta gaaatacatg    1680
ctagtgacta tgcaattcag ttcagtgttg caaaagaaac agcttatgag gcactaaaaa    1740
gtgctgtaaa taatttattt gagcgtcaat tttcatttag agaagaaaca aaaaaaggca    1800
ctggcattgt acggtcacga tgggttagca gaattaaata cattgatgac gcagcaatac    1860
ttgaaatcac ttttgcgcct gacgttgtac cattaatcac tagacttgaa gaacacttca    1920
caagttatca aatcaagcaa atagcacagc ttacaagtaa gtacgctatc cgtttatatg    1980
aacttcttat tgcttggcga actacaggca aagtccctga gcttgaacta tcagaattta    2040
gaaatagatt aggcatagct agtaatgaat acacagcaat gaacaacttt aaaagccgtg    2100
tattagagcc gtctattaag cagatcaatg aacacacaga cattactgtg acgtatgaac    2160
agcataaaaa agggcggaca attacaggct tttcattcag atttaagcag aagcaacaag    2220
caaaaaaaat agaaactaac agagatccaa acacacctga cttttttatc aaaatgaccg    2280
atgctcaacg gcatttattc gctaacaaaa tgtctgaaat gcccgaaatg gggaaatact    2340
cacaaggtac agaaagctac caacaatttg ctattcgcat cgccgacatg cttttacaac    2400
ctgaaaaatt cagagagctt tatccaattt tagaaaaagc cggattcaaa gaatgattga    2460 aaagagata acaaaatttg agaaagagat tttgctacaa gacaaaatct ctcagctcga    2520
aaatgaacta aaagaatttt ctgatcttca aaaaaaagca tatagcgaac ggcttcaaaa    2580
aagtatcgtg ggtttagaaa atagaatcta tcgaatcaag aaaatgcttt atacaacctg    2640
aaaggttgtc aggggttaag gggaggattc cccttactca tgaactttca atgtaccttt    2700
aggtgctttg aaagtggagt gagtccactt cgctatcgca aagctcaaaa acctctgcta    2760
tcgtgtgttt tttcggtatc ggatttatca aatgtcattt gctattttgc gtattcaaaa    2820
attgaaatcg tttgcagacg ttggcggtag tctttcgcat aattatcgca atcgagaaac    2880
gttaaatgca gatgatgctc gtactcattt gaatgaacat acgctagata caaacgaaaa    2940
atgtatgtcc gcaatcag                                                  2958
```

<210> SEQ ID NO 69
<211> LENGTH: 324
<212> TYPE: PRT
<213> ORGANISM: artificial sequences
<220> FEATURE:
<221> NAME/KEY: SOURCE
<222> LOCATION: 1..324
<223> OTHER INFORMATION: /mol_type="protein"
      /note="sphinx1.76.324.pep"
      /organism="artificial sequences"

<400> SEQUENCE: 69

```
Met Ser Asp Leu Ile Val Lys Asp Asn Ala Leu Met Asn Ala Ser Tyr
1               5                   10                  15
```

Asn Leu Ala Leu Val Glu Gln Arg Leu Ile Leu Ala Ile Ile Glu
            20                  25                  30

Ala Arg Glu Thr Gly Lys Gly Ile Asn Ala Asn Asp Pro Leu Thr Val
        35                  40                  45

His Ala Gly Ser Tyr Ile Asn Gln Phe Asn Val Gln Arg His Thr Ala
50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Gln Val Ile Glu
            180                 185                 190

Leu Ala Leu Lys Gln Ile Asn Glu His Thr Asp Ile Thr Ala Ser Tyr
        195                 200                 205

Glu Gln His Lys Lys Gly Arg Val Ile Thr Gly Phe Ser Phe Met Phe
210                 215                 220

Lys His Lys Lys Gln Asn Ser Asp Lys Thr Pro Asp Thr Asn Ala Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
        275                 280                 285

Gly Asp Glu Ser Ala Ile Asp Met Met Lys Arg Ile Gln Ser Glu Ile
290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 70
<211> LENGTH: 308
<212> TYPE: PRT
<213> ORGANISM: artificial sequences
<220> FEATURE:
<221> NAME/KEY: SOURCE
<222> LOCATION: 1..308
<223> OTHER INFORMATION: /mol_type="protein"
      /note="HCBI4.296.308.PEP"
      /organism="artificial sequences"

<400> SEQUENCE: 70

Arg Ile Ala Asp Met Leu Leu Gln Pro Glu Lys Phe Arg Glu Leu Tyr
1               5                   10                  15

Pro Ile Leu Glu Lys Ala Gly Phe Lys Glu Ala Ser Asp Tyr Ala Ile
            20                  25                  30

Gln Phe Ser Val Ala Lys Glu Thr Ala Tyr Glu Ala Leu Lys Ser Ala
        35                  40                  45

Val Asn Asn Leu Phe Glu Arg Gln Phe Ser Phe Arg Glu Glu Thr Lys
 50                  55                  60

Lys Gly Thr Gly Ile Val Arg Ser Arg Trp Val Ser Arg Ile Lys Tyr
 65                  70                  75                  80

Ile Asp Asp Ala Ala Ile Leu Glu Ile Thr Phe Ala Pro Asp Val Val
                 85                  90                  95

Pro Leu Ile Thr Arg Leu Glu Glu His Phe Thr Ser Tyr Gln Ile Lys
            100                 105                 110

Gln Ile Ala Gln Leu Thr Ser Lys Tyr Ala Ile Arg Leu Tyr Glu Leu
        115                 120                 125

Leu Ile Ala Trp Arg Thr Thr Gly Lys Val Pro Glu Leu Glu Leu Ser
130                 135                 140

Glu Phe Arg Asn Arg Leu Gly Ile Ala Ser Asn Glu Tyr Thr Ala Met
145                 150                 155                 160

Asn Asn Phe Lys Ser Arg Val Leu Glu Pro Ser Ile Lys Gln Ile Asn
                165                 170                 175

Glu His Thr Asp Ile Thr Val Thr Tyr Glu Gln His Lys Lys Gly Arg
            180                 185                 190

Thr Ile Thr Gly Phe Ser Phe Arg Phe Lys Gln Lys Gln Gln Ala Lys
        195                 200                 205

Lys Ile Glu Thr Asn Arg Asp Pro Asn Thr Pro Asp Phe Phe Ile Lys
210                 215                 220

Met Thr Asp Ala Gln Arg His Leu Phe Ala Asn Lys Met Ser Glu Met
225                 230                 235                 240

Pro Glu Met Gly Lys Tyr Ser Gln Gly Thr Glu Ser Tyr Gln Gln Phe
                245                 250                 255

Ala Ile Met Lys Asn Gly Leu Val Val Lys Asp Asn Ala Leu Met Asn
            260                 265                 270

Ala Ser Tyr Asn Leu Glu Val Thr Glu Gln Arg Leu Ile Leu Leu Ala
        275                 280                 285

Ile Ile Ser Ala Arg Glu Thr Gly Gln Gly Ile Thr Ser Asp Ser Lys
290                 295                 300

Leu Glu Ile His
305

<210> SEQ ID NO 71
<211> LENGTH: 1368
<212> TYPE: DNA
<213> ORGANISM: artificial sequences
<220> FEATURE:
<221> NAME/KEY: source
<222> LOCATION: 1..1368
<223> OTHER INFORMATION: /mol_type="DNA"
      /note="AL391558"
      /organism="artificial sequences"

<400> SEQUENCE: 71
ttctaaagaa aaggtcattt taactgaatg ttttaattta tggttgaaaa ccaactttt      60 ctaaaacagg atacagttct ctaaattttt caggctctaa caacatattt gcgatacgta    120
tggcaaattg ttgatagctt tccgtaccct gtgaatactt ccccatttcg ggcatttcag    180
acattttatt tgcaaataaa tgacgttgtg catcggtcat tttgacaaaa aaatcagggg    240
tatttggatc acgtttaatt tcaacttttcg gctgttgttt atgcttaaat ttgaatgaaa   300

```
accctgtgat ggtacgccct tgtttatgct gttcataagt tgcttttatg tctgtatgct      360
cattgatttg agtaatagct gtttctagta cacggctttt aaaatggtgc atacgttgat      420
actcatcatc gtccacacct aagtttttac gtagctgttg cagttcaaag gttggcgttt      480
ttccaacttc acgccaagcg attaataatt cataaagtct agtggcgtac ttactcgtta      540
ggtgtgcaac ttgtttcgct tcatattttg taaaatgctc ttccaatcga gtgattaaag      600
gtactacatc aggtgcgaaa gtaatttcta gtaatgctaa gtcatctaca taaaaaatac      660
ggctaaccca acgagagcga acaataccta ctttccccgt tcttttatat tcagccgtat      720
agctaaactg tctattaaac agattgttta cagcttcttt tagggcttta taggatgcat      780
ctggcgacac attaaatagc tttgcataat cactagcatg tatttctagt ttgctatctg      840
ccgtgattcc ctgccctaat tcccttgcat taattattgc cagcataatt aaacgctgtt      900
ctgttagttc taaattataa cttgcgttta ttaatgcatt atctttcaca actaaaccat      960
tcttcatatt aaatacacgt tattattaat gtgtatttac acactacata taatatgtgt     1020
gttaatcaag agaatttgtg tgcttataca agagaatttg tgtgcttata caagagaatt     1080
tgtgtgctta tacaagagaa tttgtgtgct tatataggct gaaacatact gatatcaatg     1140
ctttcagcta gtctaaaagc atttaaaagc tttaaaaata attaaaagcc taacggcagg     1200
ggagtacaac tgccctaggt actcgctaaa gctcgtactc tattgctgtt cgctctgctc     1260
acagcgaggg gcagttttgg ttaattctat ttgtgaaatt taaaagcaaa agcaattatg     1320
aattcgctac gctcataaac cttttttact cgcttacgct cgatcatg                  1368
```

<210> SEQ ID NO 72
<211> LENGTH: 1724
<212> TYPE: DNA
<213> ORGANISM: artificial sequences
<220> FEATURE:
<221> NAME/KEY: source
<222> LOCATION: 1..1724
<223> OTHER INFORMATION: /mol_type="DNA"
      /note="HCBI5.173"
      /organism="artificial sequences"

<400> SEQUENCE: 72

```
ccattagctt tatagtgcca agtaatatct agtaaacgga tatgttttat atgatctttt       60
ctttgaaaat gaagaatcat atctgaggtc gaatagttgt tatatttact ttttacgtaa      120
tcaggcatac cgatatgata atgccaaaga ttattcgaat atgtgaaatc atagattgga      180
tcagttttgt ctattccacg ccatgaaggt gcaattttac cttggtattt agaaaaatcc      240
tttaaaccaa actcttcata gatatcagtg aaatctaaaa ttttatcttg ttgatcttca      300
ggataacgcc caaattgaac tgcaaattgt tttccaaatt cccaagagta agacaattac      360
tttttccctg cttctaatat taatcttctt ttctcttctc tgcttaaacc ttgaggcata      420
acaaggtttc tgaatcaag agctgatttc attctatcaa gattaatacg aacaggtgct      480
gttttttgat tgatgtttg ggtaataacg aagcccatta cattcatttg ccacctcgac      540
aaataaaaat ttcttttaaa attttaacaa aaaaaatagc gtagcgggtt tttaattgtt      600
tttaaatact tttaattgtt tttagacctg ctgaaacccg ctatacaaaa ggctttcagg      660
ccatataaaa agacatttac cctgccataa aaagacattt accctgccat aaaaagacat      720
ttaccctgcc ataaaagac atttaccctg cttaaaaaga catttacaa atgtctttt       780 taatggtagc tttaggttgt tttttataaa aaaaattggc gttaaaaaaa tatggattta      840
gtcgttaaag ataataattt gatcaatgct agctactccc taggtttggt tgagcaacgt      900
```

```
cttgtattgc tagctatcat tgaagctaga gaatctagta aggggataga ttcagaaaca    960
ttnttagaaa tacatgctca acactatgca gatagatttg atgtaaatgt aaaaaatacg   1020
tatgccatgc tttcagaggc ggcacagact cttttaatc gtcaagtcac ttacatgatg   1080
gttgatgaaa aaggaataa acctgaaaag cgtgtaattc gctgggttag tggtatttca    1140
tatgtagaag gggctggagt tcttaaactt cgttttctc cagaaattgt ccctctaata    1200
actaggctag agcaaaattt tacgagttat gaactagaac aagttaaaag cttaaacgta   1260
tatgcaactc gactatatga attattagtc tgttggcgta gtacaggtaa aactcccatt   1320
attgaaatag aagattttcg ttcaaaaata ggagtcttac ctactgaata taaattaatg   1380
agtgatttca aaaagcgagt ttttgagcca gcaatacagc aaattaataa aaacacagat   1440
ttgacggtta attatgatca acataaatca ggccgtacaa ttacaggctt ctcatttaaa   1500
tttaagcaaa agaaaacgaa atcagaaaag gtcgtaaccg ctaaacgaga cccaaataca   1560
cctgactttt ttgtaaaaat gaccgattct caacgtcatt tattcgcaac taaactttct   1620
gaaatgccag agatgtctaa atattctcaa ggtacagagt cgtatcaaca gtttgctatc   1680
cgtattgccg atatgctttt agaacctgaa aagttaaaga attc                    1724
```

<210> SEQ ID NO 73
<211> LENGTH: 324
<212> TYPE: PRT
<213> ORGANISM: artificial sequences
<220> FEATURE:
<221> NAME/KEY: SOURCE
<222> LOCATION: 1..324
<223> OTHER INFORMATION: /mol_type="protein"
      /note="Sphinx1.76.324.PEP"
      /organism="artificial sequences"

<400> SEQUENCE: 73

```
Arg Ile Gln Ser Glu Ile Ile Thr Asp Ala Ile Ala Asp Gln Trp Glu
1               5                   10                  15

Ser Lys Leu Glu Glu Phe Gly Val Val Phe Gly Ser Tyr Ile Asn Gln
            20                  25                  30

Phe Asn Val Gln Arg His Thr Ala Tyr Gln Ala Leu Lys Asp Ala Cys
        35                  40                  45

Lys Asp Leu Phe Ala Arg Gln Phe Ser Tyr Gln Glu Lys Arg Glu Arg
    50                  55                  60

Gly Arg Ile Asn Ile Thr Ser Arg Trp Val Ser Gln Ile Gly Tyr Met
65                  70                  75                  80

Asp Asp Thr Ala Thr Val Glu Ile Ile Phe Ala Pro Ala Val Val Pro
                85                  90                  95

Leu Ile Thr Arg Leu Glu Glu Gln Phe Thr Gln Tyr Asp Ile Glu Gln
            100                 105                 110

Ile Ser Gly Leu Ser Ser Ala Tyr Ala Val Arg Met Tyr Glu Leu Leu
        115                 120                 125

Ile Cys Trp Arg Ser Thr Gly Lys Thr Pro Ile Ile Glu Leu Asp Glu
    130                 135                 140

Phe Arg Lys Arg Ile Gly Val Leu Asp Thr Glu Tyr Thr Arg Thr Asp
145                 150                 155                 160

Asn Leu Lys Met Gln Val Ile Glu Leu Ala Leu Lys Gln Ile Asn Glu
                165                 170                 175

His Thr Asp Ile Thr Ala Ser Tyr Glu Gln His Lys Lys Gly Arg Val
            180                 185                 190
```

```
Ile Thr Gly Phe Ser Phe Met Phe Lys His Lys Gln Asn Ser Asp
            195                 200                 205

Lys Thr Pro Asp Thr Asn Ala Ser Ser Pro Arg Ile Val Lys His Ser
    210                 215                 220

Gln Ile Pro Thr Asn Ile Val Lys Gln Pro Glu Asn Ala Lys Met Ser
225                 230                 235                 240

Asp Leu Glu His Arg Ala Ser Arg Val Thr Gly Glu Ile Met Arg Asn
                245                 250                 255

Arg Leu Ser Asp Arg Phe Lys Gln Gly Asp Ser Ala Ile Asp Met
                260                 265                 270

Met Lys Met Ser Asp Leu Ile Val Lys Asp Asn Ala Leu Met Asn Ala
                275                 280                 285

Ser Tyr Asn Leu Ala Leu Val Glu Gln Arg Leu Ile Leu Leu Ala Ile
            290                 295                 300

Ile Glu Ala Arg Glu Thr Gly Lys Gly Ile Asn Ala Asn Asp Pro Leu
305                 310                 315                 320

Thr Val His Ala

<210> SEQ ID NO 74
<211> LENGTH: 299
<212> TYPE: PRT
<213> ORGANISM: artificial sequences
<220> FEATURE:
<221> NAME/KEY: SOURCE
<222> LOCATION: 1..299
<223> OTHER INFORMATION: /mol_type="protein"
      /note="HCBI5.173.299.PEP"
      /organism="artificial sequences"

<400> SEQUENCE: 74

Met Asp Leu Val Val Lys Asp Asn Asn Leu Ile Asn Ala Ser Tyr Ser
1               5                   10                  15

Leu Gly Leu Val Glu Gln Arg Leu Val Leu Leu Ala Ile Ile Glu Ala
                20                  25                  30

Arg Glu Ser Ser Lys Gly Ile Asp Ser Glu Thr Xaa Leu Glu Ile His
            35                  40                  45

Ala Gln His Tyr Ala Asp Arg Phe Asp Val Asn Val Lys Asn Thr Tyr
        50                  55                  60

Ala Met Leu Ser Glu Ala Ala Gln Thr Leu Phe Asn Arg Gln Val Thr
65                  70                  75                  80

Tyr Met Met Val Asp Glu Lys Arg Asn Lys Pro Glu Lys Arg Val Ile
                85                  90                  95

Arg Trp Val Ser Gly Ile Ser Tyr Val Glu Gly Ala Gly Val Leu Lys
                100                 105                 110

Leu Arg Phe Ser Pro Glu Ile Val Pro Leu Ile Thr Arg Leu Glu Gln
            115                 120                 125

Asn Phe Thr Ser Tyr Glu Leu Glu Gln Val Lys Ser Leu Asn Val Tyr
        130                 135                 140

Ala Thr Arg Leu Arg Ile Ala Asp Met Leu Leu Glu Pro Glu Lys Leu
145                 150                 155                 160

Lys Asn Ser His Asn Lys Asn Thr Asp Leu Thr Val Asn Tyr Asp Gln
                165                 170                 175

His Lys Ser Gly Arg Thr Ile Thr Gly Phe Ser Phe Lys Phe Lys Gln
                180                 185                 190

Lys Lys Thr Lys Ser Glu Lys Val Val Thr Ala Lys Arg Asp Pro Asn
            195                 200                 205
```

```
Thr Pro Asp Phe Phe Val Lys Met Thr Asp Ser Gln Arg His Leu Phe
    210                 215                 220

Ala Thr Lys Leu Ser Glu Met Pro Glu Met Ser Lys Tyr Ser Gln Gly
    225                 230                 235                 240

Thr Glu Ser Tyr Gln Gln Phe Ala Ile Tyr Glu Leu Leu Val Cys Trp
                    245                 250                 255

Arg Ser Thr Gly Lys Thr Pro Ile Ile Glu Ile Glu Asp Phe Arg Ser
                260                 265                 270

Lys Ile Gly Val Leu Pro Thr Glu Tyr Lys Leu Met Ser Asp Phe Lys
                275                 280                 285

Lys Arg Val Phe Glu Pro Ala Ile Gln Gln Ile
    290                 295
```

<210> SEQ ID NO 75
<211> LENGTH: 1041
<212> TYPE: DNA
<213> ORGANISM: artificial sequences
<220> FEATURE:
<221> NAME/KEY: source
<222> LOCATION: 1..1041
<223> OTHER INFORMATION: /mol_type="DNA"
    /note="GU978996"
    /organism="artificial sequences"

<400> SEQUENCE: 75

```
taaaacgagg tttaccttgc attaaaacga ggtttaccct gcattaaaac gaggtttacc      60
ttgcattaaa acgaggttta ccttgcatta agcgagttaa taatataacc tcgtcttatt    120
aaattaaaaa cataatcttt tcatatgaaa acagaactaa tagttaaaga taatgcctta    180
attaatgcca gttataacct tgatctagtg gagcaacggt taattctttt agcgatcctt    240
gaagcaagga aatcgggtaa aggaataaat gctaatgatc ctttaacagt tcatgctgaa    300
agttatatca atcaatttgg tgttcatcga aatacggctt atcaagcatt aaaagatgct    360
tgtgatgatc tattcgtaag acaatttagt tatcaaagcc ttagtgaaaa aggaaatgtt    420
attaatcaca aatcaagatg ggtgagtgag gttgcttata ttgataacga ggctgtcgtt    480
agacttatct ttgctcccgc tattgtgcct ttaattacta gactagaaga acaatttaca    540
aagtatgaaa tacaacaaat aagcaattta acaagtgctt atgccgttcg tttatatgaa    600
atattaattg catggcgtag taccggaaaa acgcctctca taaccctgta cgacttcaga    660
caaaaaatag gtgtactcga tactgaatac aaacgaatgt atgattttaa aaaatatgtc    720
ttggacattg cattaaaaca agtcaatgaa cataccgata ttactgtcaa agttgaacag    780
cataagacgg gcagatcaat tactggcttt tcatttagct ttaaacaaaa aaagtcagct    840
actcagtctg tcggatctaa aagagatcca aatacattgg acccttttc aacaatgaca    900
gataaacaac gtcatctatt ccagcagttt gctgtacgta tcgctggcat gctgcaagat    960
acagagcgat ttagggaaat tgctagtaaa ctctccgagc ttcctgagat gagtaaatat   1020
tcacaaggta cggaaagcta t                                             1041
```

<210> SEQ ID NO 76
<211> LENGTH: 158
<212> TYPE: DNA
<213> ORGANISM: artificial sequences
<220> FEATURE:
<221> NAME/KEY: source
<222> LOCATION: 1..158
<223> OTHER INFORMATION: /mol_type="DNA"
    /note="BlastN2 Query25"
    /organism="artificial sequences"

<400> SEQUENCE: 76
gctatccgta ttgccgatat gcttttagaa cctgaaaact ttctgaaatg ccagagatgt    60
ctaaatattc tcaaggtaca gagtcgtatc aacagtttaa tacacctgac ttttttgtaa   120
aaatgaccga ttctcaacgt catttattcg caactaaa                           158

<210> SEQ ID NO 77
<211> LENGTH: 158
<212> TYPE: DNA
<213> ORGANISM: artificial sequences
<220> FEATURE:
<221> NAME/KEY: source
<222> LOCATION: 1..158
<223> OTHER INFORMATION: /mol_type="DNA"
      /note="BlastN2 Subject25"
      /organism="artificial sequences"

<400> SEQUENCE: 77
gctattcgta tcgctgatat gcttttagag cctgaaaaat gtctgaaatg cctgatatga    60
gtaaatattc gcaaggaaca gaaagctacc aacaatttaa tacacctgac ttttttgtca   120
aaatgactga tgcccaacgt catttatttg ccaataaa                           158

<210> SEQ ID NO 78
<211> LENGTH: 161
<212> TYPE: DNA
<213> ORGANISM: artificial sequences
<220> FEATURE:
<221> NAME/KEY: source
<222> LOCATION: 1..161
<223> OTHER INFORMATION: /mol_type="DNA"
      /note="BlastN2 Query26"
      /organism="artificial sequences"

<400> SEQUENCE: 78
cagtttgcta tccgtattgc cgatatgctt ttagaacctg aactaaactt tctgaaatgc    60
cagagatgtc taaatattct caaggtacag agtcgtatca agacccaaat acacctgact   120 ttttgtaaa aatgaccgat tctcaacgtc atttattcgc a                        161

<210> SEQ ID NO 79
<211> LENGTH: 161
<212> TYPE: DNA
<213> ORGANISM: artificial sequences
<220> FEATURE:
<221> NAME/KEY: source
<222> LOCATION: 1..161
<223> OTHER INFORMATION: /mol_type="DNA"
      /note="BlastN2 Subject26"
      /organism="artificial sequences"

<400> SEQUENCE: 79
cagtttacaa ttcgcattgc tgatatgctt ttacaacctg aaataaaatg tctgaaatgc    60
ctgaaatgat taaatattct caaggcacag aaagctatca agacccaaac acaccgact    120 tctttataaa aatgactgat gcacaacgcc atctattcgc c                       161

<210> SEQ ID NO 80
<211> LENGTH: 152
<212> TYPE: DNA
<213> ORGANISM: artificial sequences
<220> FEATURE:
<221> NAME/KEY: source
<222> LOCATION: 1..152
<223> OTHER INFORMATION: /mol_type="DNA"
      /note="BlastN2 Query27"

/organism="artificial sequences"

<400> SEQUENCE: 80
attgccgata tgctttaga acctgaaaag ttatgccaga gatgtctaaa tattctcaag    60
gtacagagtc gtatcaacag tttgctatcc gtgactttt tgtaaaaatg accgattctc   120
aacgtcattt attcgcaact aaactttctg aa                                152

<210> SEQ ID NO 81
<211> LENGTH: 152
<212> TYPE: DNA
<213> ORGANISM: artificial sequences
<220> FEATURE:
<221> NAME/KEY: source
<222> LOCATION: 1..152
<223> OTHER INFORMATION: /mol_type="DNA"
      /note="BlastN2 Subject27"
      /organism="artificial sequences"

<400> SEQUENCE: 81
atcgctgaca tgctttaga gcctgaaaag ttatgcctga aatgagcaaa tattcacaag    60
gcacagaaag ctatcaacag tttgctatcc gtgacttctt tgtcaaaatg accgatgcac   120
aacgccatct attcgccaat aaaatgtctg ag                                152

<210> SEQ ID NO 82
<211> LENGTH: 153
<212> TYPE: DNA
<213> ORGANISM: artificial sequences
<220> FEATURE:
<221> NAME/KEY: source
<222> LOCATION: 1..153
<223> OTHER INFORMATION: /mol_type="DNA"
      /note="BlastN2 Query28"
      /organism="artificial sequences"

<400> SEQUENCE: 82
tattgccgat atgctttag aacctgaaaa gttaatgcca gagatgtcta aatattctca    60
aggtacagag tcgtatcaac agtttgctat ccgtgacttt tttgtaaaaa tgaccgattc   120
tcaacgtcat ttattcgcaa ctaaactttc tga                               153

<210> SEQ ID NO 83
<211> LENGTH: 153
<212> TYPE: DNA
<213> ORGANISM: artificial sequences
<220> FEATURE:
<221> NAME/KEY: source
<222> LOCATION: 1..153
<223> OTHER INFORMATION: /mol_type="DNA"
      /note="BlastN2 Subject28"
      /organism="artificial sequences"

<400> SEQUENCE: 83
tatcgctgac atgctttag agcctgaaaa gttgatgcct gaaatgagca atattcaca    60 aggcacagaa agctatcaac agtttttctat ccgtgacttc tttgtcaaaa tgaccgatgc   120
acaacgccat ctattcgcca ataaaatgtc tga                               153